United States Patent
Larocca et al.

(10) Patent No.: US 10,227,561 B2
(45) Date of Patent: Mar. 12, 2019

(54) METHODS AND COMPOSITIONS FOR TARGETING PROGENITOR CELL LINES

(71) Applicants: Mandala Biosciences, LLC, Alameda, CA (US); BioTime, Inc., Alameda, CA (US); Sanford-Burnham Medical Research Institute, La Jolla, CA (US)

(72) Inventors: Dana Larocca, Alameda, CA (US); Paola Bignone, Alameda, CA (US); Michael D. West, Mill Valley, CA (US); Evan Snyder, La Jolla, CA (US)

(73) Assignees: Mandala Biosciences, LLC, Alameda, CA (US); BioTime, Inc., Alameda, CA (US); Sanford-Burnham Medical Research Institute, La Jolla, CA (US)

( * ) Notice: Subject to any disclaimer, the term of this patent is extended or adjusted under 35 U.S.C. 154(b) by 0 days.

(21) Appl. No.: 14/930,505

(22) Filed: Nov. 2, 2015

(65) Prior Publication Data

US 2017/0121676 A1    May 4, 2017

Related U.S. Application Data

(63) Continuation of application No. 13/972,695, filed on Aug. 21, 2013, now Pat. No. 9,175,263.

(60) Provisional application No. 61/769,119, filed on Feb. 25, 2013, provisional application No. 61/692,139, filed on Aug. 22, 2012.

(51) Int. Cl.
*C12N 5/00* (2006.01)
*C07K 7/08* (2006.01)
*C12N 5/0735* (2010.01)

(52) U.S. Cl.
CPC .............. *C12N 5/0606* (2013.01); *C07K 7/08* (2013.01)

(58) Field of Classification Search
CPC ................................ C12N 5/0606; C07K 7/08
See application file for complete search history.

(56) References Cited

U.S. PATENT DOCUMENTS

| | | | |
|---|---|---|---|
| 9,175,263 B2 | 11/2015 | Larocca et al. | |
| 2007/0155013 A1* | 7/2007 | Akaike | C12N 5/0606 435/455 |
| 2008/0070303 A1 | 3/2008 | West et al. | |
| 2008/0233610 A1 | 9/2008 | Thomson | |
| 2009/0047263 A1 | 2/2009 | Yamanaka | |
| 2010/0003757 A1 | 1/2010 | Mack | |
| 2010/0055678 A1* | 3/2010 | Jaatinen | G01N 33/5002 435/5 |
| 2010/0166713 A1* | 7/2010 | Dalton | C12N 5/0603 424/93.7 |
| 2010/0184033 A1* | 7/2010 | West | C12N 5/0606 435/6.16 |
| 2010/0255580 A1* | 10/2010 | Rezania | C12N 5/0606 435/377 |
| 2010/0267135 A1* | 10/2010 | Sakurada | C12N 5/0696 435/366 |
| 2011/0223669 A1* | 9/2011 | Yamanaka | C12N 5/0696 435/455 |
| 2012/0171171 A1 | 7/2012 | West et al. | |
| 2013/0115673 A1* | 5/2013 | West | C12N 5/0606 435/178 |
| 2013/0236961 A1* | 9/2013 | Amit | C12N 5/0606 435/366 |

OTHER PUBLICATIONS

Bignone et al., Identification of human embryonic progenitor cell targeting peptides using phage display. PLoS One. 2013;8(3):e58200. 12 pages.
Blanpain et al., Stem cells assessed. Nat Rev Mol Cell Biol. Jun. 8, 2012;13(7):471-6.
Blum et al., The tumorigenicity of diploid and aneuploid human pluripotent stem cells. Cell Cycle. Dec. 2009;8(23):3822-30.
Cohen et al., Turning straw into gold: directing cell fate for regenerative medicine. Nat Rev Genet. Apr. 2011;12(4):243-52.
Dubois et al., SIRPA is a specific cell-surface marker for isolating cardiomyocytes derived from human pluripotent stem cells. Nat Biotechnol. Oct. 23, 2011;29(11):1011-8.
Grützkau et al., Small but mighty: how the MACS-technology based on nanosized superparamagnetic particles has helped to analyze the immune system within the last 20 years. Cytometry A. Jul. 2010;77(7):643-7.
Hölig et al., Novel RGD lipopeptides for the targeting of liposomes to integrin-expressing endothelial and melanoma cells. Protein Eng Des Sel. May 2004;17(5):433-41.
Jaiswal et al., Long-term multiple color imaging of live cells using quantum dot bioconjugates. Nat Biotechnol. Jan. 2003;21(1):47-51.
Laposa, Stem cells for drug screening. J Cardiovasc Pharmacol. Sep. 2011;58(3):240-5.
Lin et al., Quantum dot imaging for embryonic stem cells. BMC Biotechnol. Oct. 9, 2007;7:67. 10 pages.
Lu et al., Targeting of embryonic stem cells by peptide-conjugated quantum dots. PLoS One. Aug. 10, 2010;5(8):e12075. 10 pages.
Molek et al., Peptide phage display as a tool for drug discovery: targeting membrane receptors. Molecules. Jan. 21, 2011;16(1):857-87.
Nakagawa et al., Reprogramming of somatic cells to pluripotency. Adv Exp Med Biol. 2010;695:215-24.
Nelson et al., Induced pluripotent stem cells: advances to applications. Stem Cells Cloning. Jan. 1, 2010;3:29-37.
Rasmussen et al., TNFerade Biologic: preclinical toxicology of a novel adenovector with a radiation-inducible promoter, carrying the human tumor necrosis factor alpha gene: (2002) Cancer Gene Ther 9:606.
Shah et al., Labeling of mesenchymal stem cells by bioconjugated quantum dots. Nano Lett. Oct. 2007;7(10):3071-9.

(Continued)

*Primary Examiner* — Amber D Steele
(74) *Attorney, Agent, or Firm* — McCarter & English, LLP; Jonathan M. Sparks; Wendy Thai

(57) ABSTRACT

The invention provides methods, compositions and kits for the identification and enrichment of progenitor cell lines obtained from pluripotent stem cells.

7 Claims, 19 Drawing Sheets

Specification includes a Sequence Listing.

(56) References Cited

OTHER PUBLICATIONS

Slotkin et al., In vivo quantum dot labeling of mammalian stem and progenitor cells. Dev Dyn. Dec. 2007;236(12):3393-401.

Spear et al., Isolation, characterization, and recovery of small peptide phage display epitopes selected against viable malignant glioma cells. Cancer Gene Ther. Jul. 2001;8(7):506-11.

Sternberg et al., A human embryonic stem cell-derived clonal progenitor cell line with chondrogenic potential and markers of craniofacial mesenchyme. Regen Med. Jul. 2012;7(4):481-501.

Teesalu et al., Mapping of vascular ZIP codes by phage display. Methods Enzymol. 2012;503:35-56.

Tiscornia et al., Diseases in a dish: modeling human genetic disorders using induced pluripotent cells. Nat Med. Dec. 2011;17(12):1570-6.

West et al., The ACTCellerate initiative: large-scale combinatorial cloning of novel human embryonic stem cell derivatives. Regen Med. May 2008;3(3):287-308.

Yuan et al., Cell-surface marker signatures for the isolation of neural stem cells, glia and neurons derived from human pluripotent stem cells. PLoS One. Mar. 2, 2011;6(3):e17540. 16 pages.

Zhao et al., Isolation and initial application of a novel peptide that specifically recognizes the neural stem cells derived from rhesus monkey embryonic stem cells. J Biomol Screen. Jul. 2010;15(6):687-94.

Zhao et al., Novel peptide ligands that bind specifically to mouse embryonic stem cells. Peptides. Nov. 2010;31(11)2027-34.

* cited by examiner

| Name | Frequency | Sequence | SEQ ID NO |
|---|---|---|---|
| W10-R2-14 | 3/24 | SWTYSYPNQNMD-- | 39 |
| W10-R2-8 | 1/24 | DWTYSLPGLVEE-- | 40 |
| W10-R2-4 | 2/24 | NWTWSMPTGNPA-- | 41 |
| W10-R2-15 | 1/24 | GMTLRVLTN-YTE- | 42 |
| W10-R2-18 | 1/24 | --TLHVSENSWTYN | 43 |
| W10-R3-18 | 2/24 | DWLWSFAPNVDT-- | 44 |
| W10-R2-23 | 1/24 | TLSSQNPYMHKK-- | 45 |
| W10-R3-10 | 3/24 | -IDKQMMTSHKAI- | 46 |
| W10-R3-24 | 1/24 | QGMETQKLRMLK-- | 47 |
| W10-R2-21 | 1/24 | GWYWETPLDMFN-- | 48 |
| W10-R2-11 | 1/24 | GWVIDYDYYPMR-- | 49 |
| W10-R2-24 | 1/24 | VTAENYQSFSVS-- | 50 |
| W10-R2-10 | 1/24 | NNKMSSEMMSIV-- | 51 |
| W10-R2-6 | 1/24 | STGTDLHSNARI-- | 52 |
| W10-R2-1 | 2/24 | -YEFDNLLNRTLW- | 53 |
| W10-R2-5 | 1/24 | EWTVNERTMWDL | 54 |

FIG.2C

| ProbeID | Access ion | Definit ion | Symbo l | CASM C P14 Contro l 1 | CASM C P19 Contro l 2 | CASMC Ctrl mean | CASM C P14 D14 MM 1 | CASM C P19 D14 MM 2 | CASMC MM mean |
|---|---|---|---|---|---|---|---|---|---|
| 4010136 | NM_00 | Homo s | COL2A1 | 61.78 | 48.17 | 54.98 | 58.15 | 54.77 | 56.46 |
| 6280133 | NM_00 | Homo s | MYH11 | 259.3 | 550.1 | 404.73 | 3187 | 3035 | 3110.98 |
| 6480059 | NM_00 | Homo s | ACTA2 | 15751 | 15640 | 15695.69 | 18052 | 19678 | 18864.67 |
| 4850630 | NM_00 | Homo s | CNN1 | 155 | 131.4 | 143.18 | 1827 | 1296 | 1561.61 |
| 7160343 | NM_05 | Homo s | MYLK | 454.1 | 602.8 | 528.44 | 1713 | 1841 | 1776.84 |

FIG.9A

| Accession | Definition | Symbol | W10 P14 Control 1 | W10 P12 Control 2 | W10 P14 Control 3 | W10 Ctrl mean | W10 Ctrl SD | W10 P14 D14 MM 1 | W10 P15 D14 MM 2 | W10 P14 D14 MM 3 | W10 MM mean | W10 MM SD | W10 MM |
|---|---|---|---|---|---|---|---|---|---|---|---|---|---|
| NM_001844. | Homo sapiens | COL3A1 | 51.2935 | 53.2754 | 58.8316 | 54.47 | 2.93 | 51.1650 | 54.0643 | 61.6658 | 55.63 | | 4.01 |
| NM_002474. | Homo sapiens | MYH11 | 38.7016 | 43.8257 | 47.8155 | 43.45 | 2.42 | 878.5200 | 2357.9922 | 13153.3403 | 5463.28 | | 5557.57 |
| NM_001613. | Homo sapiens | ACTA2 | 120.2041 | 119.9718 | 213.7392 | 151.31 | 47.74 | 14888.7030 | 19387.3380 | 4185.8173 | 12820.62 | | 7624.17 |
| NM_001299. | Homo sapiens | CNN1 | 102.8980 | 104.4509 | 617.8656 | 275.07 | 261.47 | 368.4579 | 1062.0182 | 34487.9754 | 11972.82 | | 170045.40 |
| NM_053032. | Homo sapiens | MYLK | 560.9086 | 547.4860 | 184.3215 | 430.91 | 185.42 | 1391.2794 | 3986.4355 | 1822.0647 | 2399.93 | | 1120.67 |

| Accession | Definition | Symbol | 4D20.8 P11 Control 1 | 4D20.8 P11 Control 2 | 4D20.8 P17 Control 3 | 4D20.8 Ctrl mean | 4D20.8 Ctrl SD | 4D20.8 P11 D14 MM 1 | 4D20.8 P17 D14 MM 2 | 4D20.8 P17 D14 MM 3 | 4D20.8 MM mean | 4D20.8 SD | MM |
|---|---|---|---|---|---|---|---|---|---|---|---|---|---|
| NM_001844. | Homo sapiens | COL3A1 | 72.8695 | 61.2067 | 70.0975 | 68.06 | 4.66 | 914.1447 | 873.6643 | 1441.7406 | 1076.52 | | 287.83 |
| NM_002474. | Homo sapiens | MYH11 | 57.9305 | 54.3931 | 63.5130 | 58.61 | 4.56 | 69.0507 | 106.8265 | 97.3066 | 91.06 | | 7.94 |
| NM_001613. | Homo sapiens | ACTA2 | 13529.2858 | 8654.8028 | 7807.0711 | 9997.05 | 1104.26 | 17333.9600 | 13462.1342 | 9253.4630 | 13349.85 | | 2398.12 |
| NM_001299. | Homo sapiens | CNN1 | 382.7175 | 270.3578 | 140.3491 | 264.47 | 73.42 | 279.6511 | 214.9984 | 144.5978 | 213.08 | | 40.10 |
| NM_053026. | Homo sapiens | MYLK | 163.1268 | 91.9327 | 105.5215 | 120.19 | 14.13 | 85.0248 | 102.2735 | 75.3259 | 87.54 | | 13.49 |

FIG.9B

Analysis of binding W10 peptide phages.
PSI-Blast search on *Homo Sapiens* RefSeq protein database

| name | sequences | homology | Score | aa overlap | % Identity | % Similarity (% Gaps) | Protein | Accession number |
|---|---|---|---|---|---|---|---|---|
| W10-R3-18 | DWLWSFAPNVDT | 523 WLWSFQP | 26.2 | 7 | 86 | 86 (0) | Plexin-B1 precursor | NP_002664.2 |
| W10-R2-1 | YEFDNLLNRTLW | 215 DFQHLLNRTL | 25.7 | 10 | 70 | 80 (0) | disintegrin and metalloproteinase domain-containing protein 15 isoform 9 preprotein (and other isoforms) | NP_001246395.1 |
| W10-R2-21 | GWYWETPLEMFN | 121 ETPLDM | 24.0 | 6 | 100 | 100 (0) | palmitoyltransferase ZDHHC13 isoform 1 (also isoform 2) | NP_001001483.1 |
| W10-R2-11 | GWVIDYDYYPMR | 803 GWVIYKDYQYY | 26.2 | 11 | 73 | 73 (18) | Macrophage mannose receptor 1 precursor | NP_002429.1 |

FIG.10A

Homology of binding W10 peptides.

| protein | start | sequence | end |
|---|---|---|---|
| W10-R2-11 | 1 | GWVIDYDYYPMR | 12 |
| W10-R2-21 | 1 | GWYWETPLEMFN | 12 |
| W10-R3-18 | 1 | DWLWSFAPNVDT | 12 |
| WNT5A-like | 87 | DWLWY | 90 |
| Plexin B3 | 538 | WLWS | 542 |
| Plexin B1 | 523 | WLWSFQP | 529 |
| Semaphorin 3C | 19 | SFWPNVNT | 26 |

| protein | start | sequence | end |
|---|---|---|---|
| W10-R2-1 | 1 | YEFDNLLNRTLW | 12 |
| Plexin B2 | 1320 | YQF NLLN | 1327 |
| Plexin B2 | 190 | LLDRT | 194 |
| Plexin B2 | 245 | NRTL | 248 |

FIG.10B

| SEQUENCE | SEQ ID NO |
|---|---|
| DWLWSFAPNVDT | 55 |
| YEFDNLLNRTLW | 56 |
| GWYWETPLDMFN | 57 |
| GWVIDYDYYPMR | 58 |
| WLWDFQP | 59 |
| DFQNLLNRTL | 60 |
| ETPLDM | 61 |
| GWVIYKDYQYY | 62 |
| GWVIDYDYYPMR | 63 |
| GWYWETPLDMFN | 64 |
| DWLWSFAPNVDT | 65 |
| DWLWY | 66 |
| WLWS | 67 |
| WLWSFQP | 68 |
| SFNPNVNT | 69 |
| YEFDNLLNRTLW | 70 |
| YQFNLLN | 71 |
| LLDRT | 72 |
| NRTL | 73 |

SEQ ID NOS FROM 10A AND 10B

FIG.10C

METHODS AND COMPOSITIONS FOR TARGETING PROGENITOR CELL LINES

This application is a CON of U.S. application Ser. No. 13/972,695, filed on Aug. 21, 2013 (now U.S. Pat. No. 9,175,263), which claims priority to U.S. Provisional Application No. 61/769,119 filed on Feb. 25, 2013 and to U.S. Provisional Application No. 61/692,139 filed on Aug. 22, 2012, the contents of which are hereby incorporated by reference in their entireties.

FIELD OF THE INVENTION

The field of the invention relates to progenitor cells derived from pluripotent stem cells.

BACKGROUND

Pluripotent stem cells (PS), such as human pluripotent stem (hPS) cells, are capable of immortal proliferation in vitro and differentiation into derivatives of all three embryonic germ layers (Cohen D E, Melton D (2011) *Nat Rev Genet* 12: 243). As a result, the isolation of hPS cells, which include human embryonic stem (hES) cells and induced pluripotent stem (iPS) cells (Blanpain et al. (2012) *Nat Rev Mol Cell Biol* 13: 471), has spurred new avenues of research to evaluate their potential to provide a renewable source of human cells for basic research and as replacement cells for the treatment of injury, aging, or any one of a number of intractable degenerative diseases such as osteoarthritis, cardiovascular disease, macular degeneration, Parkinson's and perhaps even Alzheimer's disease (Cohen D E, Melton D (2011) Nat Rev Genet 12: 243; Blanpain et al. (2012) Nat Rev Mol Cell Biol 13: 471). Reprogramming methods for creating iPS cells from somatic cells (Nakagawa (2010) *Adv Exp Med Biol* 695: 215) have greatly expanded the number and diversity of PS cell lines, including hPS cell lines, available for research. Donor-derived hPS cells are a source of patient matched cell types for disease modeling (Tiscornia et al. (2011) *Nat Med* 17: 1570), drug screening (Laposa (2011) *J Cardiovasc Pharmacol* 58: 240), and the development of potential autologous cell replacement therapies (Nelson et al. (2010) *Stem Cells Cloning* 3: 29). However, there remains a need for efficient directed differentiation methods and improved cell purification technologies for deriving various cell types with sufficient purity and known identity to meet the standards required for translation into routine clinical application.

Current directed differentiation methods for obtaining specific mature cell types from hPS cells are sometimes limited by low efficiencies of reproducibly yielding the desired cell types, and in certain instances, such preparations rarely exceed 30% purity (Cohen, Melton (2011) *Nat Rev Genet* 12: 243). One approach to increasing the yield is enrichment of desired cell types using one or more progenitor-specific markers. For example, cell enrichment using surface antigens that define progenitor populations has been used to improve the yield of the desired cell types such as neural and cardiomyocyte progenitors (Dubois et al. (2011) *Nat Biotechnol* 29: 1011; Yuan et al. (2011) *PLoS One* 6: e17540). Progenitor surface markers could also be useful for monitoring and validating hPS differentiation and for high throughput screening of reagents that stimulate differentiation toward a given lineage. However, apart from mapped hematopoietic progenitor markers, there is a paucity of validated cell surface antigens for most embryonic progenitor cell lineages.

Phage display is a powerful ligand selection method that has been applied both in vitro and in vivo for the identification of cell-specific targeting peptides (Molek et al. (2011) *Molecules* 16: 857; Teesalu et al. (2012) *Methods Enzymol* 503: 35). Peptide libraries displayed on phage particles are selected by repeated rounds of enrichment for target binding phage. Displayed peptides, genetically expressed on phage coat proteins, are identified by sequencing recovered phage DNA. A distinct advantage of phage display is that it is a non-biased approach that does not require prior knowledge of the targeted cell surface receptor. However, selection against a mixed population of differentiated hPS cells is challenging because the cellular heterogeneity limits the abundance of each of the various cell type specific surface targets. Clonal expansion of cells derived from hPS cell differentiation could provide a more abundant source of progenitor cell surface targets for phage selection. Over 140 distinct clonal embryonic progenitor cell lines have been derived from hES cells using a combinatorial cell cloning approach (the ACTCellerate Initiative) that resulted in a diverse assortment of clonally pure, scalable cell lines that were selected under a variety of cell culture and differentiation conditions (West et al. (2008) *Regen Med* 3: 287). Characterization of these clonal progenitors could result in the identification of markers associated with progenitor cell types of specific organs and tissues allowing for both enrichment of specific progenitors from a mixed population of cells, as well as the monitoring of the development potential of these progenitor cells both in vivo and in vitro.

The instant invention addresses a variety of needs known in the art, including, but not limited to, the identification of markers associated with progenitor cell lines and the enrichment of progenitor cell types for use in research and clinical applications.

SUMMARY OF THE INVENTION

In certain embodiments the invention provides a method of enriching a population of progenitor cells, wherein the progenitor cell is the in vitro progeny of pluripotent stem cell, comprising contacting a population of cells comprising the progenitor cell with a peptide that binds specifically to the progenitor cell and separating the progenitor cell bound to the peptide from the population of cells thereby enriching for a population of progenitor cells.

In other embodiments the invention provides a method of enriching a population of mesoderm progenitor cells, wherein the mesoderm progenitor cell is the in vitro progeny of pluripotent stem cell, comprising contacting a population of cells comprising the mesoderm progenitor cell with a peptide that binds specifically to the mesoderm progenitor cell and separating the progenitor cell bound to the peptide from the population of cells thereby enriching for a population of mesoderm progenitor cells.

In yet other embodiments the invention provides a method of enriching a population of endoderm progenitor cells, wherein the endoderm progenitor cell is the in vitro progeny of pluripotent stem cell, comprising contacting a population of cells comprising the endoderm progenitor cell with a peptide that binds specifically to the endoderm progenitor cell and separating the progenitor cell bound to the peptide from the population of cells thereby enriching a population of endoderm progenitor cells thereby enriching for a population of endoderm progenitor cells.

In still other embodiments the invention provides a method of enriching a population of progenitor cells, wherein the progenitor cells are the in vitro progeny of pluripotent stem cell, comprising contacting a population of cells comprising the progenitor cells with a peptide chosen from a peptide comprising an amino acid sequence chosen from SWTYSYPNQNMD (SEQ ID NO: 1); DWTYSLPGLVEE (SEQ ID NO: 2); NWTWSMPTGNPA (SEQ ID NO: 3); GMTLRVLTN-YTE- (SEQ ID NO: 4); TLHVSENSWTYN (SEQ ID NO: 5); DWLWSFAPNVDT (SEQ ID NO: 6); TLSSQNPYMHKK (SEQ ID NO: 7); IDKQMMTSHKAI (SEQ ID NO: 8); QGMETQKLRMLK (SEQ ID NO: 9); GWYWETPLDMFN (SEQ ID NO: 10); GWVIDYDYYPMR (SEQ ID NO: 11); VTAENYQSFSVS (SEQ ID NO: 12); NNKMDDRMMMSIV (SEQ ID NO: 13); STGTDLHSNARI (SEQ ID NO: 14); YEFDNLLNRTLW (SEQ ID NO: 15); EWTVNERTMWDL (SEQ ID NO: 16) and separating the progenitor cell bound to the peptide comprising the amino acid sequence chosen from SWTYSYPNQNMD (SEQ ID NO: 1); DWTYSLPGLVEE (SEQ ID NO: 2); NWTWSMPTGNPA (SEQ ID NO: 3); GMTLRVLTN-YTE- (SEQ ID NO: 4); TLHVSENSWTYN (SEQ ID NO: 5); DWLWSFAPNVDT (SEQ ID NO: 6); TLSSQNPYMHKK (SEQ ID NO: 7); IDKQMMTSHKAI (SEQ ID NO: 8); QGMETQKLRMLK (SEQ ID NO: 9); GWYWETPLDMFN (SEQ ID NO: 10); GWVIDYDYYPMR (SEQ ID NO: 11); VTAENYQSFSVS (SEQ ID NO: 12); NNKMDDRMMMSIV (SEQ ID NO: 13); STGTDLHSNARI (SEQ ID NO: 14); YEFDNLLNRTLW (SEQ ID NO: 15); EWTVNERTMWDL (SEQ ID NO: 16) from the population of cells thereby enriching for the progenitor cells. The progenitor cell may be a mesoderm progenitor, or an endoderm progenitor, such as definitive endoderm progenitor for example.

In further embodiments the invention provides a method of enriching a population of cells comprising W10 progenitor cells comprising contacting a population of cells comprising the W10 progenitor cell with a peptide that binds to the W10 progenitor cell and separating the W10 progenitor cell bound to the peptide from the population of cells.

In further embodiments the invention provides a method of enriching a population of progenitor cells expressing one or more of the genes chosen from heart and neural crest derivatives-expressed 2 (HAND2), HOXA4 and HOXB7, wherein the progenitor cell expressing one or more of the genes chosen from heart and neural crest derivatives-expressed 2 (HAND2), HOXA4 and HOXB7 is the in vitro progeny of pluripotent stem cell, comprising contacting a population of cells comprising the progenitor cell expressing one or more of the genes chosen from heart and neural crest derivatives-expressed 2 (HAND2), HOXA4 and HOXB7 with a peptide that binds specifically to the progenitor cell expressing one or more of the genes chosen from heart and neural crest derivatives-expressed 2 (HAND2), HOXA4 and HOXB7 and separating the progenitor cell bound to the peptide from the population of cells thereby enriching a population of progenitor cells expressing one or more of the genes chosen from heart and neural crest derivatives-expressed 2 (HAND2), HOXA4 and HOXB7.

In some embodiments the invention provides a method of enriching a population of progenitor cells which expresses one or more genes expressed by a smooth muscle cell when cultured with TGFβ3, wherein the progenitor cell expressing one or more genes expressed by a smooth muscle cell when cultured with TGFβ3 is the in vitro progeny of a pluripotent stem cell, comprising contacting a population of cells comprising the progenitor cell expressing one or more genes expressed by a smooth muscle cell when cultured with TGFβ3 with a peptide that binds to the progenitor cell expressing one or more genes expressed by a smooth muscle cell when cultured with TGFβ3, and separating the progenitor cell bound to the peptide from the population of cells thereby enriching the population of cells expressing one or more genes expressed by a smooth muscle cell when cultured with TGFβ3.

In yet further embodiments the invention provides a method of enriching a population of progenitor cells, wherein the progenitor cell is the in vitro progeny of pluripotent stem cell, comprising contacting a population of cells comprising the progenitor cell with a peptide having PLEXIN homology that binds specifically to the progenitor cell and separating the progenitor cell bound to the peptide having PLEXIN homology from the population of cells thereby enriching for the population of progenitor cells. The peptide may be substantially homologous or completely homologous to PLEXIN.

In certain embodiments the invention provides a method separating a pluripotent stem cell from a population of cells comprising a pluripotent stem cell and a progenitor cell comprising contacting the population of cells comprising a pluripotent stem cells and a progenitor cell with a peptide that binds specifically to a progenitor cell and separating the progenitor cell bound to the peptide from the population of cells, thereby separating a pluripotent stem cell from a population of cells comprising a pluripotent stem cell and a progenitor cell.

In still other embodiments the invention provides a method of separating an ectoderm progenitor cell from a population of cells comprising ectoderm progenitor cells and either mesoderm progenitor cells, endoderm progenitor cells or both, wherein at least one of the ectoderm progenitor cells, the mesoderm progenitor cells and the endoderm progenitor cells are the in vitro progeny of a pluripotent stem cell, comprising contacting the population of cells comprising an ectoderm progenitor cell and mesoderm progenitor cells, endoderm progenitor cells or both with a peptide that does not bind to the ectoderm progenitor cell and separating the cells bound to the peptide from the cells that are not bound to the peptide thereby separating the ectoderm progenitor cells from the population of cells comprising either mesoderm progenitor cells, endoderm progenitor cells or both.

In certain embodiments the invention provides a peptide that binds specifically to a progenitor cell, wherein the progenitor cell is the in vitro progeny of a pluripotent stem cell.

In some embodiments the invention provides a peptide that binds specifically to an endoderm progenitor cell, wherein the progenitor cell is the in vitro progeny of a pluripotent stem cell.

In other embodiments the invention provides a peptide that binds specifically to a mesoderm progenitor cell, wherein the mesoderm progenitor cell is the in vitro progeny of a pluripotent stem cell.

In certain embodiments the invention provides a peptide that binds specifically to the progenitor cell W10.

In yet other embodiments the invention provides a peptide that binds specifically to progenitor cell expressing a protein found in smooth muscle cell progenitor, wherein the progenitor cell is the in vitro progeny of a pluripotent stem cell.

In still other embodiments the invention provides a peptide that binds specifically to a progenitor cell expressing a protein chosen from heart and neural crest derivatives-expressed 2 (HAND2), HOXA4 and HOXB7, wherein the progenitor cell is the in vitro progeny of a pluripotent stem cell.

In some embodiments the invention provides a peptide that binds specifically to progenitor cell expressing at least one gene found in endoderm cells, wherein the progenitor cell is the in vitro progeny of a pluripotent stem cell.

In certain embodiments the invention provides a peptide that binds specifically to a progenitor cell expressing at least one gene found in a mesoderm cell, wherein the progenitor cell is the in vitro progeny of a pluripotent stem cell.

In further embodiments the invention provides a peptide that does not bind specifically to an ectoderm progenitor cell.

In other embodiments the invention provides a peptide that binds specifically to a progenitor cell, but does not bind to a pluripotent stem cell, wherein the progenitor cell is the in vitro progeny of a pluripotent stem cell.

In still further embodiments the invention provides a progenitor cell binding peptide chosen from the amino acid sequence SWTYSYPNQNMD (SEQ ID NO: 1); DWTYSLPGLVEE (SEQ ID NO: 2); NWTWSMPTGNPA (SEQ ID NO: 3); GMTLRVLTN-YTE- (SEQ ID NO: 4); TLHVSENSWTYN (SEQ ID NO: 5); DWLWSFAPNVDT (SEQ ID NO: 6); TLSSQNPYMHKK (SEQ ID NO: 7); IDKQMMTSHKAI (SEQ ID NO: 8); QGMETQKLRMLK (SEQ ID NO: 9); GWYWETPLDMFN (SEQ ID NO: 10); GWVIDYDYYPMR (SEQ ID NO: 11); VTAENYQSFSVS (SEQ ID NO: 12); NNKMDDRMMMSIV (SEQ ID NO: 13); STGTDLHSNARI (SEQ ID NO: 14); YEFDNLLNRTLW (SEQ ID NO: 15); EWTVNERTMWDL (SEQ ID NO: 16).

In still other embodiments the invention provides a progenitor cell binding peptide wherein the progenitor cell binding peptide comprises PLEXIN homology and wherein the progenitor cell is the in vitro progeny of a pluripotent stem cell. The peptide may be substantially homologous or completely homologous to PLEXIN.

In other embodiments the invention provides a composition comprising a progenitor cell and a peptide specifically bound to the progenitor cell, wherein the progenitor cell is the in vitro progeny of a pluripotent stem cell.

In still other embodiments the invention provides a composition comprising an endoderm progenitor cell and a peptide bound specifically to the endoderm progenitor cell, wherein the progenitor cell is the in vitro progeny of a pluripotent stem cell.

In further embodiments the invention provides a composition comprising a mesoderm progenitor cell and a peptide bound to the mesoderm progenitor cell, wherein the progenitor cell is the in vitro progeny of a pluripotent stem cell.

In yet other embodiments the invention provides a composition comprising a smooth muscle progenitor cell and a peptide bound specifically to the smooth muscle progenitor cell, wherein the progenitor cell is the in vitro progeny of a pluripotent stem cell.

In still other embodiments the invention provides a composition comprising the W10 progenitor cell and a peptide specifically bound to the W10 progenitor cell.

In some embodiments the invention provides a progenitor cell expressing a protein chosen from heart and neural crest derivatives-expressed 2 (HAND2), HOXA4 and HOXB7 and a peptide bound specifically to the progenitor cell expressing a protein chosen from heart and neural crest derivatives-expressed 2 (HAND2), HOXA4 and HOXB7, wherein the progenitor cell is the in vitro progeny of a pluripotent stem cell.

In still further embodiments the invention provides a composition comprising a progenitor cell and a peptide bound specifically to the progenitor cell, wherein the peptide is chosen from a peptide having the amino acid sequence SWTYSYPNQNMD (SEQ ID NO: 1); DWTYSLPGLVEE (SEQ ID NO: 2); NWTWSMPTGNPA (SEQ ID NO: 3); GMTLRVLTN-YTE- (SEQ ID NO: 4); TLHVSENSWTYN (SEQ ID NO: 5); DWLWSFAPNVDT (SEQ ID NO: 6); TLSSQNPYMHKK (SEQ ID NO: 7); IDKQMMTSHKAI (SEQ ID NO: 8); QGMETQKLRMLK (SEQ ID NO: 9); GWYWETPLDMFN (SEQ ID NO: 10); GWVIDYDYYPMR (SEQ ID NO: 11); VTAENYQSFSVS (SEQ ID NO: 12); NNKMDDRMMMSIV (SEQ ID NO: 13); STGTDLHSNARI (SEQ ID NO: 14); YEFDNLLNRTLW (SEQ ID NO: 15); EWTVNERTMWDL (SEQ ID NO: 16), wherein the progenitor cell is the in vitro progeny of a pluripotent stem cell.

In yet other embodiments the invention provides a composition comprising a progenitor cell and a peptide bound specifically to the progenitor cell, wherein the peptide bound specifically to the progenitor cell comprises PLEXIN homology, wherein the progenitor cell is the in vitro progeny of a pluripotent stem cell. The peptide may be substantially homologous or completely homologous to PLEXIN.

In further embodiments the invention provides a method of detecting a progenitor cell comprising contacting the progenitor cell with a peptide that binds the progenitor cell specifically, wherein the peptide comprises a detectable substance, thereby detecting the progenitor cell. The progenitor cell may be detected in vitro or in vivo.

In still other embodiments the invention provides a method of detecting a mesoderm progenitor cell comprising contacting the mesoderm progenitor cell with a peptide that binds specifically to the mesoderm progenitor cell, wherein the peptide comprises a detectable substance, thereby detecting the progenitor cell. The progenitor cell may be detected in vitro or in vivo.

In other embodiments the invention provides a method of detecting an endoderm progenitor cell comprising contacting the endoderm progenitor cell with a peptide that binds specifically to the endoderm progenitor cell, wherein the peptide comprises a detectable substance, thereby detecting the progenitor cell. The progenitor cell may be detected in vitro or in vivo.

In still other embodiments the invention provides a method of detecting a smooth muscle progenitor cell comprising contacting the smooth muscle progenitor cell with a peptide that binds specifically to the smooth muscle progenitor cell, wherein the peptide comprises a detectable substance, thereby detecting the progenitor cell. The progenitor cell may be detected in vitro or in vivo.

In yet other embodiments the invention provides a method of detecting a W10 progenitor cell comprising contacting the W10 progenitor cell with a peptide that binds specifically to the W10 progenitor cell, wherein the peptide comprises a detectable substance, thereby detecting the progenitor cell. The progenitor cell may be detected in vitro or in vivo.

In further embodiments the invention provides a method of detecting a progenitor cell comprising contacting the progenitor cell with a peptide that binds the progenitor cell specifically, wherein the peptide is chosen from a peptide having the amino acid sequence SWTYSYPNQNMD (SEQ ID NO: 1); DWTYSLPGLVEE (SEQ ID NO: 2); NWTWSMPTGNPA (SEQ ID NO: 3); GMTLRVLTN-YTE- (SEQ ID NO: 4); TLHVSENSWTYN (SEQ ID NO: 5); DWLWSFAPNVDT (SEQ ID NO: 6); TLSSQNPYMHKK (SEQ ID NO: 7); IDKQMMTSHKAI (SEQ ID NO: 8); QGMETQKLRMLK (SEQ ID NO: 9); GWYWETPLDMFN (SEQ ID NO: 10); GWVIDYDYYPMR (SEQ ID NO: 11); VTAENYQSFSVS (SEQ ID NO: 12); NNKMDDRMMMSIV (SEQ ID NO: 13); STGTDLHSNARI (SEQ ID NO: 14); YEFDNLLNRTLW (SEQ ID NO: 15); EWTVNERTMWDL (SEQ ID NO: 16) and wherein the peptide comprises a detectable substance, thereby detecting the progenitor cell. The progenitor cell may be detected in vitro or in vivo.

In further embodiments the invention provides a method of detecting a progenitor cell expressing a protein chosen from heart and neural crest derivatives-expressed 2 (HAND2), HOXA4 and HOXB7 comprising contacting the progenitor cell expressing a protein chosen from heart and neural crest derivatives-expressed 2 (HAND2), HOXA4 and HOXB7 with a peptide that binds specifically to the progenitor cell expressing a protein chosen from heart and neural crest derivatives-expressed 2 (HAND2), HOXA4 and HOXB7, wherein the peptide comprises a detectable substance, thereby detecting the progenitor cell. The progenitor cell may be detected in vitro or in vivo.

In yet other embodiments the invention provides a method of detecting a progenitor cell comprising contacting the progenitor cell with a peptide having PLEXIN homology and that binds specifically to the progenitor cell, wherein the peptide comprises a detectable substance, thereby detecting the progenitor cell. The progenitor cell may be detected in vitro or in vivo. The peptide may be substantially homologous or completely homologous to PLEXIN In certain embodiments the invention provides a method of monitoring the differentiation of a progenitor cell comprising 1) contacting the progenitor cell with a peptide that binds to the progenitor cell, wherein the peptide that binds to the progenitor cell comprises a detectable substance and 2) monitoring the progenitor cell bound to the peptide over time thereby monitoring the differentiation of a progenitor cell. The cell may be monitored in vivo or in vitro.

In further embodiments the invention provides a method of monitoring the differentiation of an endoderm progenitor cell comprising 1) contacting the endoderm progenitor cell with a peptide that binds specifically to the endoderm progenitor cell, wherein the peptide that binds specifically to the endoderm progenitor cell comprises a detectable substance and 2) monitoring the progenitor cell bound to the peptide over time thereby monitoring the differentiation of an endoderm progenitor cell. The cell may be monitored in vivo or in vitro.

In still further embodiments the invention provides a method of monitoring the differentiation of an mesoderm progenitor cell comprising 1) contacting the mesoderm progenitor cell with a peptide that binds specifically to the mesoderm progenitor cell, wherein the peptide that binds specifically to the mesoderm progenitor cell comprises a detectable substance and 2) monitoring the progenitor cell bound to the peptide over time thereby monitoring the differentiation of a mesoderm progenitor cell. The cell may be monitored in vivo or in vitro.

In still other embodiments the invention provides a method of monitoring the differentiation of a smooth muscle progenitor cell comprising 1) contacting the smooth muscle progenitor cell with a peptide that binds specifically to the smooth muscle progenitor cell, wherein the peptide that binds specifically to the smooth muscle progenitor cell comprises a detectable substance and 2) monitoring the progenitor cell bound to the peptide over time thereby monitoring the differentiation of a progenitor cell. The cell may be monitored in vivo or in vitro.

In further embodiments the invention provides a method of monitoring the differentiation of a W10 cell comprising contacting the W10 cell with a peptide that binds specifically to the W10 cell, wherein the peptide that binds specifically to the W10 cell comprises a detectable substance and monitoring the progenitor cell bound to the peptide over time thereby monitoring the differentiation of a progenitor cell. The cell may be monitored in vivo or in vitro.

In certain embodiments the invention provides a method of monitoring the differentiation of a progenitor cell expressing a protein chosen from heart and neural crest derivatives-expressed 2 (HAND2), HOXA4 and HOXB7 comprising 1) contacting the progenitor cell expressing a protein chosen from heart and neural crest derivatives-expressed 2 (HAND2), HOXA4 and HOXB7 with a peptide that binds to the progenitor cell expressing a protein chosen from heart and neural crest derivatives-expressed 2 (HAND2), HOXA4 and HOXB7, wherein the peptide that binds to the progenitor cell comprises a detectable substance and monitoring the progenitor cell bound to the peptide over time thereby monitoring the differentiation of a progenitor cell. The cell may be monitored in vivo or in vitro.

In some embodiments the invention provides a method of monitoring the differentiation of a progenitor cell comprising 1) contacting the progenitor cell with a peptide that binds to the progenitor cell, wherein the peptide is chosen from a peptide having the amino acid sequence SWTYSYPNQNMD (SEQ ID NO: 1); DWTYSLPGLVEE (SEQ ID NO: 2); NWTWSMPTGNPA (SEQ ID NO: 3); GMTLRVLTNYTE- (SEQ ID NO: 4); TLHVSENSWTYN (SEQ ID NO: 5); DWLWSFAPNVDT (SEQ ID NO: 6); TLSSQNPYMHKK (SEQ ID NO: 7); IDKQMMTSHKAI (SEQ ID NO: 8); QGMETQKLRMLK (SEQ ID NO: 9); GWYWETPLDMFN (SEQ ID NO: 10); GWVIDYDYYPMR (SEQ ID NO: 11); VTAENYQSFSVS (SEQ ID NO: 12); NNKMDDRMMMSIV (SEQ ID NO: 13); STGTDLHSNARI (SEQ ID NO: 14); YEFDNLLNRTLW (SEQ ID NO: 15); EWTVNERTMWDL (SEQ ID NO: 16) and wherein the peptide that binds to the progenitor cell comprises a detectable substance and 2) monitoring the progenitor cell bound to the peptide over time thereby monitoring the differentiation of a progenitor cell. The cell may be monitored in vivo or in vitro.

In still other embodiments the invention provides a kit comprising one or more peptides that bind specifically to a progenitor cell, wherein the progenitor cell is the in vitro progeny of a pluripotent stem cell.

DESCRIPTION OF DRAWINGS

For a fuller understanding of the nature and advantages of the present invention, reference should be had to the following detailed description taken in connection with the accompanying drawings, in which:

FIG. 1A: Undifferentiated (day 0) and differentiated W10 micromass (MM) cultures in the presence of 10 ng/ml TGFβ3 (day 14). Cells were stained with anti-MYH11 antibody and DAPI. FIG. 1B: W10 cells express smooth muscle marker, MYH11, but not cartilage marker COL2A1 upon 14 day MM differentiation (as in A). Mean expression of the MYH11 and COL2A1 by Illumina microarray of day 0 undifferentiated control and day 14 differentiated MM cultures of coronary artery smooth muscle cell (CASMC), W10, and the chondrogenic cell line, 4D20.8. Values are from duplicate (CASMC) and triplicate (W10 and 4D20.8) experiments.

FIG. 2A through FIG. 2D. Selection of a peptide phage display library against W10 progenitor cells. FIG. 2A: Peptide phages that bind to W10 progenitor cell line were enriched by 3 rounds of biopanning PhD-12 phage display peptide library ($2 \times 10^{11}$ pfu, for round 1) or amplified recovered phage ($2 \times 10^{10}$ pfu, for rounds 2 and 3) were first adsorbed against human adult dermal fibroblasts cells and then incubated with adherent W10 cells. The phage were recovered from the cell lysate and sample phage clones were sequenced. The enriched library was amplified for further rounds of selection. FIG. 2B: The percentage of input phage recovered increased with each round of selection. The percentage of input phage recovered was determined by titration of plaque forming units (pfu) in the cell lysate relative to the input pfu used for each panning round. FIG. 2C: Frequency and multiple sequence alignment of peptides identified as candidate peptide phage in rounds 2 and 3 of panning generated by CLUSTAL W (2.10). FIG. 2D: Phylogram based on FIG. 2C denoting peptide similarities.

FIG. 3A: Immunofluorescent detection of bound phages. Cells were incubated with $2 \times 10^{10}$ phage particles for 2 h at 37° C.; unbound phages were removed by washing and cells were fixed and permeabilized. Bound phages were detected by immunocytochemistry using rabbit anti-phage antibody and Alexa568-conjugated goat anti-rabbit antibody. Cell nuclei were stained using DAPI. FIG. 3B: Quantitation of peptide phage cell binding. $2 \times 10^{10}$ pfu of each candidate or controls (RGD, Gly12 and empty phage M13KE) phages were assessed for binding on $1 \times 10^5$ W10 progenitor cells for 2 h at 37° C. Cell associated phages were recovered from cell lysates and quantified by titration. Protein in cell lysates was measured by microBCA assay. The relative binding factor (BF) is calculated as peptide phage recovery (percentage of input) relative to M13KE control phage recovery (percentage of input). Values are from triplicate experiments and shown as mean+/−standard error. BFs for the 4 W10 peptide phage were statistically significant from the control M13KE phage (ANOVA with Dunnett's multiple comparison tests; p values: *: 0.05 and **: 0.01). BFs for RGD and Gly12 were not statistically significant.

FIG. 4A: Immunofluorescent detection of bound peptide phages. Chemically synthesized peptides were added to compete with binding of peptide phages to W10 progenitor cells. Cells were pre-incubated with different peptides at 100 μM or without peptide for 30 min at 4° C., followed by peptide phages ($2 \times 10^{10}$ pfu) for an additional 1 h at 4° C. After washing, the bound peptide phages were detected by immunofluorescence. Peptide sequences are: W10 R2 11 biotin: GWVIDYDYYPM-RGGGK (biotin) (SEQ ID NO: 17); FITC W10 R2 11: FITC GWVIDYDYYPMRGGG (SEQ ID NO: 18) and FITC-unrelated: FITC NHVHRMHATPAY (SEQ ID NO: 19). FIG. 4B: Percentage of input phage recovered from cell lysate. Cells were pre-incubated with peptides at 5 μM or 5 nM, or without peptide for 30 min at 4° C., followed by peptide phages ($2 \times 10^{10}$ pfu) for an additional 1 h at 4° C. After washing, the recovered phage was quantified by titration. The competition is shown as percentage of no-peptide control. Values are from triplicate experiments shown as mean+/−standard error. Competition by the corresponding free peptide was statistically significant at 5 nM and 5 μM with the exception of W10-R2-21 (only significant at 5 μM). Competition by scrambled or unrelated peptide was not statistically significant. (ANOVA with Dunnett's multiple comparison tests; p values: *: 0.05. : 0.01 and *: 0.001). Peptide sequences are: peptide: X12GGGK (biotin)(SEQ ID NO: 74); unrelated: biotin NHVHRMHATPAY(SEQ ID NO: 19); W10 R2 11 scrambled: DYWDVGPI-YRMYGGGG (SEQ ID NO: 75); W10 R2 21 scrambled: LGTMDWFWPYNEGGGG (SEQ ID NO: 20); W10-R3-18-scrambled: VSDPFDNLWTAWGGGK (SEQ ID NO: 21).

FIG. 5A: Cell targeting by fluorescent Qdots. Qdot605 ITK SA were complexed with an excess of chemically synthesized C-terminal biotinylated peptide; unbound peptide was removed by dialysis. W10 progenitor cells were incubated for 16 h at 37° C. with 5 nM of Qdot complexes, washed and imaged using a fluorescence microscope. FIG. 5B: Competition with free peptide or peptide-targeted Qdots. Cells were pre-incubated with 5 nM peptide, peptide targeted Qdots, or untargeted Qdots, for 30 min at 4° C., followed by addition of peptide phage ($2 \times 10^{10}$ pfu) for an additional 1 h at 4° C. After washing, the recovered phage was quantified by titration. The competition is shown as percentage of no-peptide control. Values are from triplicate experiments and shown as mean+/−standard error. Competition by corresponding free peptide or peptide-Qdot complex at 5 nM was statistically significant. Competition by uncoupled Qdots was not statistically significant (ANOVA with Dunnett's multiple comparison tests; p values: *: 0.05. : 0.01 and *: 0.001). FIG. 5C: Flow cytometry analysis. Cells were labeled as in (A), dissociated from the tissue culture plate using TrypLE, resuspended in PBS and analyzed in LSRFortessa flow cytometer. 10,000 events were recorded for each sample; cells were excited using the 405 nm laser and fluorescence emission was detected with the 605/12 bandpass filter. Cells labeled with W10 R3 18 peptide-Qdot complexes (green) showed higher mean fluorescent intensity than cells labeled with untargeted Qdots (red) or unlabeled W10 cells (blue).

FIG. 7A: Selective peptide targeting of human embryonic stem cells (H9) that were differentiated into the three germ layers (see methods for protocols) for 6-8 days compared to undifferentiated control. Differentiated cells were incubated for 16 h at 37° C. with 5 nM of Qdot complexes, washed and imaged using a fluorescence microscope. Representative bright-field and fluorescent signal of W10 peptide Qdot complexes (red) are shown. FIG. 7B: Cells were stained with the following differentiation markers to verify the germ layer commitment: nestin for ectoderm, α-actinin for mesoderm, SOX17 for endoderm conditions and OCT3/4 for undifferentiated cells.

FIG. 8A: Fluorescence microscopy images of confluent embryonic progenitor cell lines 4D20.8 and 7PEND24 labeled with W10-peptide Qdot complexes, showing only signal from Qdot655 channel only and corresponding overlap histograms of flow cytometric quantification of the same labeled cell lines. FIG. 8B: Fluorescence microscopy images of confluent embryonic progenitor cell lines E15 and J16 labeled with W10-peptide Qdot complexes, showing only signal from Qdot655 channel only and corresponding overlap histograms of flow cytometric quantification of the same labeled cell lines. FIG. 8C: Fluorescence microscopy images of confluent embryonic progenitor cell lines J8 and MW1 labeled with W10-peptide Qdot complexes, showing only signal from Qdot655 channel only and corresponding overlap histograms of flow cytometric quantification of the same labeled cell lines. FIG. 8D: Fluorescence microscopy images of confluent embryonic progenitor cell lines SM30 and U31 labeled with W10-peptide Qdot complexes, showing only signal from Qdot655 channel only and corresponding overlap histograms of flow cytometric quantification of the same labeled cell lines. FIG. 8E: Fluorescence microscopy images of confluent embryonic progenitor cell lines W10 and Z11 labeled with W10-peptide Qdot complexes, showing only signal from Qdot655 channel only and corresponding overlap histograms of flow cytometric quantification of the same labeled cell lines. W10 peptide Qdot complex is shown in red while control samples of uncoupled Qdots and unstained cells are shown in black and grey, respectively. Results are representative of three independent experiments.

FIG. 9A through FIG. 9C. Differentiation of W10 cell line. Gene expression analysis of cultured coronary artery smooth muscle, W10, and 4D20.8 cells in the undifferentiated state and micromass (MM) differentiation conditions. FIG. 9A and FIG. 9B: Comparative microarray relative fluorescence units (RFU) values for coronary artery smooth muscle cells, W10, and 4D20.8 in control conditions of five-day quiescence and 14 days of micromass culture. FIG. 9C: Values from selected genes are compiled from data in FIG. 9A and FIG. 9B, and the corresponding graphs showed the upregulation of smooth muscle heavy chain 11 (MYH11), calponin 1 (CNN1), myosin light chain kinase (MYLK), and smooth muscle actin (ACTA2) in W10 and CASMC cells but not in 4D20.8 cells under myodifferentiation conditions.

FIG. 10A through FIG. 10C. Analysis of binding W10 peptide phage sequences. FIG. 10A: Best score hit for homologous protein sequences were identified in the Homo sapiens RefSeq protein database using Blastp (PSI-Blast, position-specific iterated BLAST with word size of 3 and Blosum62 matrix, available online at: blast.ncbi.nlm.nih-.gov). FIG. 10B: Sequence homology of the W10 binding peptides with plexins and semaphorin. Identical amino acids are in bold, highly similar are grey. FIG. 10C lists the SEQ ID NOS of the sequences provided in FIG. 10A and FIG. 10B.

DETAILED DESCRIPTION

Figure 1A:
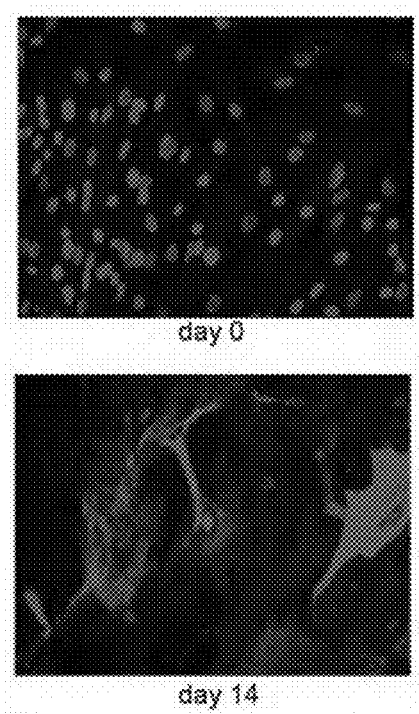
FIG. 1A and FIG. 1B. W10 is a progenitor cell line capable of smooth muscle differentiation.

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of the present disclosure, the suitable methods, devices, and materials are now described. Nothing herein is to be construed as an admission that the invention is not entitled to antedate such disclosure by virtue of prior invention.

Previous studies have shown that phage display is useful for identifying peptides that target undifferentiated (Lu et al. (2010) PLoS One 5: e12075; Zhao et al. (2010) *J Biomol Screen* 15: 687; Zhao et al. (2010) *Peptides* 31: 2027), differentiated cells (Zhao et al. (2010) *J Biomol Screen* 15: 687) or cancer cell lines (Rasmussen et al. (2002) *Cancer Gene Ther* 9: 606; Spear et al. (2001) *Cancer Gene Ther* 8: 506). We describe here a novel phage display strategy that uses selection against a clonally pure pluripotent stem cell derivative to identify peptides that selectively target early human pluripotent stem (hPS) cell derived progenitor cell populations. The peptides developed here clearly bind to one or more developmentally regulated surface markers that are absent on undifferentiated pluripotent stem cells but are detected predominantly on definitive endodermal progenitors derived from 6-8 day differentiating hPS cells. Peptide targeting to definitive endoderm was unexpected given that the peptides were selected on the W10 cell line which expresses smooth muscle and other mesodermal markers (West et al. (2008) *Regen Med* 3: 287). However, the targets for the cell binding peptides although restricted may be present on more than one progenitor cell type. Analysis of 10 ACTCellerate cell lines revealed highly prevalent peptide binding to multiple distinct progenitor cell lines.

Cellular heterogeneity in hPS derived cell populations is a major bottleneck for the successful development of hPS derived cells for transplantation. Contamination of differentiated cells with residual pluripotent cells is of particular concern for safety because of their ability to form teratomas in vivo (Blum, Benvenisty (2009) *Cell Cycle* 8: 3822). Cell purity is also important for consistency of non-clinical applications such as disease modeling, drug screening and drug safety testing. We have begun to address this issue by developing targeting peptides that can identify subsets of progenitor cell types for use in cell enrichment and cell exclusion procedures. The advantage of such cell enrichment steps is clearly demonstrated by over a decade of the clinical application of cell surface targeted enrichment of hematopoietic stem cells for stem cell transplants as a cancer treatment (Grutzkau, Radbruch (2010) *Cytometry A* 77: 643). We isolated human progenitor stem cell targeting peptides that recognize certain hPS derived progenitor stem cell lines as well as hPS derived early definitive endoderm. The endodermal progenitor targeting peptides might be useful for enriching or excluding endodermal progenitors during directed differentiation. The peptide targeted Qdots could also be used to rapidly assess hPS cell differentiation capacity and to screen for reagents that direct differentiation toward definitive endoderm. Identification of additional progenitor stem cell targeting peptides using the approach described here may make it possible to improve recovery of clinically relevant progenitor cell types. This would be particularly useful for deriving patient-specific progenitors from the patient's own reprogrammed iPS cells. For example, a recent preclinical study of one of the ACTCellerate clonal cell lines, 4D20.8, has demonstrated the ability of this cell line to differentiate to chondrocytes capable of cartilage repair in a rat knee model (Sternberg et al. (2012) *Regen Med* 7: 481). It may be feasible to use the phage display approach described here to isolate stem cell targeting peptides that would facilitate retrieval of the equivalent cells from patient derived iPS cells to provide a source of genetically matched stem cells for cell replacement therapy.

In certain embodiments the invention provides peptides that bind specifically to progenitor cells that have been differentiated in vitro, and thus are the in vitro progeny of pluripotent stem cells. The peptides may be used to enrich for, or deplete the target progenitor cell to which it binds. The peptides may be used to visualize and/or monitor the progenitor cell as it differentiates further down a specific developmental pathway. The peptides may be used to identify and or characterize progenitor cell lines. For example the peptides can be used to identify one or more proteins expressed on the surface of a progenitor cell. The peptides may be used to block other agents, such as proteins, small molecules, drugs, and the like from binding to the cell surface of the progenitor cell.

Definitions

As used herein, the singular forms "a," "an," and "the" include plural reference unless the context clearly dictates otherwise. Thus, for example, reference to a "therapeutic" is a reference to one or more therapeutics and equivalents thereof known to those skilled in the art, and so forth.

As used herein, the term "about" means plus or minus 5% of the numerical value of the number with which it is being used. Therefore, about 50% means in the range of 45% to 55%.

The term "animal," "patient" or "subject" as used herein includes, but is not limited to, humans, non-human primates and non-human vertebrates such as wild, domestic and farm animals including any mammal, such as cats, dogs, cows, sheep, pigs, horses, rabbits, rodents such as mice and rats. In some embodiments, the term "subject," "patient" or "animal" refers to a male. In some embodiments, the term "subject," "patient" or "animal" refers to a female.

The term "antibody", as used herein, means an immunoglobulin or a part thereof, and encompasses any polypeptide comprising an antigen-binding site regardless of the source, method of production, or other characteristics. The term includes for example, polyclonal, monoclonal, monospecific, polyspecific, humanized, single-chain, chimeric, synthetic, recombinant, hybrid, mutated, and CDR-grafted antibodies. A part of an antibody can include any fragment which can bind antigen, for example, an Fab, F (ab')$_2$, Fv, scFv.

The term "ectoderm" as used herein, refers to the most exterior (or distal) layer of the developing embryo. The ectoderm differentiates to form the nervous system (spine, peripheral nerves and brain), tooth enamel and the epidermis (the outer part of integument). It also forms the lining of mouth, anus, nostrils, sweat glands, hair and nails. In vertebrates, the ectoderm has three parts: external ectoderm (also known as surface ectoderm), the neural crest, and neural tube. The latter two are known as neuroectoderm.

The term "endoderm," as used herein, refers to the innermost germ layer of the early embryo. It gives rise to the entire alimentary canal except part of the mouth, pharynx and the terminal part of the rectum (which are lined by involutions of the ectoderm), the lining cells of all the glands which open into the digestive tube, including those of the liver and pancreas; the trachea, bronchi, and alveoli of the lungs; the lining of the follicles of the thyroid gland and thymus; the epithelium of the auditory tube and tympanic cavity; the urinary bladder and part of the urethra.

The term "gene expression result" refers to a qualitative and/or quantitative result regarding the expression of a gene or gene product. Any method known in the art may be used to quantitate a gene expression result. The gene expression result can be an amount or copy number of the gene, the RNA encoded by the gene, the mRNA encoded by the gene, the protein product encoded by the gene, or any combination thereof. The gene expression result can also be normalized or compared to a standard. The gene expression result can be used, for example, to determine if a gene is expressed, overexpressed, or differentially expressed in two or more samples by comparing the gene expression results from 2 or more samples or one or more samples with a standard or a control.

The term "homology," as used herein, refers to a degree of complementarity. There may be partial homology or complete homology. The word "identity" may substitute for the word "homology." A partially complementary nucleic acid sequence that at least partially inhibits an identical sequence from hybridizing to a target nucleic acid is referred to as "substantially homologous." The inhibition of hybridization of the completely complementary nucleic acid sequence to the target sequence may be examined using a hybridization assay (Southern or northern blot, solution hybridization, and the like) under conditions of reduced stringency. A substantially homologous sequence or hybridization probe will compete for and inhibit the binding of a completely homologous sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% homology or identity). In the absence of non-specific binding, the substantially homologous sequence or probe will not hybridize to the second non-complementary target sequence.

As used herein, the term "hybridization" or "hybridizing" refers to hydrogen bonding, which may be Watson-Crick, Hoogsteen or reversed Hoogsteen hydrogen bonding between complementary nucleoside or nucleotide bases. For example, adenine and thymine are complementary nucleobases which pair through the formation of hydrogen bonds. "Complementary," as used herein in reference to nucleic acid molecules refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that a nucleic acid sequence need not be 100% complementary to that of its target nucleic acid to be specifically hybridizable. A nucleic acid compound is specifically hybridizable when there is binding of the molecule to the target, and there is a sufficient degree of complementarity to avoid non-specific binding of the molecule to non-target sequences under conditions in which specific binding is desired, i.e., under physiological conditions in the case of in vivo assays or therapeutic treatment, and in the case of in vitro assays, under conditions in which the assays are performed.

The term "induced pluripotent stem cell," (iPS) as used herein, refers to a pluripotent cell obtained by manipulating (in vitro) a non-pluripotent cell, such as a somatic cell, so that it reverts back to a pluripotent state similar to the pluripotent state seen in embryonic stem cells.

The term "label" and/or "detectible substance" refers to a composition capable of producing a detectable signal indicative of the presence of the target polynucleotide or a polypeptide or protein in an assay sample. Suitable labels include radioisotopes, nucleotide chromophores, enzymes, substrates, fluorescent molecules, chemiluminescent moieties, magnetic particles, bioluminescent moieties, and the like. As such, a label is any composition detectable by a device or method, such as, but not limited to, a spectroscopic, photochemical, biochemical, immunochemical, electrical, optical, chemical detection device or any other appropriate device. In some embodiments, the label may be detectable visually without the aid of a device. The term "label" or "detectable substance" is used to refer to any chemical group or moiety having a detectable physical property or any compound capable of causing a chemical group or moiety to exhibit a detectable physical property, such as an enzyme that catalyzes conversion of a substrate into a detectable product. The term "label" or "detectable substance" also encompasses compounds that inhibit the expression of a particular physical property. The label may also be a compound that is a member of a binding pair, the other member of which bears a detectable physical property.

The term "multipotent cell," as used herein, refers to a cell that can differentiate into a plurality of cell types, but which cannot differentiate into one or more cells found in each of the three germ layers: endoderm, ectoderm, mesoderm. It is generally more developmentally advanced or mature compared to a pluripotent stem cell.

The term "mesoderm" as used herein, refers to the germ layer that forms many muscles, the heart, the circulatory and excretory systems, and the dermis, skeleton, and other supportive and connective tissue. It also gives rise to the notochord, a supporting structure between the neural canal and the primitive gut. In many animals, including vertebrates, the mesoderm surrounds a cavity known as the coelom, the space that contains the viscera.

The use of "nucleic acid," "polynucleotide" or "oligonucleotide" or equivalents herein means at least two nucleotides covalently linked together. In some embodiments, an oligonucleotide is an oligomer of 6, 8, 10, 12, 20, 30 or up to 100 nucleotides. In some embodiments, an oligonucleotide is an oligomer of at least 6, 8, 10, 12, 20, 30, 40, 50, 60, 70, 80, 90, 100, 150, 200, 300, 400, or 500 nucleotides. A "polynucleotide" or "oligonucleotide" may comprise DNA, RNA, PNA or a polymer of nucleotides linked by phosphodiester and/or any alternate bonds.

As used herein, the term "optional" or "optionally" refers to embodiments where the subsequently described structure, event or circumstance may or may not occur, and that the description includes instances where the event occurs and instances where it does not.

The term "passage" and "passaged," as used herein, refers to splitting a growing replicating cell culture that has reached a desired cell density (e.g. confluency or 80% confluency for an adherent cell line) into a fractional a fractional component such as ½, ⅓ or the like, in order to allow the cells to continue to replicate.

The term "peptide" as used herein, refers to a series of amino acids linked by peptide bonds. In some instances, a peptide may comprise a portion of a full length protein.

The phrases "percent homology," "% homology," "percent identity," or "% identity" refer to the percentage of sequence similarity found in a comparison of two or more amino acid or nucleic acid sequences. Percent identity can be determined electronically, e.g., by using the MEGALIGN program (LASERGENE software package, DNASTAR). The MEGALIGN program can create alignments between two or more sequences according to different methods, e.g., the Clustal Method. (Higgins, D. G. and P. M. Sharp (1988) *Gene* 73:237-244.) The Clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no homology between the two amino acid sequences are not included in determining percentage similarity. Percent identity between nucleic acid sequences can also be calculated by the Clustal Method, or by other methods known in the art, such as the Jotun Hein Method. (See, e.g., Hein, J. (1990) *Methods Enzymol.* 183:626-645.) Identity between sequences can also be determined by other methods known in the art, e.g., by varying hybridization conditions.

"Pluripotent stem cell," as used herein, refers to a cell that has the ability, when cultured under the appropriate conditions to differentiate into a least one cell type from the three embryonic germ layers: ectoderm, endoderm and mesoderm. Examples of pluripotent stem cells, include, but are not limited to, embryonic stem cells, such as established embryonic stem cell lines, and induced pluripotent stem cells.

"Progenitor cells," as used herein, refers to a cell that is no longer a pluripotent stem cell in that it has differentiated beyond the pluripotent state, but retains the ability to differentiate further, for example, into a cell type that expresses at least one gene found in an adult organism, such as a mammal. Examples of progenitor cells include the W10 cell line, the 4D20.8 cell line, the SM30 cell line, the 7PEND24 cell line, and the E15 cell line.

"Progeny of a pluripotent stem cell," as used herein, refers to one or more daughter cells obtained from a parental pluripotent stem cell. Included within this definition are instances where the progeny is a differentiated cell that is no longer a pluripotent stem cell. Examples of progeny of a pluripotent stem cell may include progenitor cells which are no longer pluripotent, but are still multipotent, as well as cells that have fully differentiated into a mature phenotype. Non-pluripotent progeny of pluripotent stem cells are sometimes referred to herein as "differentiated progeny of pluripotent stem cells." The progeny of a pluripotent stem cell may be obtained in vitro, i.e. by growing the cells under suitable culture conditions, or in vivo, i.e. by transplanting the cells into a subject.

"Recombinant protein," as used herein, means a protein made using recombinant techniques, for example, but not limited to, through the expression of a recombinant nucleic acid as depicted infra. A recombinant protein may be distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises about 50-75%, about 80%, or about 90%. In some embodiments, a substantially pure protein comprises about 80-99%, 85-99%, 90-99%, 95-99%, or 97-99% by weight of the total protein. A recombinant protein can also include the production of a protein from one organism (e.g. human) in a different organism (e.g. yeast, *E. coli*, or the like) or host cell. Alternatively, the protein may be made at a significantly higher concentration than is normally seen, through the use of an inducible promoter or high expression promoter, such that the protein is made at increased concentration levels. Alternatively, the protein may be in a form not normally found in nature, as in the addition of an epitope tag or amino acid substitutions, insertions and deletions, as discussed herein.

As used herein, the term "specifically binds" or "specifically binding" means binding that is measurably different from a non-specific interaction. Specific binding can be measured, for example, by determining binding of a molecule compared to binding of a control molecule, which generally is a molecule of similar structure that does not have binding activity. For example, specific binding is indicated if the molecule has measurably higher affinity for cells expressing a protein than for cells that do not express the same protein. Specificity of binding can be determined, for example, by competitive inhibition of a known binding molecule.

The term "specifically binds" "specifically binding," as used herein, includes both low and high affinity specific binding. Specific binding can be exhibited, for example, by a low affinity homing molecule having a Kd of at least about $10^{-4}$ $^M$. Specific binding also can be exhibited by a high affinity molecule, for example, a molecule having a Kd of at least about $10^{-5}$ $^M$. Such a molecule can have, for example, a Kd of at least about $10^{-6}$ $^M$, at least about $10^{-7}$ $^M$, at least about $10^{-8}$ $^M$, at least about $10^{-9}$ $^M$, at least about $10^{-10}$ $^M$ or can have a Kd of at least about $10^{-11}$ $^M$ or $10^{-12}$ $^M$ or smaller. Nonspecific binding may be characterized by a KD of $10^{-3}$ or larger. Both low and high affinity binding molecules are useful and are encompassed by the invention. Low affinity homing molecules may be useful in targeting, for example, multivalent conjugates. High affinity binding molecules may be useful in targeting, for example, multivalent and univalent conjugates The terms "treat," "treated," or "treating" as used herein can refer to both therapeutic treatment or prophylactic or preventative measures, wherein the object is to prevent or slow down (lessen) an undesired physiological condition, symptom, disorder or disease, or to obtain beneficial or desired clinical results. In some embodiments, the term may refer to both treating and preventing. For the purposes of this disclosure, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

The term "tissue" refers to any aggregation of similarly specialized cells that are united in the performance of a particular function.

Methods of Enriching for Progenitor Cells

In certain embodiments the invention provides a method of enriching a population of progenitor cells comprising contacting the progenitor cell with a peptide that specifically binds to the progenitor cell and separating the progenitor cells bound to the peptide from those cells that are not bound to the peptide. Peptides that are suitable for use in the method include any peptide described infra. In some embodiments the peptide may comprise, for example, any of the amino acid sequences disclosed infra. Progenitor cells that are suitable for use in the method are any progenitor cell described infra.

In other embodiments the invention provides a method of eliminating unwanted cells from a population of cells. For example it may be desirable to eliminate undifferentiated pluripotent stem cells from a mixed population of cells comprising progenitor cells. In certain embodiments the method comprises contacting the population of cells with a peptide that binds specifically to the progenitor cells in the population, but not to the pluripotent stem cells in the population, and separating the peptide bound progenitor cells from the population, thereby eliminating the pluripotent stem cells from the population of cells.

The method may be performed using any media known in the art for culturing progenitor cells. Suitable media includes commercially available cell culture media such as DMEM, MEM, RPMI, Hams Media, Media 199 StemPro™ mTESR, Neuralbasal media, Smooth Muscle Cell Media, and the like. In other embodiments the method may be practiced in a suitable buffer such as PBS. The media may be supplemented with serum such as FBS or a serum replacement such as KOSR or B27. The media may optionally include additives such as non-essential amino acids, glutamine, antibiotics such as penicillin and/or streptomycin and the like. The method may be performed in any suitable culture flask, e.g. a plastic flask such as a T25, T75, T150, a roller bottle or stir flask. Alternatively, the method may be performed in a multiwell plate. In some embodiments the progenitor cells may be cultured attached directly to a culture vessel such as plastic culture dish. In other embodiments the progenitor cells may adhere to a matrix comprising one or more proteins, such as one or more proteins found in an extracellular matrix. When grown adherently cells may be seeded at about 30% confluency, about 40% confluency, about 50% confluency, about 60% confluency, about 70% confluency, about 80% confluency, about 90% confluency, or about 95% confluency to practice the method of the invention. The method may be performed at about 37° C., at about 4° C. or at ambient temperature. The progenitor cells may be incubated with the peptide for about 1 hour, about 2 hours, about 3 hours, about 4 hours, about 5 hours about 6 hours, about 7 hours, about 8 hours or more. In some embodiments the progenitor cell is incubated with the peptide for less than 25 hours, less than 20 hours, less than 15 hours, less than 10 hours, less than 5 hours, less than 2 hours. In other embodiments the progenitor cells are incubated with the peptide for 30 minutes. In still other embodiments the progenitor cells are incubated with the peptide for an hour. In yet other embodiments the progenitor cells are incubated with the peptide for 2 hours.

In some embodiments the peptide may comprise a detectable substance and the separation may be based on detection of the detectable substance. For example the detectable substance may be a dye, such as fluorescent dye, a quantum dot (Qdot) and the peptide bound cells may be separated using an method known in the art including cell sorting using a flow cytometer.

In some embodiments the peptide may be a fusion protein. In some embodiments the method may further comprise contacting the peptide bound to the progenitor cell with a second molecule that specifically binds to the peptide. For example, the second molecule that specifically binds to the peptide may include an antibody that binds specifically to the peptide. Where the peptide is a fusion protein comprising a moiety linked to the peptide, the second molecule may be a binding partner of the moiety linked to the peptide. For example, where the peptide is linked to a biotin molecule, the second molecule that binds to the fusion protein, i.e. the peptide-biotin complex, may be a streptavidin molecule. In other embodiments, a streptavidin molecule may be bound to the peptide and the second molecule that binds to the fusion protein, i.e. the peptide-streptavidin complex may be biotin.

In some embodiments the peptide may be a monomer. In some embodiments the peptide may be a multimer. In some embodiments the multivalent peptide may comprise 2, 3, 4, 5, 6, 7, 8, 9, 10, or more peptides capable of binding to a progenitor cell. In other embodiments the multivalent peptide comprises less than 500 peptides, less than 400 peptides, less than 300 hundred peptides, less than 200 peptides, less than 100 peptides, less than 50 peptides, less than 25 peptides, less than 5 peptides capable of specifically binding to the progenitor cells.

Peptide bound progenitor cells may be separated or sorted from the remainder of the population of cells using any technique known in the art. For example, the peptide bound progenitor cells may be separated by flow cytometry, immune-preciptiation, filtration, chromatography, magnetic bead separation, density gradient and the like.

Enriched Progenitor Cell Populations

In certain embodiments the invention provides enriched populations of progenitor cells. The enriched population of progenitor cells may be used as therapeutic to treat a subject in need of cell replacement therapy. For example where the enriched cell population comprises dopaminergic neurons, the enriched population may be used to treat a subject having Parkinson's disease. Where the enriched cell population comprises cells producing insulin, the enriched cell population may be used to treat a subject having diabetes. Where the enriched cell population includes a cell producing collagen 2, the enriched cell population may be used to treat a subject having arthritis. Thus a skilled artisan would appreciate that therapeutic applications will depend on the gene expression profile of the enriched cell population. The skilled artisan would further appreciate that many other therapeutic applications are also contemplated.

The enriched population may be used to screen for agents that differentiate the progenitor cells into a more differentiated or mature phenotype. The enriched population of progenitor cells may be used in drug screening and toxicity assays. The enriched population of cells may be used as an immunogen to generate antibodies against one or more proteins expressed on the progenitor cell surface. Where the enriched population of cells is derived from an individual having a disease the enriched population of progenitor cells may be used to study the onset of the disease. For example an iPS cell may be generated from an individual having a disease such as diabetes. The iPS cell could then be used to generate an endodermal progenitor cell, capable of differentiating further into an insulin producing β-islet cell of the pancreas. The progenitor cell could be enriched according the methods described infra and used to study the onset of the diabetic phenotype under a variety of conditions.

In some embodiments the invention provides an enriched population of progenitor cells that is essentially pure. In other embodiments the invention provides an enriched population of progenitor cells that is about 10%, about 20%, about 30%, about 40%, about 50%, about 60%, about 70%, about 80%, about 95% about 99% pure. In some embodiments the invention provides an enriched population of cells that is greater than 10%, greater than 20%, greater than 30%, greater than 40%, greater than 50%, greater than 60%, greater than 70%, greater than 80%, greater than 90%, greater than 95%, greater than 99% pure.

In some embodiments the invention provides a population of progenitor cells that is essentially free of pluripotent stem cells. In other embodiments the invention provides an enriched population of progenitor cells comprising about 50%, about 40%, about 30%, about 20%, about 10%, about 5%, about 1% pluripotent stem cells. In some embodiments the invention provides an enriched population of progenitor cells comprising less than 50%, less than 40%, less than 30%, less than 20%, less than 10%, less than 5%, less than 1% pluripotent stem cells.

Peptides

In various embodiments the invention provides peptides that specifically bind to a progenitor cell. Suitable peptides include any peptide having specific binding activity with respect to at least one progenitor cell or cell line. The peptide may comprise a plurality of amino acids linked together by one or more peptide bonds. The peptide may have a length of about 3-60 amino acids, about 5-50 amino acids, about 8-35 amino acids, about 10-25 amino acids. In some embodiments the peptide is about 5, about 10, about 15, about 20, about 25, about 30, about 35, about 40, about 45, about 50, about 55, about 60 amino acids long. In some embodiments the peptide is less than 100 amino acids long, less than 90 amino acids long, less than 80 amino acids long, less than 70 amino acids long, less than 60 amino acids long, less than 50 amino acids long, less than 40 amino acids long, less than 30 amino acids long, less than 20 amino acids long, less than 10 amino acids long. In some embodiments the peptide is about 12 amino acids long. In some embodiments the peptide is 12 amino acids long.

In some embodiments the peptide may be antibody or a fragment of an antibody. In other embodiments the peptide is not an antibody or a fragment of an antibody. In some embodiments the peptide comprises an amino acid sequence having PLEXIN homology. In some embodiments the amino acid is substantially homologous to PLEXIN. In some embodiments the peptide binds specifically to one or more ligands, such as a protein, a carbohydrate or a lipid expressed on an endoderm cell. In other embodiments the peptide binds specifically to one or more ligands, such as a protein, a carbohydrate or a lipid expressed on a mesoderm cell. In some embodiments the peptide binds specifically to one or more ligands, such as a protein, a carbohydrate or a lipid expressed on a smooth muscle cell. In other embodiments the peptide binds specifically to one or more ligands, such as a protein, a carbohydrate or a lipid expressed on W10 cell.

In some embodiments the invention provides a peptide selected from SWTYSYPNQNMD (SEQ ID NO: 1); DWTYSLPGLVEE (SEQ ID NO: 2); NWTWSMPTGNPA (SEQ ID NO: 3); GMTLRVLTN-YTE- (SEQ ID NO: 4); TLHVSENSWTYN (SEQ ID NO: 5); DWLWSFAPNVDT (SEQ ID NO: 6); TLSSQNPYMHKK (SEQ ID NO: 7); IDKQMMTSHKAI (SEQ ID NO: 8); QGMETQKLRMLK (SEQ ID NO: 9); GWYWETPLDMFN (SEQ ID NO: 10); GWVIDYDYYPMR (SEQ ID NO: 11); VTAENYQSFSVS (SEQ ID NO: 12); NNKMDDRMMMSIV (SEQ ID NO: 13); STGTDLHSNARI (SEQ ID NO: 14); YEFDNLLN-RTLW (SEQ ID NO: 15); EWTVNERTMWDL (SEQ ID NO: 16) and separating the progenitor cell bound to the peptide comprising the amino acid sequence chosen from SWTYSYPNQNMD (SEQ ID NO: 1); DWTYSLPGLVEE (SEQ ID NO: 2); NWTWSMPTGNPA (SEQ ID NO: 3); GMTLRVLTN-YTE- (SEQ ID NO: 4); TLHVSENSWTYN (SEQ ID NO: 5); DWLWSFAPNVDT (SEQ ID NO: 6); TLSSQNPYMHKK (SEQ ID NO: 7); IDKQMMTSHKAI (SEQ ID NO: 8); QGMETQKLRMLK (SEQ ID NO: 9); GWYWETPLDMFN (SEQ ID NO: 10); GWVIDY-DYYPMR (SEQ ID NO: 11); VTAENYQSFSVS (SEQ ID NO: 12); NNKMDDRMMMSIV (SEQ ID NO: 13); STGT-DLHSNARI (SEQ ID NO: 14); YEFDNLLNRTLW (SEQ ID NO: 15); EWTVNERTMWDL (SEQ ID NO: 16). Also contemplated are variants of the above identified sequences. The variants may comprise one or more conservative amino acid substitutions as described infra. Contemplated peptides include the sequences listed above wherein 1, 2, 3, 4, 5, 6, 7, 8, 9, 10, or 11, amino acids identified in any of the sequences have been substituted with a non-identical conservative amino acid substitution, provided that the peptide can still specifically bind a target molecule on the same progenitor cell as original sequence.

In some embodiments the peptides of the invention have one or more conserved consensus sequences that identify the peptide as a peptide that specifically binds to a progenitor cell. The consensus sequence may be chosen from amino acid sequences DWLW- (SEQ ID NO: 22), -DLWSF- (SEQ ID NO: 23), -WLW-, -WLWS- F-P (SEQ ID NO: 24), -PNV-, F-PNV- (SEQ ID NO: 25), -SF-, -SF-PNV- (SEQ ID NO: 26), -PNV-T- (SEQ ID NO: 27), -W-W-, WLWSF-P (SEQ ID NO: 28), -Y-F-, -NLLN- (SEQ ID NO: 29), Y-F-NLLN- (SEQ ID NO: 30), -LL-RT- (SEQ ID NO: 31), -NRTL- (SEQ ID NO: 32), -NLLNRTL- (SEQ ID NO: 33), F-NLLNRTLA- (SEQ ID NO: 34), and Y-F-NLLNRTL (SEQ ID NO: 35). In other embodiments the invention provides a peptide that selectively binds to a progenitor cell wherein the peptide comprises an amino acid sequence chosen from DWLW- (SEQ ID NO: 22), -DLWSF- (SEQ ID NO: 23) -WLW-, -WLWS- F-P (SEQ ID NO: 24), -PNV-, F-PNV- (SEQ ID NO: 25), -SF-, -SF-PNV- (SEQ ID NO: 26), -PNV-T- (SEQ ID NO: 27), -W-W-, WLWSF-P (SEQ ID NO: 28), -Y-F-, -NLLN- (SEQ ID NO: 29), Y-F-NLLN- (SEQ ID NO: 30), -LL-RT- (SEQ ID NO: 31), -NRTL- (SEQ ID NO: 32), -NLLNRTL- (SEQ ID NO: 33), F-NLLN-RTLA- (SEQ ID NO: 34), Y-F-NLLNRTL (SEQ ID NO: 35).

Also contemplated are peptides having amino acid sequence identified in the preceding paragraph wherein one or more amino acids have been mutated while still maintaining biological activity, e.g. the ability to specifically bind to a progenitor cell. In some embodiments 1, 2, 3, 4, 5 or more of the amino acids have been mutated. Mutations can be introduced into any of the sequences identified above, for example, by standard techniques, such as site-directed mutagenesis and PCR-mediated mutagenesis. For example, conservative amino acid substitutions may be made at one or more predicted non-essential amino acid residues. A non-essential amino acid is one that is not required to maintain biological activity. In some embodiments one or more essential amino acids may be mutated, e.g. by substituting a conservative amino acid for the native amino acid.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential or essential amino acid residue in the peptide is replaced with another amino acid residue from the same side chain family. Alternatively, in another embodiment, mutations can be introduced randomly along all or part of a peptide coding sequence, such as by saturation mutagenesis, and the resultant mutants can be screened for progenitor cell binding activity to identify mutants that retain activity. Following mutagenesis of any of the peptides can be expressed by any recombinant technology known in the art and the activity of the recombinant protein can be determined.

In some embodiments the peptide comprises a detectable substance. The detectable substance may be linked to the peptide. For example the detectable substance may be covalently linked to the peptide or non-covalently linked to the peptide. In some embodiments the detectable substance is linked to the carboxy terminus of the peptide. In other embodiments the detectable substance may be linked to the amino terminus of the peptide. In still other embodiments the detectable substance may be linked to both the amino terminus and the carboxy terminus of the peptide. In certain embodiments the peptide may be linked to one or more R groups or side chains of one or more amino acids comprising the peptide. In still further embodiments the peptide may be linked to a combination of one or more R groups of one or more amino acids comprising the peptide and the amino terminus of the peptide and/or the carboxy terminus of the peptide.

Suitable detectable substances include any substance which can be visually detected, e.g. a fluorescent or luminescent substance, or any substance that can be detected by using some detecting means, e.g. a radioactive label, a member of a specific binding pair, e.g. a nucleic acid sequence, hapten, etc.

Any fluorescent, luminescent, bioluminescent or radioactive molecules may be used as the labels. Many of them are commercially available, for example fluorescent stains Alexa Fluors (Molecular Probes) and DyLight Fluors (Thermo Fisher Scientific). Other non-limited examples of fluorescent labels may be the following molecules: Fluorescein isothiocyanate (FITC), 5-(and 6)-carboxyfluorescein, 5- or 6-carboxyfluorescein, 6-(fluorescein)-5-(and 6)-carboxamido hexanoic acid, fluorescein isothiocyanate, rhodamine, DAPI, tetramethylrhodamine, Cy2, Cy3, Cy5, AMCA, PerCP, R-phycoerythrin (RPE) allophycoerythrin (APC), Texas Red, Princeton Red, Green fluorescent protein (GFP) coated CdSe nanocrystallites, ruthenium derivatives, luminol, isoluminol, acridinium esters, 1,2-dioxetanes and pyridopyridazines, radioactive isotopes of hydrogen, carbon, sulfur, iodide, cobalt, selenium, tritium, or phosphor.

In some embodiments the detectable label may be an enzyme. Non-limiting examples of suitable enzyme labels may be alkaline phosphatase (AP), beta-galactosidase (GAL), glucose-6-phosphate dehydrogenase, beta-N-acetylglucosaminidase, beta.-glucuronidase, invertase, xanthine oxidase, firefly luciferase, glucose oxidase (GO). Such enzymes may be used in combination with a chromogen, a fluorogenic compound or a luminogenic compound to generate a detectable signal.

In other embodiments, the detectable label may be a member of a specific binding pair, e.g. a hapten. As non-limiting examples of suitable haptens may be mentioned 2,4-dinitrophenol (DNP), digoxigenin, fluorescein, Texas Red, tetra methyl rhodamine, nitrotyrosine, acetylaminofluorene, mercury trintrophonol, estradiol, bromodeoxy uridine, dimethylaminonaphthalene sulfonate (dansyl); examples of suitable specific binding pairs may include biotin, streptavidin, complementary natural and non-natural oligonucleotide sequences, zinc fingers binding domain pairs, etc. In certain embodiments green fluorescent protein (GFP) may be used, for example where a peptide is recombinantly produced the GFP protein can be engineered into the peptide.

In some embodiments, the detectable substance may be a biotag. Biotags described herein include a reporter binding domain to provide a binding site for the reporter. For example, when the reporter or diagnostic agent is a metal (e.g., a noble metal or superparamagnetic metal) or paramagnetic ion, the biotag may include a metal binding domain. In such case, the reporter may be reacted with a reagent having a long tail with one or more chelating groups attached to the long tail for binding these ions. The long tail may be a polymer such as a polylysine, polysaccharide, or other derivatized or derivatizable chain having pendant groups to which may be bound to a chelating group for binding the ions. Examples of chelating groups that may be used according to the disclosure include, but are not limited to, ethylenediaminetetraacetic acid (EDTA), diethylenetriaminepentaacetic acid (DTPA), DOTA, NOTA, NETA, porphyrins, polyamines, crown ethers, bis-thiosemicarbazones, polyoximes, and like groups. The chelate is normally linked to the PSMA antibody or functional antibody fragment by a group which enables formation of a bond to the molecule with minimal loss of immunoreactivity and minimal aggregation and/or internal cross-linking. The same chelates, when complexed with non-radioactive metals, such as manganese, iron and gadolinium are useful for MRI, when used along with the antibodies and carriers described herein. Macrocyclic chelates such as NOTA, DOTA, and TETA are of use with a variety of metals and radiometals including, but not limited to, radionuclides of gallium, yttrium and copper, respectively. Other ring-type chelates such as macrocyclic polyethers, which are of interest for stably binding nuclides, such as $^{223}$Ra for RAIT may be used. In certain embodiments, chelating moieties may be used to attach a PET imaging agent, such as an Al$^{18}$F complex, to a targeting molecule for use in PET analysis.

The peptide may be conjugated to a Quantum Dot. Quantum dots are tiny particles, or "nanoparticles", of a semiconductor material, traditionally chalcogenides (selenides or sulfides) of metals like cadmium or zinc (CdSe or ZnS, for example), which range from 2 to 10 nanometers in diameter. Because of their small size, quantum dots display unique optical and electrical properties that are different in character to those of the corresponding bulk material. The most immediately apparent of these is the emission of photons under excitation, which are visible to the human eye as light. Moreover, the wavelength of these photon emissions depends not on the material from which the quantum dot is made, but its size. The ability to precisely control the size of a quantum dot enables the manufacturer to determine the wavelength of the emission, which in turn determines the color of light the human eye perceives. Quantum dots can therefore be "tuned" during production to emit any color of light desired. The ability to control, or "tune" the emission from the quantum dot by changing its core size is called the "size quantization effect". The smaller the dot, the closer it is to the blue end of the spectrum, and the larger the dot, the closer to the red end. Dots can also be tuned beyond visible light, into the infra-red or into the ultra-violet.

The number or detectable labels per reporter molecule may vary. In some embodiments 1 to 3, for example 1, 2 or 3 labels per peptide may be used. In one embodiment the peptide comprises one detectable label. In another embodiment the peptide comprises two to four residues which are detectable substances. In some embodiments, the peptide may comprise more than 3 labels, such as 4 to 150 labels per peptide molecule, 10 to 100 labels per peptide molecule, 20-80 labels per peptide molecule, 30-60 labels per peptide molecule, 40-50 labels per peptide molecule, 1-10 labels per peptide molecule, 2-8 labels per peptide molecule, 3-6 labels per peptide molecule.

Peptide Fusion Proteins

The invention also provides peptide chimeric or fusion proteins. As used herein, a peptide "chimeric protein" or "fusion protein" comprises a peptide as described infra operatively linked to a second peptide or protein. Within a peptide fusion protein the peptide can correspond to all or a portion of one or more of the peptide sequences disclosed infra. In one embodiment, a peptide fusion protein comprises at least one biologically active portion of a peptide disclosed infra. A biologically active portion of a peptide may refer to the portion of the peptide that specifically binds to a progenitor cell. In another embodiment, a peptide fusion protein comprises at least two biologically active portions of a peptide disclosed infra. In yet another embodiment a peptide fusion protein comprises at least three biologically active portions of a peptide disclosed infra. Within the fusion protein, the term "operatively linked" is intended to indicate that the peptide that binds to a progenitor cell and the second peptide or protein are linked in-frame to each other. The second peptide or protein can be fused to the N-terminus or C-terminus of the peptide that binds to the progenitor cell. The second peptide or protein may be, for example, the Fc portion of an antibody. This may be operatively joined to either the N-terminus or the C-terminus of the peptide that binds to the progenitor cell. Fc-target protein fusions have been described in Lo et al. (1998) *Protein Engineering* 11:495-500, and U.S. Pat. Nos. 5,541,087 and 5,726,044.

In one embodiment a peptide fusion protein comprises a progenitor cell binding domain operably linked to the extracellular domain of a second protein or peptide. Such fusion proteins can be further utilized in screening assays for compounds which modulate the peptide binding activity. It is also contemplated that the peptide fusion protein may be used to facilitate isolation or enrichment of the progenitor cell which binds to the peptide. Also contemplated is the use of the fusion peptide to isolate or enrich for the peptide having the biological activity of binding to the progenitor cell.

In another embodiment, the fusion protein is a GST-peptide fusion protein in which the peptide binds specifically to a progenitor cell wherein the peptide sequences are fused to the C-terminus of the GST (i.e., glutathione S-transferase) sequences. Such fusion proteins can facilitate the purification of a recombinant peptide and/or the enrichment of progenitor cells bound to the fusion protein.

In another embodiment, the fusion protein is a protein containing a heterologous signal sequence at its N-terminus. For example, the peptide may comprise a signal sequence, fused to the 5' end of the peptide coding sequence for efficient secretion of the peptide fusion protein where the peptide is produced using recombinant technology. Expression and/or secretion of the peptide can be increased through use of different heterologous signal sequences.

In yet another embodiment, the fusion protein is a peptide-immunoglobulin fusion protein in which the peptide sequences comprising one or more domains are fused to sequences derived from a member of the immunoglobulin protein family. The peptide-immunoglobulin fusion proteins can be used to affect the bioavailability of a peptide cognate ligand. Moreover, the peptide-immunoglobulin fusion proteins of the invention can be used as immunogens to produce anti-peptide antibodies in a subject, to purify peptide ligands, and in screening assays to identify molecules that inhibit the interaction of the peptide with a peptide ligand. The peptide immunoglobulin fusion protein can be used to separate and/or enrich for progenitor cells bound to the peptide immunoglobulin fusion protein.

A peptide chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. Eds. CURRENT PROTOCOLS IN MOLECULAR BIOLOGY, John Wiley & Sons, 1992). Moreover, many expression vectors are commercially available that already encode a fusion moiety (e.g., a GST polypeptide). A peptide-encoding nucleic acid can be cloned into such an expression vector such that the fusion moiety is linked in-frame to the peptide.

Methods of Making Peptides

The peptides of the instant invention may be made according to any method known in the art. In some embodiments the peptides are produced recombinantly, e.g. by transfecting a cell with a nucleic acid encoding the peptide into a host cell and expressing the peptide in the host cell. The nucleic acid may be for example, DNA, or RNA. In some embodiments the nucleic acid encoding the peptide is transfected into the host cell in a vector. The vector may be for example, a plasmid, many of which are commercially available or a viral vector, which are also commercially available. The cell may be a prokaryotic cell such as *E. coli* or a eukaryotic cell such as a mammalian cell, e.g., HeLa cell, or a COS cell, insect cells such as SF9 cells, yeast cells such as Picia pastoris, or the like. In some embodiments the invention thus provides a cell transfected with a nucleic acid encoding a peptide of the invention.

In other embodiments the peptide may be chemically synthesized. Any known method of synthesizing a peptide may be used. A number of traditional techniques for chemically synthesizing proteins, such as solid phase synthesis are known in the art, see, e.g., Merrifield, 1973, *Chemical Polypeptides*, (Katsoyannis and Panayotis eds.) pp. 335-61; Merrifield 1963, *J. Am. Chem. Soc.* 85:2149; Davis et al. 1985, *Biochem. Intl.* 10:394; Finn et al. 1976, *The Proteins* (3d ed.) 2:105; Erikson et al. 1976, *The Proteins* (3d ed.) 2:257; U.S. Pat. No. 3,941,763.

Improvements in the chemical synthesis of proteins include the advent of native chemical ligation. As initially described, native ligation provides for the rapid synthesis of large polypeptides with a natural peptide backbone via the native chemical ligation of two or more unprotected peptide segments. In native ligation none of the reactive functionalities on the peptide segments need to be temporarily masked by a protecting group. Native ligation also allows for the solid phase sequential chemical ligation of peptide segments in an N-terminus to C-terminus direction, with the first solid phase-bound unprotected peptide segment bearing a C-terminal alpha-thioester that reacts with another unprotected peptide segment containing an N-terminal cysteine. Native chemical ligation also permits the solid-phase ligation in the C- to N-terminus direction, with temporary protection of N-terminal cysteine residues on an incoming (second) peptide segment (see, e.g., U.S. Pat. No. 6,326,468; WO 02/18417). Native ligation may also be combined with recombinant technology using intein linked to a chitin binding domain (Muir et al., 1998, *Proc. Natl. Acad. Sci. USA*, 95:6705).

Thus in certain embodiments the invention provides a synthetic peptide, i.e. a peptide produced in vitro by chemical synthesis that specifically binds to a progenitor cell.

Progenitor Cells

In certain embodiments the progenitor cells are multipotent cells. In certain embodiments the progenitor cells are not pluripotent cells.

Progenitor cells derived from pluripotent cells, such as human embryonic stem cells have been described (West et al. (2008) *Regen Med.* 3(3):287). The progenitor cells will be essentially genetically identical to the parental stem cell population from which they originated. Thus the progenitor cell may be about 95%, about 96%, about 97%, about 98%, about 99% genetically identical to the pluripotent stem cell from which it was differentiated. In some embodiments the progenitor cell may be greater than 95%, greater than 96%, greater than 97%, greater than 98%, greater than 99% genetically identical to the pluripotent stem cell it was differentiated from. Because the progenitor cell is essentially genetically identical to its parental pluripotent stem cell and because the parental pluripotent stem cell can be cultured almost indefinitely, the invention provides a limitless supply of a progenitor cell having a specific genomic makeup.

Progenitor cells may be obtained by differentiating a pluripotent stem cell in vitro using defined set of culture conditions. Progenitor cells can be obtained using the method described by West, Id. Briefly a shotgun approach is used that comprises a two-step protocol. In the first step pluripotent stem cells, such as hES cells, are differentiated under an array of in vitro conditions that include colony in situ differentiation, differentiation as embryoid bodies, on non-adherent plastic or hanging drops and differentiation of in the presence of growth factors for various periods of time. The resultant cultures in this matrix are designated candidate cultures (CC). Although heterogeneous, these CCs are enriched for particular cell types. Each CC may be plated at a clonal density in an array of different cell culture media optimized for various stromal and epithelial cell types. The cultures can be allowed to grow in 5% ambient oxygen for a suitable period of time, e.g. 14 days.

Progenitor cells are partially differentiated endodermal, ectodermal and mesodermal cell types that have not undergone terminal differentiation. Typically they are clonal, meaning that they are grown as a colony derived either from a single parental cell. Alternatively, the colony of progenitor cells may be derived from a small number of parental cells. They may express some genes generally seen during embryonic development suggesting that they are an early progenitor of mature cell types found in the adult. Thus in some embodiments of the invention the progenitor cells express one or more of the embryonic genes chosen from MEOX1, MEOX2, FOXF1, ENC1, LXH8, ROR2, SHOX2, GPC2, HSPG and FOXC1. In some embodiments of the invention the progenitor cells express CD133 and/or CD24. In some embodiments of the invention the progenitor cells do not express markers found on pluripotent stem cells such as OCT4. In some embodiments the progenitor cells express lower levels of EBAF, ZNF206 and ZIC3 compared to embryonic stem cells.

In some embodiments the progenitor cells express genes found in neuroglial cells such as one or more of the genes chosen from PLP1, PMP2, GRIN1 and GABRA1. In some embodiments the progenitor cells express a gene expressed in the transport of secretory vesicles found in neurons and melanocytes, e.g. Myosin Va. In other embodiments the progenitor cells express a gene expressed in limb dermis, smooth muscle and vascular endothelial cells, e.g. GARP. In certain embodiments the progenitor cells express a gene associated with the regulation of vascular morphogenesis, e.g., EDIL3. In some embodiments the progenitor cells express a gene expressed in bone and cornea, e.g. COL24A1. In some embodiments the progenitor cells express a gene expressed by oligodendrocytes, e.g. SEMA5A.

In certain embodiments the progenitor cells express one or more homeobox genes chosen from DLX, MEOX, HOX, LIM, MSX, BAPX, PRRX, GSC, IRX, SOX, PITX and FOX. In some embodiments the progenitor cells do not form teratomas when injected into scid mice, but nonetheless express one or more oncofetal genes chosen from PLAG1, AMIGO2, HCLS1, SPINK1, PRAME, INSM1, RAGE, ENC1, BCAS1, GRM1, TSGA10, S100A2, A4, A6, GPC3, EGFL6, PSG5, CEACAM1, CGPC3, SRPUL, DCDC2, LRRN5, SOX11, RUNX3, CA12, STARD10, CXCL1, ANPEP, GAGE6, NCOA6, TACSTD2, and TSPAN8.

Progenitor cells maintain the potential to differentiate further into terminally differentiated cell types. Progenitor cells may have telomere lengths that greater than what is ordinarily found in a terminally differentiated cell. Typically, because of their replicative capacity, they are capable of being produced on a large scale. Generally, they do not form teratomas when transplanted into immunocompromised mice, confirming that they are no longer pluripotent.

Any progenitor cell known in the art may be used in the methods and compositions described infra (See, e.g. US Patent Application Publication Nos: 20080070303; 20100184033; 20120171171). In some embodiments the progenitor cell is a cell that is no longer pluripotent, but still retains the potential to differentiate further into at least one type of mature cell. The progenitor cell may be clonal, such that it is substantially free of any other contaminating cell type. Alternatively, the progenitor cell may be one of several cell types found in vitro cell population.

In some embodiments the progenitor cell used for the various embodiments described infra may be chosen from any of the following established progenitor cell lines, including, but not limited to W10, 4D20.8, SM30, 7PEND24, E15. In certain embodiments the progenitor cell line is W10. In other embodiment the progenitor cell lines may be chosen from one of the following progenitor cell lines: B16, B28, 6-1, B26, B11, B2, CM02, E75, E15, E30, E3, E73, E57, E67 4D20.9, E72, EN7, En55, SK17, Z11, E68, E109, ELS5.8, and M10.

The progenitor cell may have the ability to proliferate in culture over an extensive period of time. For example, a progenitor cell may be passaged in culture about 100 times, about 90 times, about 80 times, about 70 times, about 60 times, about 50 times, about 40 times, about 30 times about 20 times, about 10 times, about 5 times. In some embodiments the progenitor cell may be passaged in culture about 1-60 times, about 5-50 times, about 10-40 times, about 20-30 times.

Methods of Detecting Progenitor Cells

In some embodiments the invention provides a method of detecting a progenitor that is bound to a peptide that specifically binds to the progenitor cell. The peptide may comprise a detectable substance, as described infra, to facilitate detection of the cell peptide bound complex. The cell may be detected in vitro, e.g. by flow cytometry, immunocytochemistry (e.g., staining with tissue specific or cell-marker specific antibodies), fluorescence activated cell sorting (FACS), magnetic activated cell sorting (MACS), fluorescent microscopy, ELISA, radio-immuno-assay, western blot, autoradiography and the like. Peptide bound progenitor cells may be detected in vivo, e.g. by photon laser scanning microscopy, X-Ray, CT Raman, MRI, USG and NMR.

Methods of Monitoring the Differentiation of Progenitor Cells

In certain embodiments the invention provides a method of monitoring the differentiation of a progenitor cell. The progenitor cell may be monitored for differentiation in vitro or in vivo. The progenitor cell may be contacted with one or more peptides that specifically bind to the progenitor cell. The one or more peptides may comprise a detectable substance. The one or more peptides may be provided as monovalent or a multi-valent composition. The peptide comprising the detectable substance bound to the progenitor cell may be monitored/detected over a period of time to allow for the detection of the differentiation of the progenitor cell over time. Any suitable assay may be used to monitor the progenitor cell over time and thereby detect the differentiation of the progenitor cell. Cells may be monitored over time using, for example, microscopy, such as fluorescent microscopy, flow cytometry, immunofluorescence, cytohistochemistry, RIA and ELISA. In some embodiments gene expression may be analyzed to monitor the differentiation of the progenitor cell. For example PCR, Southern or western blots may be used.

Methods of Screening for Peptides

In certain embodiments the invention provides a method of screening for peptides that bind to a progenitor cell. The method may comprise 1) contacting a progenitor cell with a candidate peptide, 2) washing the progenitor cell from step 1) and detecting the bound peptide from step 2). Any detection method described known in the art, including those described infra may be used.

In some embodiments, the screening method may rely on phage display. Phage display is used for the high-throughput screening of protein interactions. In the case of M13 filamentous phage display, the DNA encoding the protein or peptide of interest is ligated into the pIII or pVIII gene, encoding either the minor or major coat protein, respectively. Multiple cloning sites may be used to ensure that the fragments are inserted in all three possible reading frames so that the cDNA fragment is translated in the proper frame. The phage gene and insert DNA hybrid is then transformed into *Escherichia coli* (*E. coli*) bacterial cells such as TG1, SS320, ER2738, or XL1-Blue *E. coli*. If a "phagemid" vector is used (a simplified display construct vector) phage particles will not be released from the *E. coli* cells until they are infected with helper phage, which enables packaging of the phage DNA and assembly of the mature virions with the relevant protein fragment as part of their outer coat on either the minor (pIII) or major (pVIII) coat protein. By contacting a relevant target, such as a progenitor cell, with the transformed phage, a phage that displays a protein that binds to one of those targets on its surface will bind while others may be removed by washing. Those that remain can be eluted, used to produce more phage (by bacterial infection with helper phage) and so produce a phage mixture that is enriched with relevant (i.e. binding) phage. The repeated cycling of these steps is referred to as 'panning' Phage eluted in the final step can be used to infect a suitable bacterial host, from which the phagemids can be collected and the relevant DNA sequence excised and sequenced to identify the relevant, interacting proteins or protein fragments. A library of DNA sequences can be screened in this manner to identify peptide sequences that bind to the progenitor cell. Phage libraries may be generated using techniques known in the art. Alternatively, phage libraries may be purchased from a commercial vendor (e.g. New England BioLabs, Ipswich, Mass.).

Peptide Progenitor Cell Complexes

The invention provides compositions comprising a peptide and a progenitor cell. The progenitor cell may be any progenitor cell described infra, e.g. an endoderm progenitor cell, a mesoderm progenitor cell. In some embodiments the composition comprising the peptide and progenitor cell is isolated from other cell types. In some embodiments the composition comprising a peptide progenitor cell is enriched for the progenitor cell and peptide. In some embodiments the composition comprising the peptide and the progenitor cell is essentially free of pluripotent stem cells. In some embodiments the composition comprising the peptide and the progenitor cell has been depleted of pluripotent stem cells. In some embodiments the composition comprising peptide and the progenitor cell may be present in a population of cells comprising a plurality of cell types. In some embodiments the composition comprising the peptide and the progenitor cell is an in vitro composition. In other embodiments the composition comprising the peptide and the progenitor cell is an in vivo composition.

The peptide may be bound, e.g. chemically bound, to the progenitor cell. The peptide may be covalently bound to the progenitor cell. The peptide may be covalently bound to a protein, carbohydrate or lipid expressed on the surface of the progenitor cell. In some embodiments the peptide may be taken up or internalized, e.g. by endocytosis, by the progenitor cell. The peptide may be any peptide described infra. The peptide may further comprise one or more detectable substances. In some embodiments the peptide may be non-covalently bound to the progenitor cell. For example the peptide may be bound to the cell by an ionic interaction, a hydrophobic interaction, a hydrophilic interaction or the like.

In certain embodiments the invention provides a composition comprising a progenitor cell and one or more peptides bound the progenitor cell. One or more peptides may include about 1, about 2, about 4, about 8, about 16, about 32, about 64, about 128, about 200, about 400, about 500 peptides. In some embodiments a plurality of peptides includes less than 50,000, less than 40,000, less than 30,000, less than 20,000, less than 10,000, less than 5,000, less than 1,000, less than 500, less than 100, less than 50 peptides. In some embodiments 1 peptide, 2 peptides, 5 peptides, 10 peptides, 20 peptides, 100 peptides, 1000 peptides, 10,000 peptides are bound to the progenitor cell in the composition comprising the peptide and the progenitor cell.

Pluripotent Stem Cells

Pluripotent stem cells are cells that have the potential, under the appropriate culture conditions to differentiate into cells from all three germ layers and are capable of immortal proliferation in vitro. Their ability to differentiate into cells from all three germ layers provides the potential to manufacture, in vitro, virtually any cell in the body. Their ability to proliferate virtually endlessly in culture provides a means to scale the manufacture of cellular therapeutics by providing an endless supply of identical starting material from which cellular therapeutics can be manufactured. Thus, pluripotent stem cells provide the potential to derive cellular therapeutics to treat a plethora of otherwise intractable human diseases such as Parkinson's disease, diabetes, spinal cord injury, multiple sclerosis, stroke, heart disease, osteoarthritis, macular degeneration to name but a few.

In certain embodiments pluripotent stem cells may be derived from any mammal, including primates such as humans, and macaques, rodents such as mice and rats, and ungulates such as cows and sheep, as well as pigs, horses and the like. Stem cells may be isolated from the inner cell mass of the blastocyst stage of a fertilized egg, such as an in vitro fertilized egg. Typically, the pluripotent stem cells are not derived from a malignant source. Pluripotent stem cells will form teratomas when implanted in an immuno-deficient mouse, e.g., a SCID mouse. In some embodiments the pluripotent stem cell is a human pluripotent stem cell.

Human pluripotent stem cells are characterized by the expression of OCT-4, telomerase and alkaline phosphatase, as well as the expression of cell surface markers SSEA-3, SSEA-4, TRA-1-60, TRA-1-81 and the absence of the marker SSEA-1. Morphologically the cells have prominent nucleoli, and a high nucleus to cytoplasm ratio.

Human pluripotent stem cells may be maintained indefinitely in culture under suitable conditions. Exemplary conditions include a matrix for growing the cells on such as feeder cells e.g. murine embryonic fibroblasts, matrigel, or a synthetic surface (See, e.g. U.S. Pat. Nos. 5,843,780; 6,800,480; 7,410,798; US Patent Application Publication Nos: 20120220720; 20100317101).

Numerous established human pluripotent cell lines are known. Established hES cell lines include, but not limited to, H1, H7, H9, H13 or H14 (Thompson, (1998) *Science* 282:1145); hESBGN-01, hESBGN-02, hESBGN-03 (BresaGen, Inc., Athens, Ga.); HES-1, HES-2, HES-3, HES-4, HES-5, HES-6 (from ES Cell International, Inc., Singapore); HSF-1, HSF-6 (from University of California at San Francisco); I 3, I 3.2, I 3.3, I 4, I 6, I 6.2, J 3, J 3.2 (derived at the Technion-Israel Institute of Technology, Haifa, Israel); UCSF-1 and UCSF-2 (Genbacev et al., (2005) *Fertil. Steril.* 83(5):1517); lines HUES 1-17 (Cowan et al., (2004) NEJM 350(13):1353); and line ACT-14 (Klimanskaya et al., (2005) *Lancet*, 365(9471):1636). Many of these cell lines are available from established cell banks, such as WiCell and the UK Cell Bank. cGMP qualified human pluripotent stem cell lines including ESI 017, ESI 035, ESI 049, ESI 051, and ESI 053, are available commercially from BioTime, Inc. Alameda, Calif.

pPS cells used in the present invention may have been derived in a feeder-free manner (see, e.g., Klimanskaya et al., (2005) Lancet 365(9471):1636). In certain embodiments the pPS may be cultured prior to use in a serum free environment.

pPS cells may be cultured using a variety of substrates, media, and other supplements and factors known in the art. In some embodiments a suitable substrate may be comprised of a matrix including one or more of the following: laminin, collagen, fibronectin, vitronectin, heparin sulfate proteoglycan. In some embodiments the matrix may comprise a soluble extract of the basement membrane from a murine EHS sarcoma which is commercially available as Matrigel™. (BD Biosciences, San Jose, Calif.). In other embodiments the matrix may comprise one more isolated matrix proteins of human, humanized, or murine origin, e.g., CELLstart™. (Invitrogen, Carlsbad, Calif.). In still other embodiments a suitable substrate may be comprised of one or more polymers such as one or more acrylates. The polymers may include one or more proteins or peptide fragments derived from a protein found in vivo in the extra-cellular matrix. In one particular embodiment the substrate is comprised of one or more acrylates and a conjugated vitronectin peptide (see, e.g. U.S Patent Publication No. 2009/0191633; U.S Patent Publication No. 2009/0191626; U.S Patent Publication No. 2009/0203065). pPS cells can be propagated continuously in culture, using culture conditions that promote proliferation while inhibiting differentiation.

Exemplary medium may be made with 80% DMEM (such as Knock-Out DMEM, Gibco), 20% of either defined fetal bovine serum (FBS, Hyclone) or serum replacement (US 2002/0076747 A1, Life Technologies Inc.), 1% non-essential amino acids, 1 mM L-glutamine, and 0.1 mM .beta.-mercaptoethanol. Other suitable media include serum free defined media such as X-VIVO™ 10 (Lonza, Walkersville, Md.). Still other commercially available media formulations that may be used in certain embodiments of the invention include X-VIVO™ 15 (Lonza, Walkersville, Md.); mTeSR™ (Stem Cell Technologies, Vancouver, Calif.); hTeSR∩ (Stem Cell Technologies, Vancouver, Calif.), StemPro™ (Invitrogen, Carlsbad, Calif.) and Cellgro™ DC (Mediatech, Inc., Manassas, Va.).

In certain embodiments, pPS cells may be maintained in an undifferentiated state without added feeder cells (see, e.g., (2004) Rosler et al., Dev. Dynam. 229:259). Feeder-free cultures are typically supported by a nutrient medium containing factors that promote proliferation of the cells without differentiation (see, e.g., U.S. Pat. No. 6,800,480). In certain embodiments, conditioned media containing such factors may be used. Conditioned media may be obtained by culturing the media with cells secreting such factors. Suitable cells include irradiated (.about.4,000 rad) primary mouse embryonic fibroblasts, telomerized mouse fibroblasts, or fibroblast-like cells derived from pPS cells (U.S. Pat. No. 6,642,048). Medium can be conditioned by plating the feeders in a serum free medium such as KO DMEM supplemented with 20% serum replacement and 4 ng/mL bFGF. Medium that has been conditioned for 1-2 days may be supplemented with further bFGF, and used to support pPS cell culture for 1-2 days (see. e.g., WO 01/51616; Xu et al., (2001) Nat. Biotechnol. 19:971).

Alternatively, fresh or non-conditioned medium can be used, which has been supplemented with added factors (like a fibroblast growth factor or forskolin) that promote proliferation of the cells in an undifferentiated form. Exemplary is a base medium like X-VIVO™ 10 (Lonza, Walkersville, Md.) or QBSF™-60 (Quality Biological Inc. Gaithersburg, Md.), supplemented with bFGF at 40-80 ng/mL, and optionally containing SCF (15 ng/mL), or Flt3 ligand (75 ng/mL) (see, e.g., Xu et al., (2005) Stem Cells 23(3):315. These media formulations have the advantage of supporting cell growth at 2-3 times the rate in other systems (see, e.g., WO 03/020920). In some embodiments pPS cells such as hES cells may be cultured in a media comprising bFGF and TGFβ. Suitable concentrations of bFGF include about 80 ng/ml. Suitable concentrations of TGFβ include about 0.5 ng/ml.

In some embodiments, the pluripotent stem cells, e.g. hES cells, may be plated at >15,000 cells $cm^2$ (optimally 90,000 $cm^2$ to 170,000 $cm^2$). Typically, enzymatic digestion may be halted before cells become completely dispersed (e.g., about 5 minutes with collagenase IV). Clumps of about 10 to about 2,000 cells may then be plated directly onto a suitable substrate without further dispersal. Alternatively, the cells may be harvested without enzymes before the plate reaches confluence by incubating the cells for about 5 minutes in a solution of 0.5 mM EDTA in PBS or by simply detaching the desired cells from the plate mechanically, such as by scraping or isolation with a fine pipette or a cell scraper. After washing from the culture vessel, the cells may be plated into a new culture without further dispersal. In a further illustration, confluent human embryonic stem cells cultured in the absence of feeders may be removed from the plates by incubating with a solution of 0.05% (wt/vol) trypsin (Gibco® Carlsbad, Calif.) and 0.05 mM EDTA for 5-15 minutes at 37.degree. C. The remaining cells in the plate may be removed and the cells may be triturated into a suspension comprising single cells and small clusters, and then plated at densities of 50,000-200,000 cells $cm^2$ to promote survival and limit differentiation.

In certain embodiments, primate pluripotent stem cells may be cultured on a layer of feeder cells, typically fibroblasts derived from embryonic or fetal tissue (Thomson et al. (1998) Science 282:1145). In certain embodiments, those feeder cells may be derived from human or murine source. Human feeder cells can be isolated from various human tissues or derived by differentiation of human embryonic stem cells into fibroblast cells (see, e.g., WO 01/51616) In certain embodiments, human feeder cells that may be used include, but are not limited to, placental fibroblasts (see, e.g., Genbacev et al. (2005) Fertil. Steril. 83(5):1517), fallopian tube epithelial cells (see, e.g., Richards et al. (2002) Nat. Biotechnol., 20:933), foreskin fibroblasts (see, e.g., Amit et al. (2003) Biol. Reprod. 68:2150), uterine endometrial cells (see, e.g., Lee et al. (2005) Biol. Reprod. 72(1):42).

In the practice of the present invention, there are various solid surfaces that may be used in the culturing of cells. Those solid surfaces include, but are not limited to, standard commercially available cell culture plates such as 6-well, 24-well, 96-well, or 144-well plates. Other solid surfaces include, but are not limited to, microcarriers and disks. In certain embodiments, the microcarriers may be used in stirred-tank bioreactors for attachment of the cells. In certain embodiments, the microcarriers are beads. Those beads come in various forms such as Cytodex Dextran microcarrier beads with positive charge groups to augment cell attachment, gelatin/collagen-coated beads for cell attachment, and macroporous microcarrier beads with different porosities for attachment of cells. The Cytodex dextran, gelatin-coated and the macroporous microcarrier beads are commercially available (Sigma-Aldrich, St. Louis, Mo. or Solohill Engineering Inc., Ann Arbor, Mich.). In certain embodiments, the beads are 90-200 μm in size with an area of 350-500 cm². Beads may be composed of a variety of materials such as, but not limited to, glass or plastic. Disks are sold by companies such as New Brunswick Scientific Co, Inc. (Edison, N.J.). In certain embodiments, the disks are Fibra-cel Disks, which are polyester/polypropylene disks. A gram of these disks provide a surface area of 1200 cm².

The solid surface suitable for growing pPS cells may be made of a variety of substances including, but not limited to, glass or plastic such as polystyrene, polyvinylchloride, polycarbonate, polytetrafluorethylene, melinex, or thermanox. In certain embodiments of the invention, the solid surfaces may be three-dimensional in shape. Exemplary three-dimensional solid surfaces are described, e.g., in US 2005/0031598.

In certain embodiments, the cells may be in a single-cell suspension. The single-cell suspension may comprise culturing the cells in a spinner flask, in a shaker flask, or in a fermenters. Fermenters that may be used include, but are not limited to, Celligen Plus (New Brunswick Scientific Co, Inc., Edison, N.J.), and the STR or the Stirred-Tank Reactor (Applikon Inc., Foster City, Calif.). In certain embodiments, the bioreactors may be continuously perfused with media or used in a fed-batch mode. Other suitable bioreactors include the Wave Bioreactor bags (GE Healthcare, Piscataway, N.J.). Bioreactors come in different sizes including, but not limited to 2.2 liter, 5 liter, 7.5 liter, 14 liter or 20 liter, 100 liter, 100 liter, 10,000 liter or larger.

Induced Pluripotent Stem Cells

Progenitor cells may be obtained from an induced pluripotent stem cell (iPS). An induced pluripotent stem cell is a pluripotent cell, i.e. it has the ability to differentiate into at least one cell type derived from each of the three primary germ layers, ectoderm, endoderm and mesoderm, but the iPS cell is typically derived from a non-pluripotent cell, such as a somatic cell. Typically an iPS cell is not derived from a fertilized egg, e.g. the blastocyst of the fertilized egg. An iPS cell may be a somatic cell, that has been genetically reprogrammed to revert back to a pluripotent state typically found in embryonic stem cells (see, e.g. US Patent Application Publication Nos: 20080233610; 20090047263; 20100003757). The reprogramming can be achieved by contacting, e.g., transfecting, the target cell with one or more reprogramming factors. The reprogramming factors may be a nucleic acid, such as DNA or RNA encoding a factor, a protein factor capable of reprogramming the target cell, or a small molecule capable of inducing expression of one or more reprogramming factors within a target cell.

iPS cells may be derived by transfection of certain stem cell-associated genes into non-pluripotent cells, such as adult fibroblasts. Transfection is typically achieved through viral vectors, such as retroviruses. Transfected genes include the master transcriptional regulators Oct-3/4 (Pou5f1) and Sox2, although it is suggested that other genes enhance the efficiency of induction. After 3-4 weeks, small numbers of transfected cells begin to become morphologically and biochemically similar to pluripotent stem cells, and may be isolated through morphological selection, doubling time, or through a reporter gene and antibiotic selection.

Yamanaka et al. have successfully transformed human fibroblasts into pluripotent stem cells using the same four pivotal genes: Oct3/4, Sox2, Klf4, and c-Myc with a retroviral system (US Patent Publication No. 20090047263). Thomson and colleagues used OCT4, SOX2, NANOG, and a different gene LIN28 using a lentiviral system (US Patent Publication No. 20080233610).

Potency-determining factors that can reprogram somatic cells include, but are not limited to, factors such as Oct-4, Sox2, FoxD3, UTF1, Stella, Rex1, ZNF206, Sox15, Myb12, Lin28, Nanog, DPPA2, ESG1, Otx2 c-Myc and Klf4, or combinations thereof.

One of the strategies for avoiding shortcomings of reprogramming somatic cells has been to use small compounds that can mimic the effects of transcription factors. These molecule compounds can compensate for a reprogramming factor that does not effectively target the genome or fails at reprogramming for another reason; thus they raise reprogramming efficiency. They also avoid the problem of genomic integration, which in some cases contributes to tumor genesis. Studies using this strategy were conducted in 2008. Melton et al. studied the effects of histone deacetylase (HDAC) inhibitor valproic acid. They found that it increased reprogramming efficiency 100-fold (compared to Yamanaka's traditional transcription factor method) (Huangfu et al. (2008) Nature Biotech. 26:795). The researchers proposed that this compound was mimicking the signaling that is usually caused by the transcription factor c-Myc. A similar type of compensation mechanism was proposed to mimic the effects of Sox2. In 2008, Ding et al. used the inhibition of histone methyl transferase (HMT) with BIX-01294 in combination with the activation of calcium channels in the plasma membrane in order to increase reprogramming efficiency (Desponts et al. (2008) *Cell Stem Cell* 3:568).

In 2009, Ding and colleagues demonstrated a successful alternative to transcription factor reprogramming through the use of drug-like chemicals. This was the first method in human cells that was mechanism-specific for the reprogramming process. Ding tackled the problem of genomic insertion by using purified proteins to transform adult cells into embryonic-like cells. Efficiency was improved using ALK5 inhibitor SB431412 and MEK inhibitor PD0325901, which when used in combination were highly effective at promoting the transformation from fibroblast to iPS cell (see, e.g. Zhou et al. (2009) *Cell Stem Cell* 8:381; Abujarour et al. (2009) *Genome Biol.* 10:220; Lin et al. (209) *Nature Methods* 6:805).

This two-chemical technique increased the efficiency of the classical genetic method by 100 fold. Using Thiazovivin with the two previous chemicals, efficiency was increased by 200 fold. Furthermore, this method took only two weeks to complete reprogramming while the classic method took four weeks (see, e.g. *Science Daily* Dec. 10, 2009).

Induced pluripotent stem cells may express any number of pluripotent cell markers, including: alkaline phosphatase (AP); ABCG2; stage specific embryonic antigen-1 (SSEA-1); SSEA-3; SSEA-4; TRA-1-60; TRA-1-81; Tra-2-49/6E; ERas/ECAT5, E-cadherin; .beta.III-tubulin; .alpha.-smooth muscle actin (.alpha.-SMA); fibroblast growth factor 4 (Fgf4), Cripto, Dax1; zinc finger protein 296 (Zfp296); N-acetyltransferase-1 (Nat1); (ES cell associated transcript 1 (ECAT1); ESG1/DPPA5/ECAT2; ECAT3; ECAT6; ECAT7; ECAT8; ECAT9; ECAT10; ECAT15-1; ECAT15-2; Fthl17; Sal14; undifferentiated embryonic cell transcription factor (Utf1); Rex1; p53; G3PDH; telomerase, including TERT; silent X chromosome genes; Dnmt3a; Dnmt3b; TRIM28; F-box containing protein 15 (Fbx15); Nanog/ECAT4; Oct3/4; Sox2; Klf4; c-Myc; Esrrb; TDGF1; GABRB3; Zfp42, FoxD3; GDF3; CYP25A1; developmental pluripotency-associated 2 (DPPA2); T-cell lymphoma breakpoint 1 (Tcl1); DPPA3/Stella; DPPA4; other general markers for pluripotency, etc. Other markers can include Dnmt3L; Sox15; Stat3; Grb2; SV40 Large T Antigen; HPV16 E6; HPV16 E7, (β-catenin, and Bmi1. Such cells can also be characterized by the down-regulation of markers characteristic of the differentiated cell from which the iPS cell is induced. For example, iPS cells derived from fibroblasts may be characterized by down-regulation of the fibroblast cell marker Thy 1 and/or up-regulation of SSEA-3.

Other techniques for nuclear reprogramming which have been reported include nuclear transfer into oocytes (Wakayama et al., *Nature* 394:369-374, 1998; Wilmut et al., *Nature* 385:810-813, 1997) as well as techniques for nuclear reprogramming of a somatic cell nucleus by fusing a somatic cell and an ES cell (Tada et al., *Curr. Biol.* 11:1553-1558, 2001; Cowan et al., *Science* 309:1369-73, 2005). Another reported technique for reprogramming a cell nucleus involves treatment of a differentiated cell with an undifferentiated human carcinoma cell extract (Taranger et al., *Mol. Biol. Cell* 16:5719-35, 2005).

Induced pluripotent cells can be cultured in any medium used to support growth of pluripotent cells. Typical culture medium includes, but is not limited to, a defined medium, such as TeSR™. (StemCell Technologies, Inc.; Vancouver, Canada), mTeSR™ (StemCell Technologies, Inc.) and StemLine® serum-free medium (Sigma; St. Louis, Mo.), as well as conditioned medium, such as mouse embryonic fibroblast (MEF)-conditioned medium. As used herein, a "defined medium" refers to a biochemically defined formulation comprised solely of biochemically-defined constituents. A defined medium may also include solely constituents having known chemical compositions. A defined medium may further include constituents derived from known sources. As used herein, "conditioned medium" refers to a growth medium that is further supplemented with soluble factors from cells cultured in the medium. Alternatively, cells can be maintained on MEFs in culture medium.

Kits

In certain embodiment the invention provides a kit comprising one or more peptides that bind specifically to a progenitor cell and at least one container. The kit may optionally comprise one or more progenitor cell lines and instructions for using the kit.

The peptides may be provided lyophilized in a container. Alternatively, the peptides may be provided in a suitable buffer, e.g. PBS. The peptides may be linked to one or more detectable substances. The kit may optionally comprise one or more nucleic acid sequences encoding for one or more peptides. The kit may optionally comprise a vector suitable for expressing the one or more nucleic acid sequences encoding the one or more peptides. The kit may optionally comprise a cell suitable for expressing the one or more nucleic acid sequences encoding the one or more peptides. The progenitor cell lines may be provided frozen in a container. A suitable media (e.g. a freezing media) may be provided in the container with the cells. The kit may optionally comprise a suitable media for culturing the progenitor cells. The kit may optionally comprise one or more antibodies. The antibody may bind specifically to one or more of the peptides provide with the kit. The antibodies may specifically bind to one or more proteins expressed by the progenitor cells. The kit may comprise one or more wash solutions. The wash solution may be a suitable buffer, such as PBS. The kit may optionally provide a vessel, e.g. such as a multiwell plate, for growing progenitor cells in culture. The kit may optionally comprise one or more containers for mixing the peptides with the progenitor cells. The kit may optionally comprise one or more detectable substances, e.g. quantum dots (Qdots).

The kit may be used to identify peptides that bind to progenitor cells. The kit may be used to screen for progenitor cells that bind to one or more peptides provided in the kit. The kit may be used to monitor the in vitro growth and development (e.g. the differentiation) of one or more progenitor cells. The kit may be used to monitor the in vivo growth and development (e.g. the differentiation) of one or more progenitor cells. The kit may be used to isolate or enrich one or more progenitor cell lines.

EXAMPLES

Example 1: Cell Culture

The W10 and other embryonic progenitor cell lines were obtained from BioTime, Inc. (Alameda, Calif.) and human pluripotent stem cells (hES cell line, H9) were obtained from the Stem Cell Core at Sanford-Burnham Medical Research Institute (La Jolla, Calif.). Embryonic progenitor cell line (P12-30), human dermal fibroblasts (Invitrogen, P2-10) and coronary artery smooth muscle cells (CASMS) (Lonza, P6-19) were grown following manufacturers' instructions. Human embryonic stem cells (P37-55) were cultured as colonies using standard conditions (Leonardo T R, Schell J P, Nickey K S, Tran H T (2012) Chapter 1-Culturing Human Pluripotent Stem Cells on a Feeder Layer. In: Peterson S, Loring J F, editors. *Human Stem Cell Manual, A Laboratory Guide.* 2nd ed. Boston: Academic Press. pp. 3-14).

Example 2: Flow Cytometry

For flow cytometric analysis of labeled cells, cells were removed from the plates using TrypLE for 5 min at 37° C. Cells were resuspended in PBS, passed through strain top tubes and analyzed using flow cytometer. Control samples included unlabeled cells and cells labeled with untargeted Qdots. For each sample, 10,000 events were quantified. The LSRFortessa flow cytometer (BD Biosciences) was used with a violet laser excitation at 405 nm with a 605/23 bandpass filter to detect Qdot605 and the yellow laser excitation at 561 nm with a 670/30 bandpass filter to detect Qdot655. Cell autofluorescence was detected with the blue laser excited at 488 nm and a 510/25 bandpass filter.

Example 3: Gene Expression Analysis

Total RNA was extracted directly from cells growing in 6-well or 6 cm tissue culture plates using Qiagen RNeasy mini kits (Qiagen, Gaithersburg, Md.) according to the manufacturer's instructions. RNA concentrations were measured using a Beckman DU530 or Nanodrop spectrophotometer and RNA quality determined by denaturing agarose gel electrophoresis or an Agilent 2100 Bioanalyzer. Whole-genome expression analysis was carried out using Illumina Human Ref-8v3 BeadArrays and RNA levels for certain genes were confirmed by quantitative PCR. For Illumina BeadArrays, total RNA was linearly amplified and biotin-labeled using Illumina TotalPrep kits (Illumina, San Diego, Calif.), and cRNA was quality controlled using an Agilent 2100 Bioanalyzer. cRNA was hybridized to Illumina Bead-Chips, processed, and read using a BeadStation array reader according to the manufacturer's instructions (Illumina, San Diego, Calif.). Values less than 90 relative fluorescence units (RFUs) were considered nonspecific background signal.

Example 4: Myodifferentiation

W10 cells were grown as micromass cultures by plating 200,000 cells/10 µl on 0.1% gelatin-coated wells for 1.5 h before addition of remaining media. Micromass cultures were differentiated in myodifferentiation media (Smooth Muscle Cell Media 2 and Supplement Mix (PromoCell)+1% GlutaMax+1% penicillin-streptomycin+1 mM pyruvate+10 µM dexamethasone+350 µM l-proline+170 µM l-ascorbic acid+6.25 µg/ml insulin+6.25 µg/ml transferring+6.25 µg/ml selenious acid+1.25 µg/ml serum albumin+5.35 µg/ml linoleic acid) supplemented with 10 ng/ml TGFβ3).

Figure 1B:
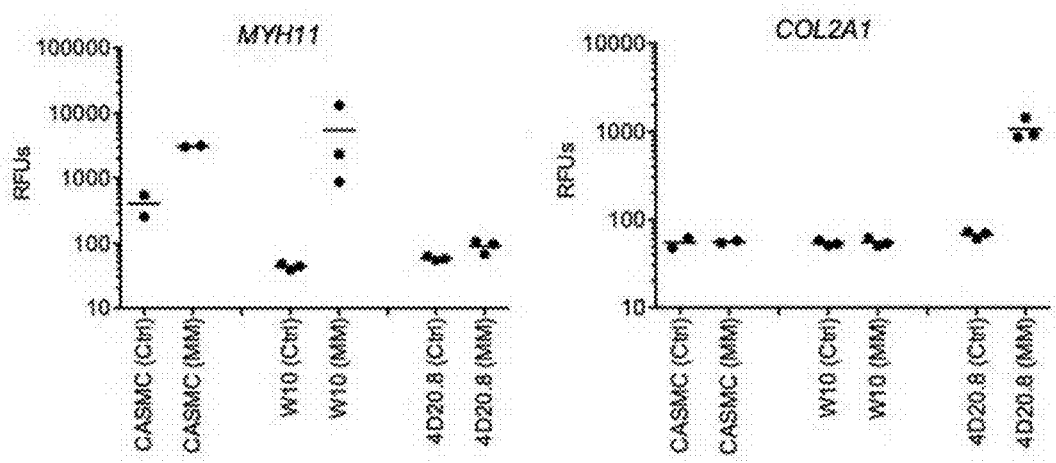
Figure 9C:
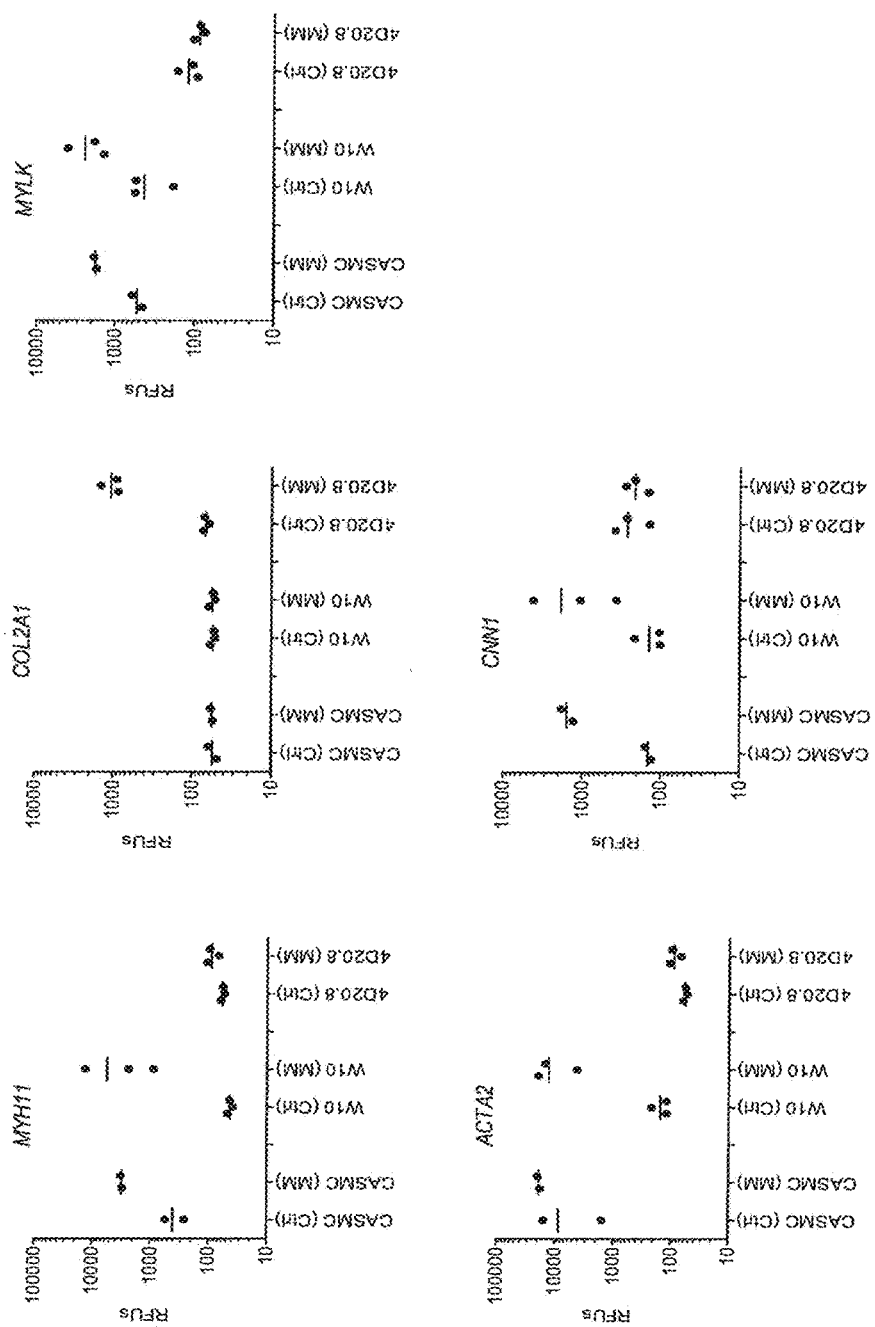

The embryonic progenitor cell line, W10, expresses markers such as transcription factor, heart and neural crest derivatives-expressed 2 (HAND2) and distal HOX genes such as HOXA4 and HOXB7. When differentiated in high density in the presence of 10 ng/ml TGFβ3, a condition that stimulates chondrogenic differentiation of other clonal progenitor cell lines (4D20.8, SM30, 7PEND24, and E15) and the upregulation of COL2A1 expression (Sternberg et al. (2012) Regen Med 7: 481-501), W10 instead displays differentiation to cells with markedly increased expression of smooth muscle cell markers such as smooth muscle heavy chain 11 (MYH11) (FIG. 1), calponin 1 (CNN1), myosin light chain kinase (MYLK), and smooth muscle actin (ACTA2) as measured by microarray analysis (see, Example 3 above) (FIG. 9).

Example 5: Selection of Cell Binding Peptides from Phage Display Library

Peptide phage display library (Ph.D.-12, New England Biolabs, Beverly Mass.) at $2 \times 10^{11}$ pfu was adsorbed against human dermal fibroblasts (HDF) ($1 \times 10^6$ cells grown for 48 h in gelatin-coated 10 cm-dish) for 1 h on ice in W10 growth media with 2% BSA (library volume: 5 ml). The subtracted library was removed from the HDF and incubated with W10 cells plated on gelatin-coated 10 cm-dish for 2 h at 37° C., with occasional mixing. Cells were washed with washing buffer (1% BSA in PBS+0.9 mM $CaCl_2$+0.73 mM $MgCl_2$) using 100 times the library volume. Cells were harvested in 1 volume of dissociation buffer (PBS+1 mM EDTA), washed with 2 volumes of PBS and lysed in ⅕th volume of lysis buffer (30 mM Tris pH 7.5+2 mM EDTA+protease inhibitors cocktail (cOmplete, EDTA-free Protease Inhibitor Cocktail Tablets, Roche Diagnostics) on ice for 1 hour. Cells were passed through 25 G needle in 1 ml syringe and insoluble material was collected by centrifugation at 18000 g for 5 min at 4° C. Cleared lysate was transferred to a clean microcentrifuge tube and kept on ice until titration and amplification following standard protocols. In total, three rounds of biopanning were performed using similar conditions, except that the concentration of the amplified recovered phage pool was decreased to $2 \times 10^{10}$ pfu for rounds 2 and 3. The recovery of the phage pool was calculated as the ratio between the recovered phage and the input phage for each round panning.

Sequencing of Recovered Phage: Individual phage plaques from the titration plates were grown as individual phage cultures by infection of the E. Coli bacteria strain ER2738 (New England Biolabs, Beverly, Mass.). DNA was extracted using the rapid purification of sequencing templates protocol (Ph.D. Phage Display Libraries, Manual from New England Biolabs, Version 1.0, 9/09) or amplified by PCR from a peptide phage dilution using primers that hybridize outside the insert (M13KE Ext01: 3' TTGTCATTGTCGGCGCAACT 5' (SEQ ID NO: 36); M13KE Ext02: 3' GCATTCCACAGACAGCCCTCA 5' (SEQ ID NO: 37)). DNA was sequenced using primer −96 gIII (3' CCCTCATAGTTAGCGTAACG 5' (SEQ ID NO: 38)). The corresponding peptide sequences were analyzed using the EMBOSS suite of bioinformatic software and their similarities were identified by ClustalW analysis. Homologous peptide sequences were identified in PepBank (available online at pepbank.mgh.harvard.edu) using the Smith-Waterman search algorithm against public peptide library (201572 residues in 21672 sequences) and selecting sequences with E( )<1. Homologous protein sequences were identified in the Homo sapiens RefSeq protein database using Blastp available online.

Figure 2A:
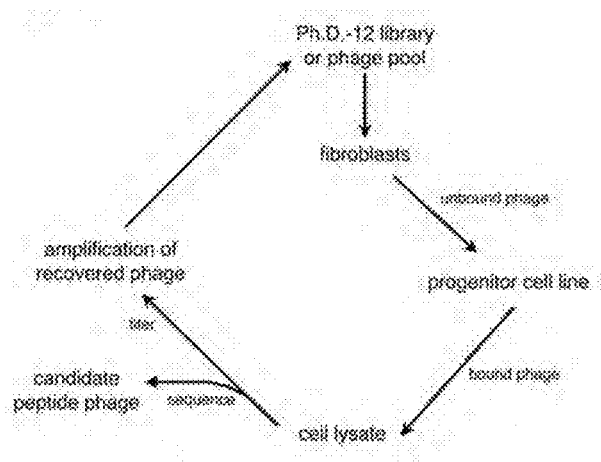
Figure 2B:
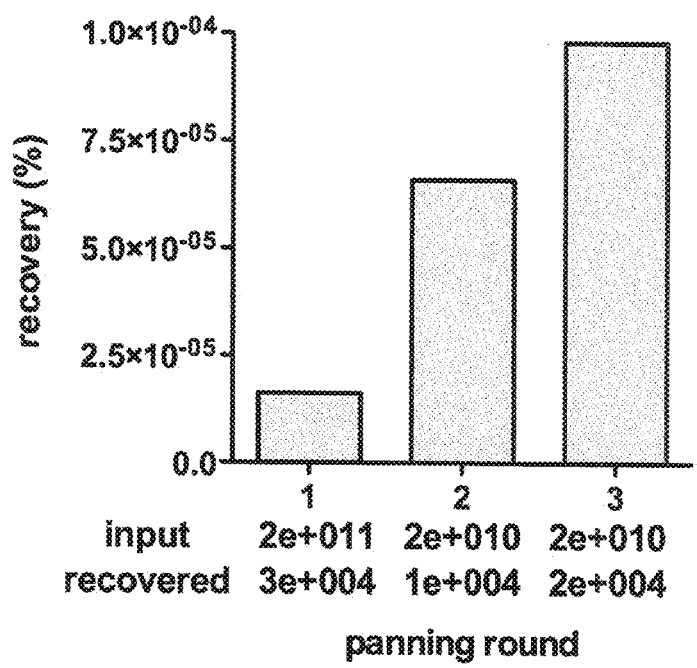
Figure 2D:
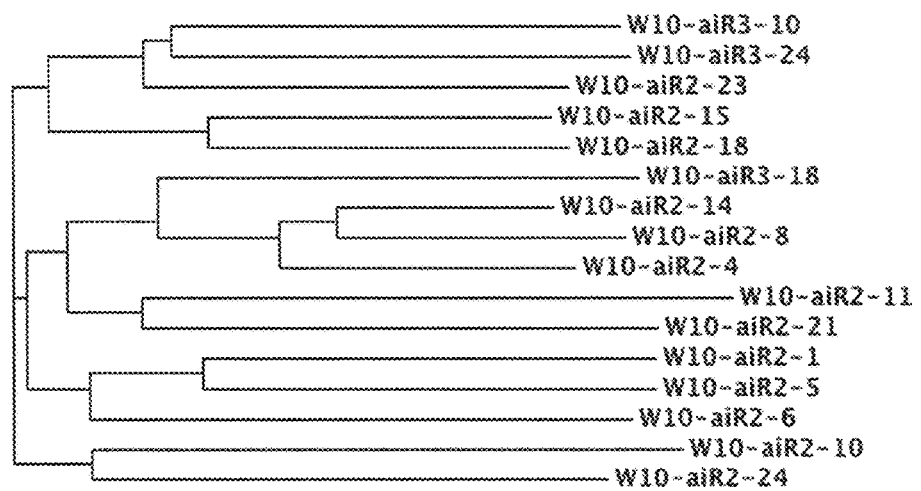

Results:

Cell targeting peptide phages were selected from a 12-mer linear peptide display library by 3 rounds of selection against undifferentiated W10 progenitor cells which included a negative selection against adult human dermal fibroblast (HDF) cells at each round to remove peptides binding common cell surface markers (FIG. 2A). After each round of selection, the percentage of input phage recovered from the target cells increased indicating enrichment of the phage library for W10 cell binding peptides (FIG. 2B). Peptide sequences were obtained from a sample of 23 individual peptide display phages recovered from rounds 2 and 3. Over-representation of several unique sequences and families of related sequences indicated a collapse of the library diversity as early as round 2. Sequences from candidate peptide phages were compared using ClustalW multiple sequence alignment software (FIG. 2C). Small peptide motifs were identified in several families of related sequences (FIG. 2D). The rare amino acid, tryptophan, appeared in the second position in 7 of the 24 12-mer peptide sequences suggesting selective pressure for binding to a cell surface epitope. Homology of selected peptides to known proteins can sometimes be informative for identification of candidates for the native cell binding ligand. Short peptide homologies to intracellular, membrane and extracellular proteins, identified by BLAST searching, did not indicate obvious similarities to functionally relevant domains of known cell binding proteins with the possible exception of plexin homology (FIG. 10A). Both W10-R2-1 and W10-R3-18 which have no homology to each other share homology in the extracellular domains of plexin B1/B3 and plexin B2 respectively, and W10-R3-18 also shares homology in the plexin binding domain of semaphorin3C (FIG. 10B).

Example 6: Immunofluorescent Staining of Bound Phage

The binding specificity of selected phages was determined by immunofluorescent staining of bound phage to the surface of W10 progenitor cell line. Cells were plated at 100,000 cells/well in 24 well plates and incubated overnight. Phages at $2 \times 10^{10}$ pfu/well were diluted in 0.5 ml of W10 growth media supplemented with 2% BSA and incubated with live cells for 2 h at 37° C. Cells were washed as for the selection experiments and fixed by 4% paraformaldehyde for 20 min at RT. Cells were washed twice with PBS and permeabilized by ice-cold MeOH for 15 min on ice. After another two washes, cells were blocked with 5% goat serum in 2% BSA in PBS for 1 h at RT or overnight at 4° C. Cells were incubated with 1:700 dilution of rabbit anti-Fd bacteriophage antibody (Sigma, B7786) in 2% BSA in PBS for 1 h at RT. Cells were washed with 2 ml of 1% BSA in PBS three times, and incubated with 1:1000 dilution of goat anti-rabbit AlexaFluor568 conjugated antibody (Invitrogen, A11011) in 1% BSA in PBS for 1 h at RT. Cells were counterstained with DAPI at 0.1 µg/ml after final washes and photographed by an Olympus IX71 fluorescence microscope. Images were taken and processed using MetaMorph (version 7.5.6.0, Molecular Devices), ImageJ (version 1.45b, National Institute of Health) or Photoshop (version 9.0.2, Adobe) software.

Figure 3A:
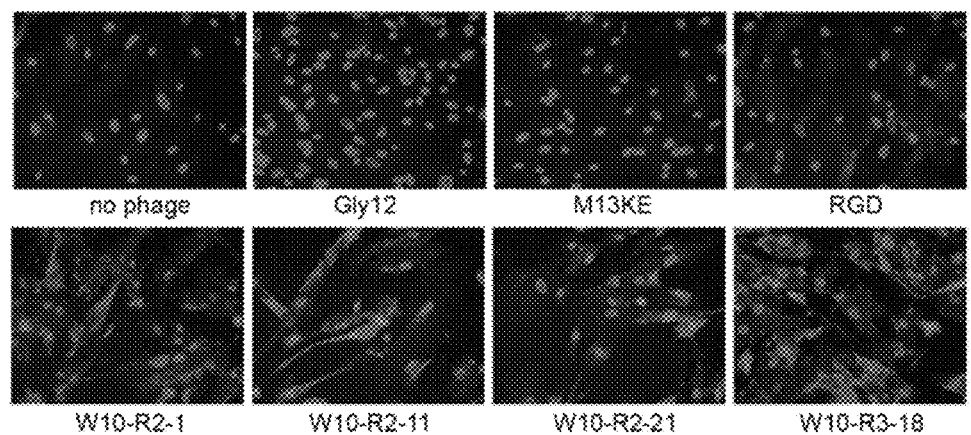
FIG. 3A and FIG. 3B. Binding of peptide display phages to W10 embryonic progenitor cell line.

Sixteen of the candidate peptide phages were analyzed (FIG. 2C) for binding to undifferentiated W10 cells using conditions similar to that used for phage library selection. The peptide phages with the strongest binding as detected by immunocytochemical staining (W10 R2 1, W10 R2 11, W10 R2 21 and W10 R3 18) are shown in FIG. 3A. Little or no binding was detected for the control M13KE phage (no displayed peptide) or Gly12 control phage, which displayed a 12-mer glycine repeat peptide (FIG. 3A) Immunostaining by the 4 peptide phages was stronger than a peptide phage displaying a RGD integrin binding peptide (i.e. peptide 10 shown in Table 1 of Holig et al. (2004) Protein Eng Des Sel 17: 433).

Example 7: Binding Factor Determination

Phage binding to W10 progenitor cell line was quantified by titration. Cells were plated at 100,000 cells/well in 24 well plates and incubated overnight. Phages at $2 \times 10^{10}$ pfu/well were diluted in 0.5 ml of W10 growth media supplemented with 2% BSA and incubated with live cells for 2 h at 37° C. Cells were washed as for the biopanning experiments; lysis buffer was added directed to the plated cells (100 µl per well) and incubated for at least 1 h on ice. Cells were scraped from the plate with the aid of a P200 tip, transferred to microcentrifuge tubes and lysate was cleared by centrifugation (18,000 g for 5 min at 4° C.). Cleared lysates were titrated by standard protocols using sequential dilutions prepared in PBS. Lysate protein concentration was measured using the Pierce microBCA assay (Thermo Scientific, Rockford, Ill.) using the 96 well plate format according to manufacturer's instructions. The relative binding factor was calculated as the ratio between the recovery (output/input) per µg of protein for the candidate phage and the M13KE control phage. Duplicate independent experiments were performed for binding factor determination.

Figure 3B:
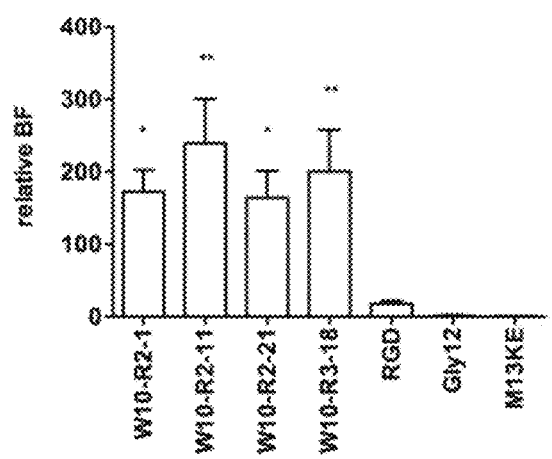

Binding of peptide phages to W10 cells was quantified by measuring the percentage of input phages retained in the cell lysate following incubation of the cells with the phage at 37° C. The binding factor (BF) was calculated as the ratio of the percentage input recovered for each candidate phage to the percentage of input recovered using M13KE control phage. All 4 peptide phages showed similarly strong W10 binding, with BFs that were statistically different from that of the control phage M13KE; BFs for RGD and Gly12 phages were not significantly different from the M13KE control (FIG. 3B).

Example 8: Peptide Competition for Phage Binding

Cells were plated at 100,000 cells/well in 24 well plates and incubated overnight. The corresponding synthetic peptide for each peptide phage or control peptides (unrelated or scrambled sequence peptide) were pre-incubated with cells at 5 nM or 5 µM in W10 growth media supplemented with 2% BSA for 30 min at 4° C. Peptide phages at $2 \times 10^{10}$ pfu/well were added to the peptide dilution and incubated with live cells for 1 h at 4° C. Peptide phage bound to cells was detected by immunostaining and fluorescence microscopy using anti-phage antibody on fixed and permeabilized cells or quantified by titration of phages recovered from cell lysates. The percentage of recovered phage for the competition assay was normalized by the recovered phage in the no-peptide control. Duplicate independent experiments were performed for competition experiments.

Figure 4A:
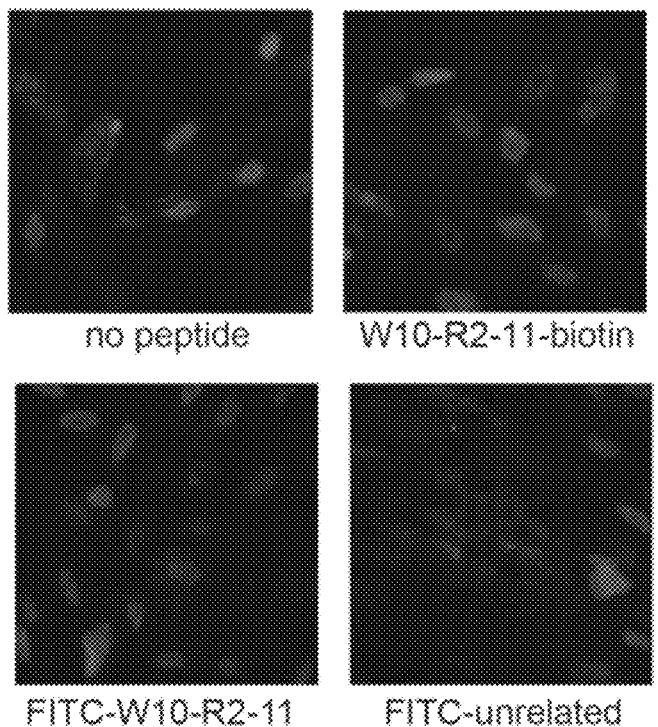
FIG. 4A and FIG. 4B. Phage binding competition with free peptide. Competition of the peptide phage with free peptide was measured using
Figure 4B:
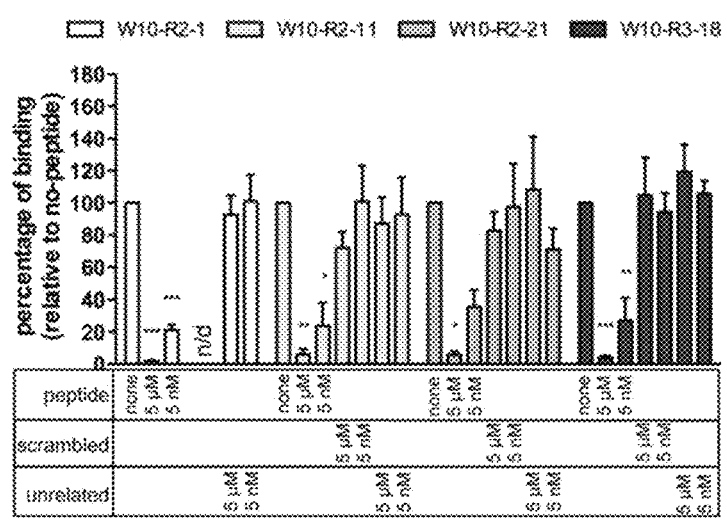

We determined the specificity of peptide phage cell binding for the displayed peptide by performing competition experiments with synthetic peptides to indirectly measure the ability of the free peptide to bind the surface of W10 cells. The degree of phage binding following pre-incubation with free peptide was initially assessed by immunofluorescent phage staining. Competition experiments were performed at 4° C. so that competition for phage binding to the cell surface could be detected in the absence of phage internalization. This resulted in a reduced phage signal compared to incubation at 37° C. presumably because of the limited accumulation of internalized phage at 4° C. Representative images of W10 R2 11 surface bound phage for no peptide control and competing W10-R2-11 peptides (100 µM) are shown in FIG. 4A. The N-terminal FITC-labeled peptide failed to compete with phage for binding to W10 cells. In contrast, the C-terminal biotinylated peptide successfully competed with the peptide phage. Control competition experiments with an unrelated FITC-labeled peptide indicated that the competition observed was specific. When C-terminal FITC-labeled version of the peptide was tested in similar competition experiments, the peptide was able to compete with the phage for binding to W10 cells (data not shown). These data indicate that a free N-terminus was necessary for binding to the same W10 surface molecule that is recognized by the peptide phages. We therefore performed further competition studies using C-terminal biotinylated peptides that can be linked to a variety of labeling moieties for targeted cell labeling. For these experiments the competition for peptide phage binding was quantified by measuring the percentage of input phages that were recovered from the cell lysate (FIG. 4B). All 4 W10 selected peptides were able to compete with the equivalent peptide phages for binding to W10 cells. At concentrations as low as 5 nM, competition by 3 of the 4 peptides was statistically significant at $p<0.05$ (W10-R2-21 was the exception). Higher concentrations of competing peptide (5 µM) resulted in statistically significant competition by all 4 peptides ($p<0.05$). Scrambled or unrelated peptides did not compete effectively at either concentration (not statistically significant). We demonstrated specificity of the W10 selected peptides by competition experiments with the free peptides. The competition experiments demonstrated that free peptide could compete for peptide phage binding at concentrations as low as 5 nM indicating that the targeting peptides have high affinity for their cognate cell surface antigens. The lack of competition with scrambled peptides indicated that the binding for W10-R2-11, W10-R2-21 and W10-R3-18 peptides is sequence specific and not a result of non-specific interactions. Failure of the N-terminal FITC labeled peptides to compete for peptide phage binding indicated the need to replicate the free N-terminus of the peptides that is present when the peptides are displayed as fusion to the phage pIII coat protein. These data indicate that cell surface binding of the 4 selected peptides was sequence specific and independent of display on the phage particle.

Example 9: Cell Labeling with Peptide Targeted Qdot Complexes

2 µM of Qdot Streptavidin conjugate (Qdot605 ITK SA, Invitrogen, Q10001MP) were diluted in 100 µl of binding buffer (supplied with Qdot605 ITK SA) and incubated with 100-fold excess of biotinylated peptide on ice for 1 h. Uncoupled biotinylated peptide was removed from the mixture by incubating it with streptavidin magnetic beads equilibrated in PBS on ice for 30 min; placing the mixture on a magnetic stand to separate the beads and removed the complexes in solution. SA-beads were washed with PBS and combined with the recovered complexes. For control reactions, Qdots were incubated with binding buffer and treated in similar way as the peptide complexes. The concentration of Qdot-peptide complexes was estimated based on the final volume recovered. To label cells with the Qdot-complexes, 100,000 cells were plated on gelatin-coated wells of 24 well plates were incubated for 6 hours; 5 nM of Qdot-peptides in growth media was added to the cells and incubated for 16 h at 37° C. Cells were imaged after washes with PBS to remove the unbound Qdot-complexes.

Figure 5A:
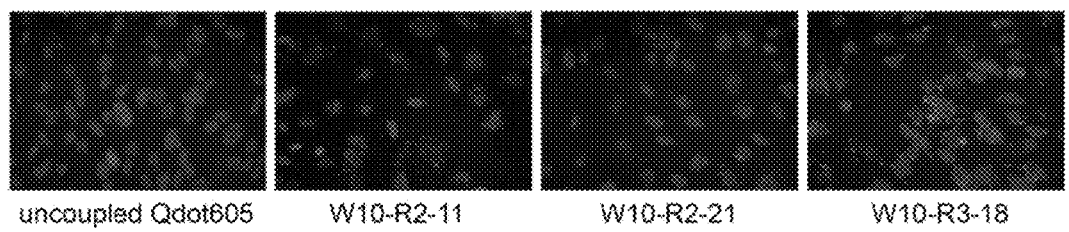
FIG. 5A through FIG. 5C. Labeling of embryonic progenitor cell line using peptide targeted Qdot605.

We initially attempted to label embryonic progenitor cells using monomeric C-terminal FITC labeled peptides. However, the resulting cell labeling was minimal even at concentrations as high as 100 μM. The poor cell labeling could be due to low signal strength and/or limited internalization of the monomeric peptide because the same peptide successfully competed with peptide phage for cell binding. Accordingly, we chose to use multivalent peptide targeted Qdots to replicate both the high valency and sensitivity obtained using peptide targeted phage particles. Streptavidin conjugated CdSe-ZnS quantum dots (Qdots) were used to form complexes with the C-terminal biotinylated peptides. Qdots typically contain 5-10 streptavidin molecules bound per Qdot each of which can bind up to 4 peptides resulting in multivalent display of 20-40 peptides per Qdot. W10 cells were incubated with W10 peptide-Qdot complexes and cell labeling detected by fluorescence microscopy. Efficient cell labeling was obtained using overnight incubation at estimated concentrations of 5 nM. These conditions resulted in little or no cell labeling using untargeted Qdots (FIG. 5A).

Figure 5B:
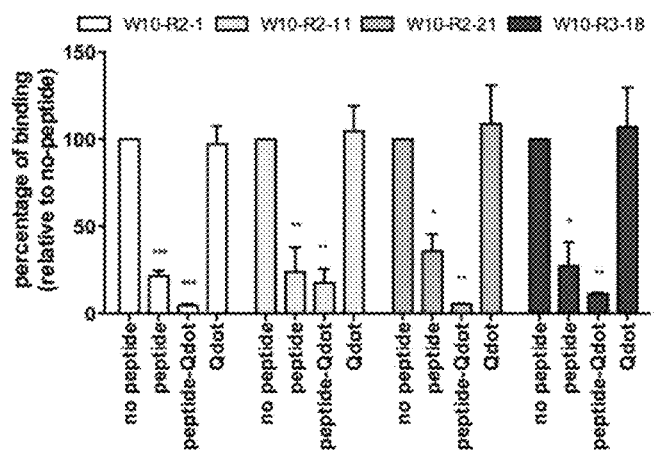

Competition experiments were used to indirectly determine the ability of the targeted Qdot complexes to bind W10 progenitor cells and to compare multivalent Qdot complexes with monomeric peptides (FIG. 5B). The peptide targeted Qdot complexes successfully competed with the equivalent peptide phages for binding to W10 progenitor cells, resulting in a 80% to 95% reduction in cell binding compared to binding in the absence of competing peptide (p<0.05). Both monomer peptide and multivalent Qdot complexes competed effectively for peptide phage binding at 5 nM (>65% inhibition; p<0.05). Competition by any of the 4 peptides did not differ significantly from competition by the equivalent peptide Qdot complex (ANOVA analysis). These data indicate that differences in cell labeling between monomer peptide and multivalent Qdots may be the result of more efficient internalization by the peptide Qdot complexes rather than differences in binding. The untargeted Qdots, at the same concentration as peptide-Qdot complexes were not statistically different from the no-peptide control indicating that the peptide-Q-dot complex competition was dependent on the presence of the peptide.

Figure 5C:
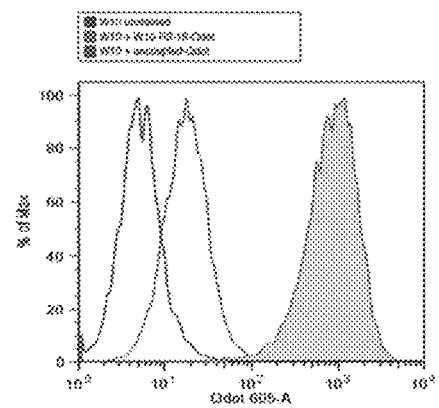
Figure 6:
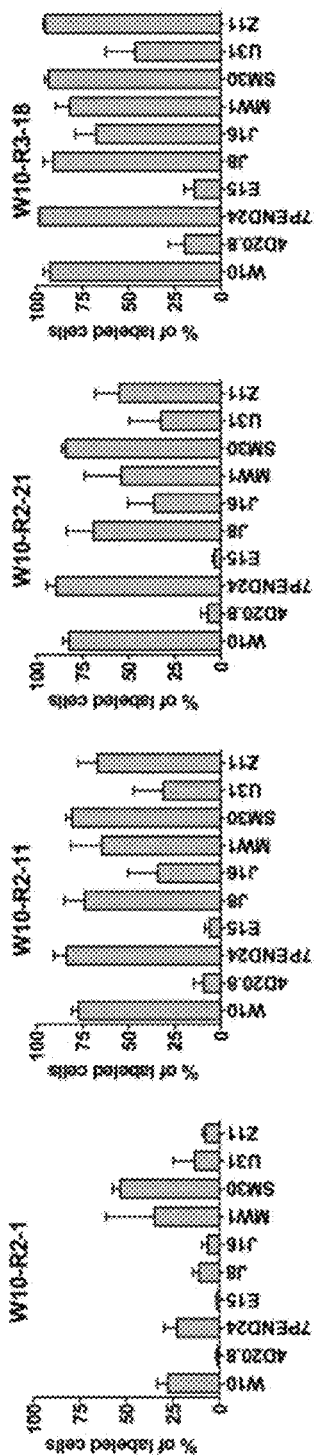
FIG. 6. Selectivity of Qdot peptide complexes. Embryonic progenitor cell lines were labeled with Qdot complexes in their corresponding growth media and analyzed by flow cytometry as in (FIG. 5C). Percentage of labeled cells was calculated by setting up gates (allowing up to 1%) using the progenitor cell line labeled with untargeted Qdots and unlabeled cells. 10,000 events were recorded for each sample. Values are from triplicate experiments and shown as mean+/−standard error.

Cell targeted Qdots are useful reagents for labeling cells for both quantitative analysis and cell separation by flow cytometry. With this application in mind, we tested the peptide-Qdot complexes for their ability to label W10 cells for flow cytometry. Results showed a strong fluorescent shift of W10 cells labeled with W10 R3 18 Qdot complexes compared to cells labeled under similar conditions with untargeted Qdots (FIG. 5C). Using flow cytometric analysis (see Example 2, above), the percentage of cells that took up the Qdot complexes was determined. Cells treated with untargeted Qdots were used for gating (FIG. 5C). The percentage of W10 cells labeled with peptide-Qdot complexes ranged from 90% for W10 R3 18 to >75% for W10 R2 21 and W10 R2 11 to 30% for W10 R2 1 (FIG. 6). These data were consistent with the rank order of peptide-Qdot cell labeling observed by fluorescence microscopy.

Peptide selectivity for embryonic progenitor cell lines: The selectivity of the peptides for W10 cells was assessed by comparing targeted Qdot labeling of W10 cells with 9 other embryonic progenitor cell lines that have been shown to be distinct cell types by genome expression profiling (West et al. (2008) *Regen Med* 3: 287. The percentage of cells labeled by the peptide targeted Qdots was measured by flow cytometry (see Example 2, above) (FIG. 6 and Supplemental FIG. 8). All 4 peptides showed some degree of selective cell targeting. The W10 R3 18 peptide, which was most efficient labeling peptide for W10 cells, was the most promiscuous cell targeting peptide. It bound to a high percentage of cells in 7 out of the 10 embryonic progenitor cell lines. The selective labeling profiles of W10 R2 11 and W10 R2 21 peptides were very similar to each other, with very little labeling of 2 clonal progenitor lines, 4D20.8 and E15, and a high percentage binding of the 7PEND24 cell line. Indeed, these 2 peptides share sequence identity at positions 1 and 2 (G, W), have strongly conserved residues at position 5 and 11 (D/E, M/F) and weakly conserved residues in the last position (R/N). Competition experiments showed that these 2 peptides can compete with each other for W10 cell binding (not shown). Taken together, these data suggest that the 2 peptides might bind the same cell surface epitope. More restricted cell labeling was observed with W10 R2 1 Qdot complexes. Of the 10 clonal progenitor lines tested, only W10, 7PEND24, SM30 and MW1 cell lines showed more than 15% cell labeling and no complex uptake was observed for E15 and 4D20.8 cells. The labeling of different embryonic progenitor cell lines gave an indication of the selectivity of the peptides complexes. While the binding is not exclusive to the W10 cell line they were selected on, there was a difference in the pattern of progenitor cell line targeting depending on the peptide sequence.

Several reports have shown that functionalized Qdots do not cause any deleterious effects on cell survival in vitro (Slotkin et al. (2007) *Dev Dyn* 236: 3393; Jaiswal et al. (2003) *Nat Biotechnol* 21: 47) and that the delivery of Qdots by electroporation or lipofection does not disrupt early stages of mammalian development or early embryogenesis nor adversely affect embryonic stem cell viability, proliferation or differentiation (Lin et al. (2007) *BMC Biotechnol* 7: 67). Here, we have demonstrated selective cell labeling using peptide targeted Qdots and determined the percentage of labeling of live cells by flow cytometry. The peptide Qdot cell labeling was not exclusive to W10 cells but was shared to various degrees with other progenitor cell lines with little or no cell labeling of 2 lines (E15 and 4D20.8). Interestingly, these 2 cell lines share a common derivation pathway that is distinct from the other lines (West et al. (2008) *Regen Med* 3: 287). These data indicate that the targeting of W10 selected peptide was restricted to certain progenitor cell types but was not limited the smooth muscle progenitor cell line. A significant advantage of identifying peptides that can target Qdots to live cells is that they could potentially be used for labeling and isolating viable hPS derived differentiating stem cells for further culture and characterization. For example, this approach could be used to characterize the small fraction of hPS derived mesodermal cells that were labeled by peptide targeted Qdots. The persistence of the Qdot signal could also be used for progenitor cell tracking during differentiation of hPS cells to determine cell fate. The peptides could also be used to target magnetic particles as an alternative approach for separating cells using magnetic activated cells sorting which has been used successfully for preclinical and clinical cell transplant applications (Grutzkau A, Radbruch A (2010) *Cytometry* A 77: 643).

Example 10: Differentiation of Cell Lineages Representing 3 Germ Layers

For ectoderm differentiation conditions, embryoid bodies (EBs) were formed from colonies by manual techniques and grown in complete NPC media (DMEM-F12:Neurobasal media 1:1+50 µl/ml BIT9500 Serum substitute (Stemgent)+1% GlutaMax+1% penicillin-streptomycin+1 µl/ml B27 supplement (Invitrogen)+5 mM nicotinamide+5 µg/ml insulin+20 ng/ml EGF+20 ng/ml bFGF) in low attachment plates for 6 days; EBs were then plated on fibronectin-coated wells and grown for another 3 days. For mesoderm differentiation conditions, EBs were cultured as above except that media was DMEM-F12 with GlutaMax+20% FBS+1% NEAA+1% penicillin-streptomycin, and plated on 0.1% gelatin-coated wells. For endodermal differentiation conditions, undifferentiated H9 cells were transferred from colonies growing with MEFs to Geltrex™ (Life Technologies, Grand Island, N.Y.)-coated wells and grown for 2 days with MEF-conditioned media+4 ng/ml bFGF. From day 2, cells were grown for another 5 days in RPMI+0.5% FBS+100 ng/ml Activin A.

The cells were analyzed as described in the next example.

Example 11: Immunofluorescent Detection of Differentiation Markers

To confirm lineage commitment of cells differentiated under different conditions, cells were washed with PBS and fixed with 4% p-formaldehyde for 20 min at RT. After three washes with PBS, cells were permeabilized and blocked using 5% serum (goat or donkey, depending on primary antibody)+1% BSA+0.3% Triton X-100 in PBS for 1 h at RT. Primary antibodies were diluted in 1% BSA+0.3% Triton X-100 in PBS and incubated overnight 4° C. Antibodies and dilutions used are as follows: nestin (Abcam, Ab22035) at 1:200, α-actinin (Sigma, A7811) at 1:200 dilution, SOX17 (Santa Cruz, sc-17355) at 1:400 dilution, OCT3/4 (R&D Systems, AF1759) at 1:200 dilution, or MYH11 antibody (Biomedical Technologies Inc., BT-562) at 1:300 dilution. After three washes with PBS, cells were incubated with secondary antibody dilutions (1:750) in 1% BSA+0.3% Triton X-100 in PBS for 1 h at RT. Antibodies conjugated to AlexaFluor 568 were donkey anti-goat (Invitrogen, A11057), goat anti-mouse (Invitrogen, A11004) or donkey anti-rabbit (Invitrogen, A10042) depending on primary antibody. Cells were counterstained with DAPI at 0.1 µg/ml for 15 min at RT.

Figure 7A:
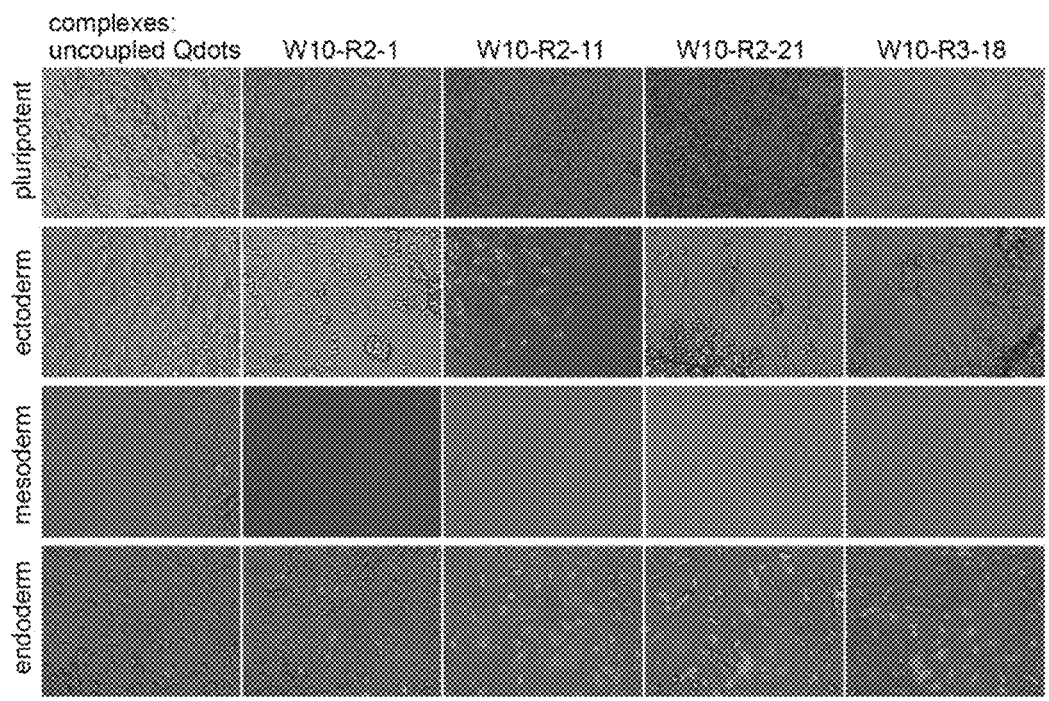
FIG. 7A and FIG. 7B. Labeling of a differentiating pluripotent stem cells using peptide targeted Qdots.
Figure 7B:
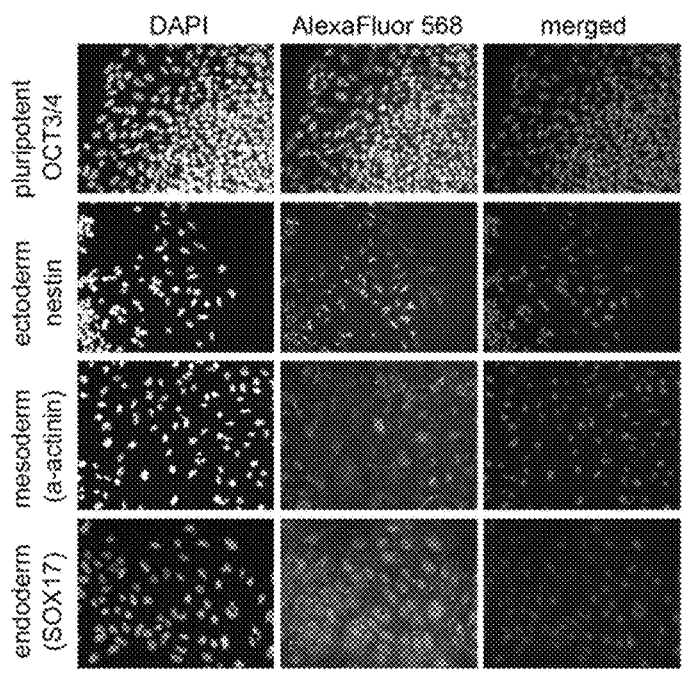
Figure 8A:
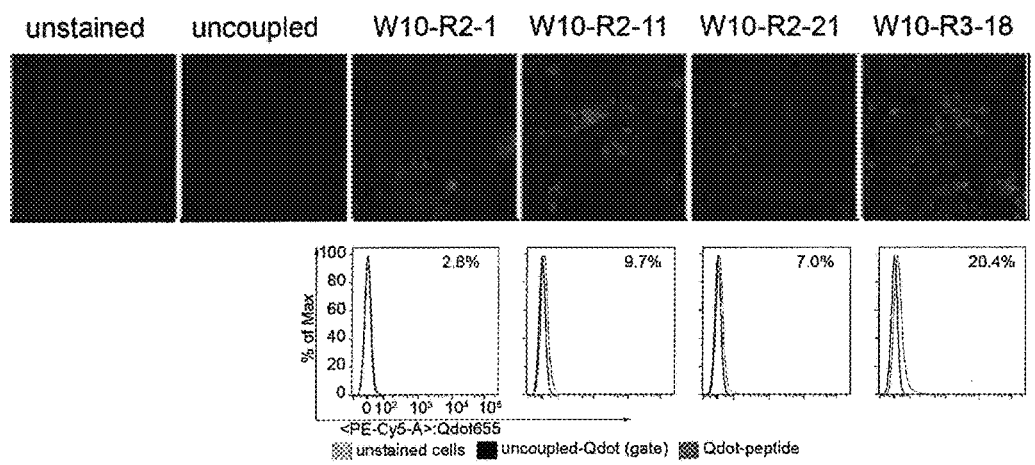
FIG. 8A through FIG. 8E. Selectivity of Qdot peptide complexes.
Figure 8A:
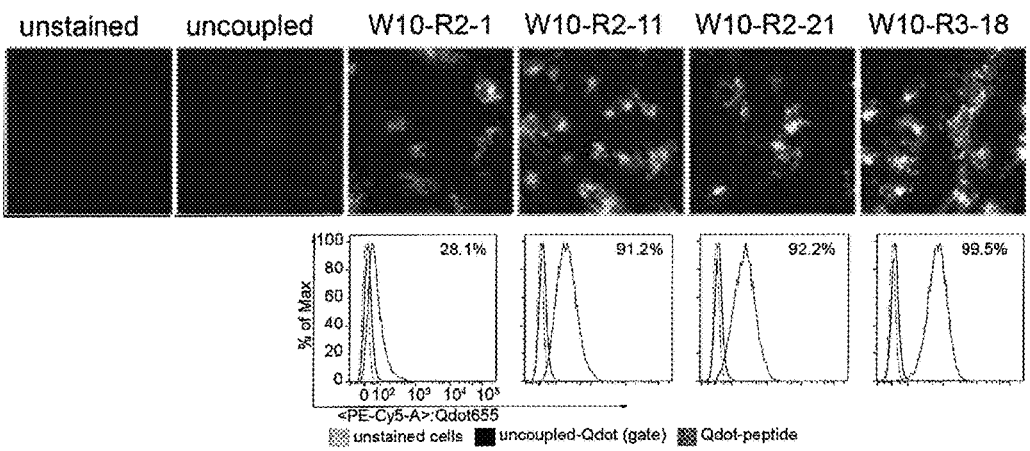
Figure 8B:
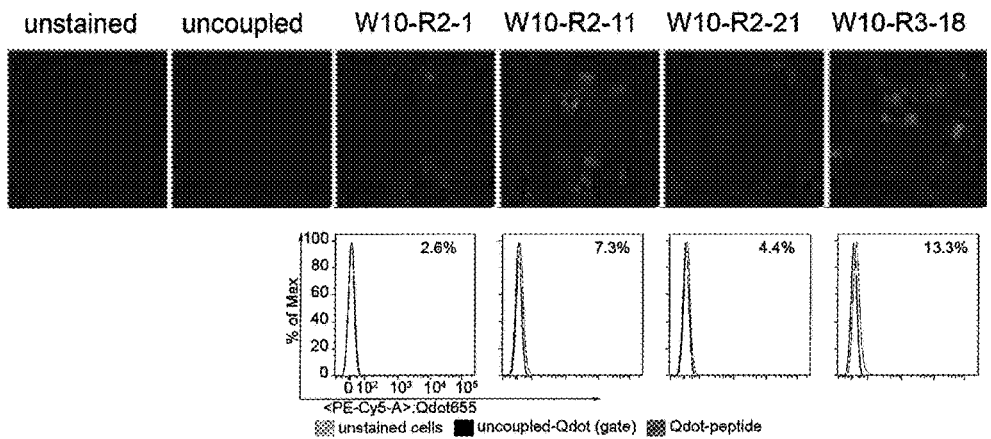
Figure 8B:
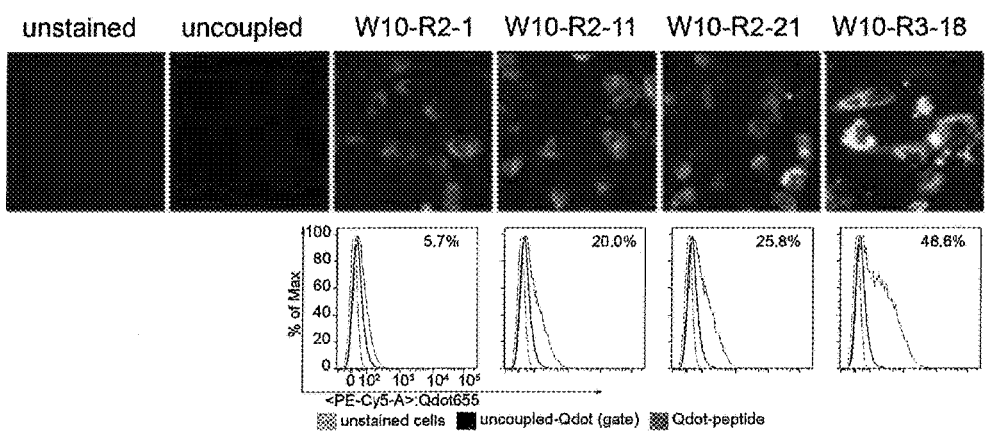
Figure 8C:
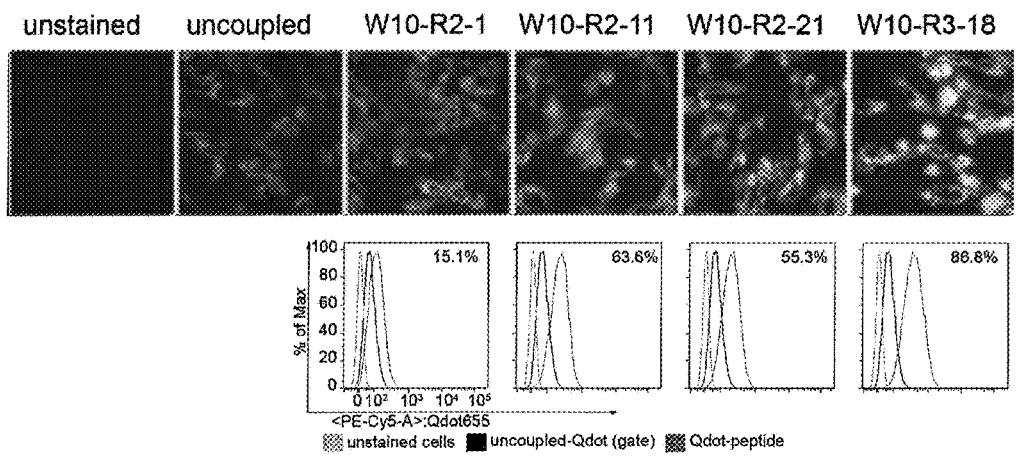
Figure 8C:
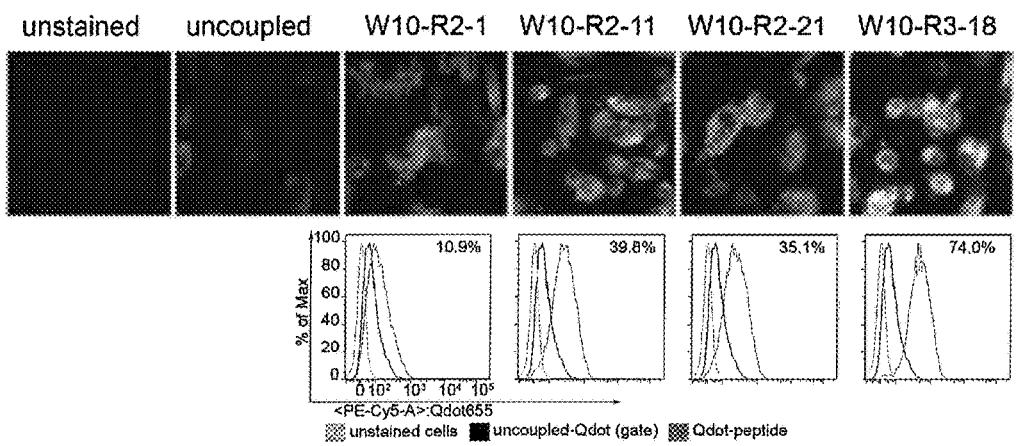
Figure 8D:
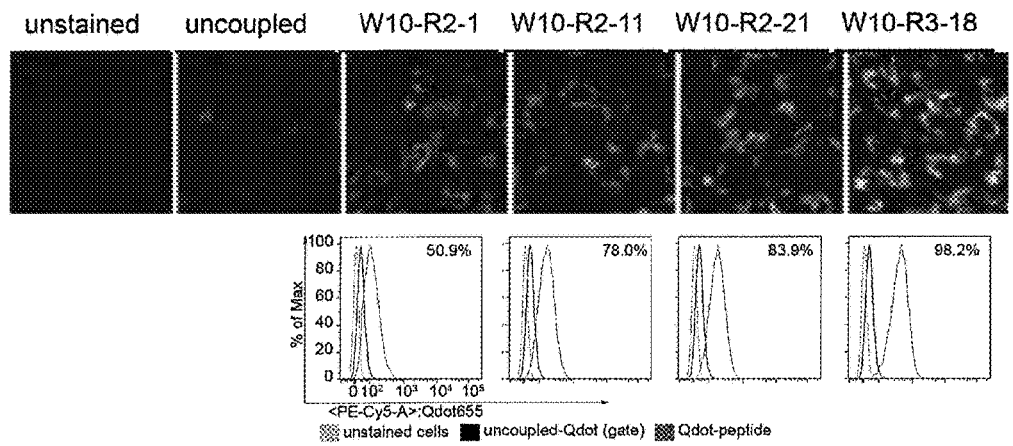
Figure 8D:
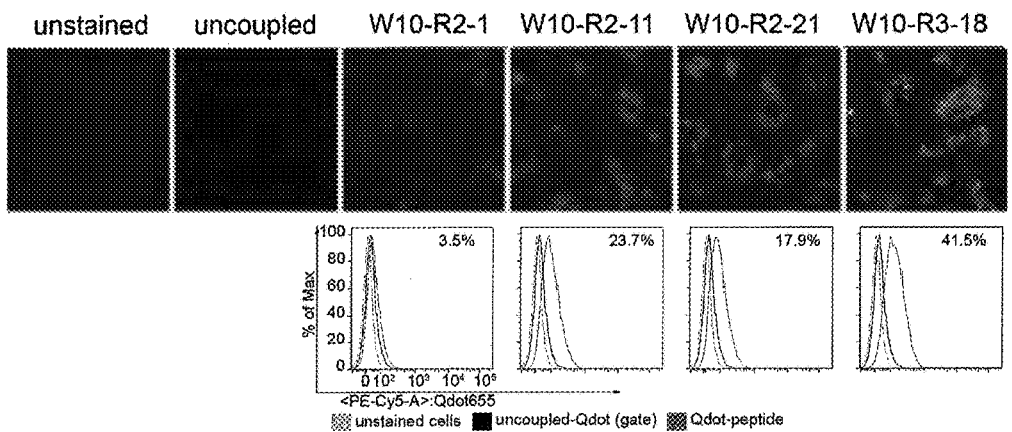
Figure 8E:
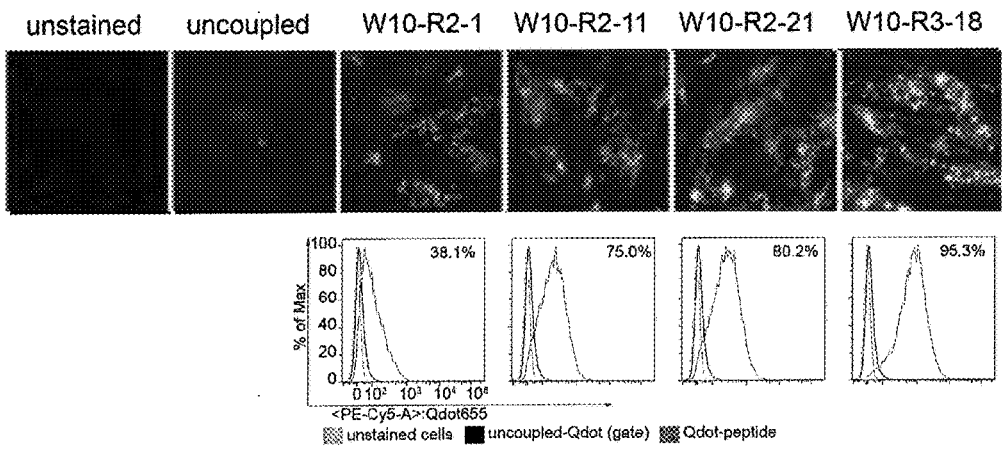
Figure 8E:
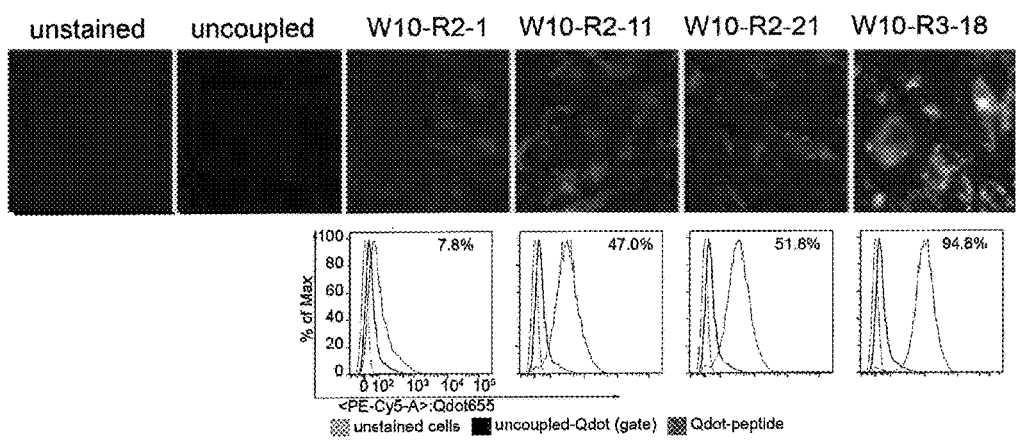

We tested the W10 cell selected peptides for selective targeting of embryonic progenitors that appear in early differentiating hPS cultures under 3 different growth conditions that promote differentiation toward ectoderm, mesoderm or definitive endoderm (FIG. 7). Importantly, W10-peptide complexes did not label undifferentiated H9 cells indicating that they are indeed selective for differentiated cells. Little or no cell labeling was observed when hPS cells were grown under ectoderm differentiation conditions for any of the 4 different peptide-Qdots complexes. Cell labeling was highly restricted, resulting in a few small patches of labeled cells, for hPS cells grown under mesoderm differentiation conditions and incubated with W10 R2 11, W10 R2 21 and W10 R3 18 targeted Qdot complexes but no labeling was observed with W10 R2 1 (FIG. 7A). In contrast, a high percentage of cells were labeled when hPS cells were differentiated using culture conditions for definitive endoderm (high activin A, low serum) and incubated with W10 R2 11, W10 R2 21 and W10 R3 18 targeted Qdot complexes. In contrast, cell labeling was highly restricted to a small percentage of cells when the endoderm differentiated cells were incubated with W10 R2 1 complexes. The hPS cells that were differentiated under the same 3 conditions were not labeled by incubation with untargeted Qdots indicating that in each case the cell labeling was dependent on the targeting peptide (FIG. 7A). Immunostaining with differentiation specific markers was used to confirm differentiation toward the appropriate lineage fate (FIG. 7B). Taken together, these data indicate that the W10 selected cell targeting peptides are capable of distinguishing between different types of embryonic progenitor cells with a marked preference for targeting early definitive endodermal progenitor cells.

What is claimed is:

1. A method of enriching a population of progenitor cells, wherein the progenitor cells are the in vitro progeny of pluripotent stem cells, comprising contacting a population of cells comprising a progenitor cell with a peptide that binds specifically to the progenitor cell, wherein the peptide is chosen from SWTYSYPNQNMD (SEQ ID NO: 1); DWTYSLPGLVEE (SEQ ID NO: 2); NWTWSMPTGNPA (SEQ ID NO: 3); GMTLRVLTN-YTE- (SEQ ID NO: 4); TLHVSENSWTYN (SEQ ID NO: 5); DWLWSFAPNVDT (SEQ ID NO: 6); TLSSQNPYMHKK (SEQ ID NO: 7); IDKQMMTSHKAI (SEQ ID NO: 8); QGMETQKLRMLK (SEQ ID NO: 9); GWYWETPLDMFN (SEQ ID NO: 10); GWVIDYDYYPMR (SEQ ID NO: 11); VTAENYQSFSVS (SEQ ID NO: 12); NNKMDDRMMMSIV (SEQ ID NO: 13); STGTDLHSNARI (SEQ ID NO: 14); YEFDNLLNRTLW (SEQ ID NO: 15); EWTVNERTMWDL (SEQ ID NO: 16), and separating the progenitor cell bound to the peptide from the population of cells thereby enriching for a population of progenitor cells.

2. The method of claim 1, wherein the progenitor cell is a human cell.

3. The method of claim 2 wherein the progenitor cell is an endoderm cell.

4. The method of claim 2, wherein the progenitor cell is a mesoderm cell.

5. The method of claim 2, wherein the progenitor cell is a W10 progenitor cell.

6. The method of claim 1, wherein the progenitor cell expresses the markers heart and neural crest derivatives-expressed 2 (HAND2), HOXA4 and HOXB7, and wherein the peptide binds specifically to the progenitor cell expressing HAND2, HOXA4 and HOXB7 proteins.

7. The method of claim 1, wherein the peptide has plexin homology.

* * * * *

SEQUENCE LISTING

```
<160> NUMBER OF SEQ ID NOS: 75

<210> SEQ ID NO 1
<211> LENGTH: 12
<212> TYPE: PRT
<213> ORGANISM: Artificial Sequence
<220> FEATURE:
<223> OTHER INFORMATION: FROM PHAGE DISPLAY LIBRARY

<400> SEQUENCE: 1

Ser Trp Thr Tyr Ser Tyr Pro Asn Gln Asn Met Asp
1               5                   10

<210> SEQ ID NO 2
<211> LENGTH: 12
<212> TYPE: PRT
<213> ORGANISM: Artificial Sequence
<220> FEATURE:
<223> OTHER INFORMATION: FROM PHAGE DISPLAY LIBRARY

<400> SEQUENCE: 2
```

Asp Trp Thr Tyr Ser Leu Pro Gly Leu Val Glu Glu
1               5                   10

<210> SEQ ID NO 3
<211> LENGTH: 12
<212> TYPE: PRT
<213> ORGANISM: Artificial Sequence
<220> FEATURE:
<223> OTHER INFORMATION: FROM PHAGE DISPLAY LIBRARY

<400> SEQUENCE: 3

Asn Trp Thr Trp Ser Met Pro Thr Gly Asn Pro Ala
1               5                   10

<210> SEQ ID NO 4
<211> LENGTH: 12
<212> TYPE: PRT
<213> ORGANISM: Artificial Sequence
<220> FEATURE:
<223> OTHER INFORMATION: FROM PHAGE DISPLAY LIBRARY

<400> SEQUENCE: 4

Gly Met Thr Leu Arg Val Leu Thr Asn Tyr Thr Glu
1               5                   10

<210> SEQ ID NO 5
<211> LENGTH: 12
<212> TYPE: PRT
<213> ORGANISM: Artificial Sequence
<220> FEATURE:
<223> OTHER INFORMATION: FROM PHAGE DISPLAY LIBRARY

<400> SEQUENCE: 5

Thr Leu His Val Ser Glu Asn Ser Trp Thr Tyr Asn
1               5                   10

<210> SEQ ID NO 6
<211> LENGTH: 12
<212> TYPE: PRT
<213> ORGANISM: Artificial Sequence
<220> FEATURE:
<223> OTHER INFORMATION: FROM PHAGE DISPLAY LIBRARY

<400> SEQUENCE: 6

Asp Trp Leu Trp Ser Phe Ala Pro Asn Val Asp Thr
1               5                   10

<210> SEQ ID NO 7
<211> LENGTH: 12
<212> TYPE: PRT
<213> ORGANISM: Artificial Sequence
<220> FEATURE:
<223> OTHER INFORMATION: FROM PHAGE DISPLAY LIBRARY

<400> SEQUENCE: 7

Thr Leu Ser Ser Gln Asn Pro Tyr Met His Lys Lys
1               5                   10

<210> SEQ ID NO 8
<211> LENGTH: 12
<212> TYPE: PRT
<213> ORGANISM: Artificial Sequence
<220> FEATURE:
<223> OTHER INFORMATION: FROM PHAGE DISPLAY LIBRARY

<400> SEQUENCE: 8

Ile Asp Lys Gln Met Met Thr Ser His Lys Ala Ile

```
<210> SEQ ID NO 9
<211> LENGTH: 12
<212> TYPE: PRT
<213> ORGANISM: Artificial Sequence
<220> FEATURE:
<223> OTHER INFORMATION: FROM PHAGE DISPLAY LIBRARY

<400> SEQUENCE: 9

Gln Gly Met Glu Thr Gln Lys Leu Arg Met Leu Lys
1               5                   10

<210> SEQ ID NO 10
<211> LENGTH: 12
<212> TYPE: PRT
<213> ORGANISM: Artificial Sequence
<220> FEATURE:
<223> OTHER INFORMATION: FROM PHAGE DISPLAY LIBRARY

<400> SEQUENCE: 10

Gly Trp Tyr Trp Glu Thr Pro Leu Asp Met Phe Asn
1               5                   10

<210> SEQ ID NO 11
<211> LENGTH: 12
<212> TYPE: PRT
<213> ORGANISM: Artificial Sequence
<220> FEATURE:
<223> OTHER INFORMATION: FROM PHAGE DISPLAY LIBRARY

<400> SEQUENCE: 11

Gly Trp Val Ile Asp Tyr Asp Tyr Tyr Pro Met Arg
1               5                   10

<210> SEQ ID NO 12
<211> LENGTH: 12
<212> TYPE: PRT
<213> ORGANISM: Artificial Sequence
<220> FEATURE:
<223> OTHER INFORMATION: FROM PHAGE DISPLAY LIBRARY

<400> SEQUENCE: 12

Val Thr Ala Glu Asn Tyr Gln Ser Phe Ser Val Ser
1               5                   10

<210> SEQ ID NO 13
<211> LENGTH: 13
<212> TYPE: PRT
<213> ORGANISM: Artificial Sequence
<220> FEATURE:
<223> OTHER INFORMATION: FROM PHAGE DISPLAY LIBRARY

<400> SEQUENCE: 13

Asn Asn Lys Met Asp Asp Arg Met Met Met Ser Ile Val
1               5                   10

<210> SEQ ID NO 14
<211> LENGTH: 12
<212> TYPE: PRT
<213> ORGANISM: Artificial Sequence
<220> FEATURE:
<223> OTHER INFORMATION: FROM PHAGE DISPLAY LIBRARY

<400> SEQUENCE: 14

Ser Thr Gly Thr Asp Leu His Ser Asn Ala Arg Ile
1               5                   10
```

```
<210> SEQ ID NO 15
<211> LENGTH: 12
<212> TYPE: PRT
<213> ORGANISM: Artificial Sequence
<220> FEATURE:
<223> OTHER INFORMATION: FROM PHAGE DISPLAY LIBRARY

<400> SEQUENCE: 15

Tyr Glu Phe Asp Asn Leu Leu Asn Arg Thr Leu Trp
1               5                   10

<210> SEQ ID NO 16
<211> LENGTH: 12
<212> TYPE: PRT
<213> ORGANISM: Artificial Sequence
<220> FEATURE:
<223> OTHER INFORMATION: FROM PHAGE DISPLAY LIBRARY

<400> SEQUENCE: 16

Glu Trp Thr Val Asn Glu Arg Thr Met Trp Asp Leu
1               5                   10

<210> SEQ ID NO 17
<211> LENGTH: 16
<212> TYPE: PRT
<213> ORGANISM: Artificial Sequence
<220> FEATURE:
<223> OTHER INFORMATION: FROM PHAGE DISPLAY LIBRARY

<400> SEQUENCE: 17

Gly Trp Val Ile Asp Tyr Asp Tyr Tyr Pro Met Arg Gly Gly Gly Lys
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: FROM PHAGE DISPLAY LIBRARY

<400> SEQUENCE: 18

Gly Trp Val Ile Asp Tyr Asp Tyr Tyr Pro Met Arg Gly Gly Gly
1               5                   10                  15

<210> SEQ ID NO 19
<211> LENGTH: 12
<212> TYPE: PRT
<213> ORGANISM: Artificial Sequence
<220> FEATURE:
<223> OTHER INFORMATION: FROM PHAGE DISPLAY LIBRARY

<400> SEQUENCE: 19

Asn His Val His Arg Met His Ala Thr Pro Ala Tyr
1               5                   10

<210> SEQ ID NO 20
<211> LENGTH: 16
<212> TYPE: PRT
<213> ORGANISM: Artificial Sequence
<220> FEATURE:
<223> OTHER INFORMATION: FROM PHAGE DISPLAY LIBRARY

<400> SEQUENCE: 20

Leu Gly Thr Met Asp Trp Phe Trp Pro Tyr Asn Glu Gly Gly Gly Gly
1               5                   10                  15
```

```
<210> SEQ ID NO 21
<211> LENGTH: 16
<212> TYPE: PRT
<213> ORGANISM: Artificial Sequence
<220> FEATURE:
<223> OTHER INFORMATION: FROM PHAGE DISPLAY LIBRARY

<400> SEQUENCE: 21

Val Ser Asp Pro Phe Asp Asn Leu Trp Thr Ala Trp Gly Gly Gly Lys
1               5                   10                  15

<210> SEQ ID NO 22
<211> LENGTH: 4
<212> TYPE: PRT
<213> ORGANISM: Artificial Sequence
<220> FEATURE:
<223> OTHER INFORMATION: FROM PHAGE DISPLAY LIBRARY

<400> SEQUENCE: 22

Asp Trp Leu Trp
1

<210> SEQ ID NO 23
<211> LENGTH: 5
<212> TYPE: PRT
<213> ORGANISM: Artificial Sequence
<220> FEATURE:
<223> OTHER INFORMATION: FROM PHAGE DISPLAY LIBRARY

<400> SEQUENCE: 23

Asp Leu Trp Ser Phe
1               5

<210> SEQ ID NO 24
<211> LENGTH: 6
<212> TYPE: PRT
<213> ORGANISM: Artificial Sequence
<220> FEATURE:
<223> OTHER INFORMATION: From phage display library

<400> SEQUENCE: 24

Trp Leu Trp Ser Phe Pro
1               5

<210> SEQ ID NO 25
<211> LENGTH: 4
<212> TYPE: PRT
<213> ORGANISM: Artificial Sequence
<220> FEATURE:
<223> OTHER INFORMATION: FROM PHAGE DISPLAY LIBRARY

<400> SEQUENCE: 25

Phe Pro Asn Val
1

<210> SEQ ID NO 26
<211> LENGTH: 5
<212> TYPE: PRT
<213> ORGANISM: Artificial Sequence
<220> FEATURE:
<223> OTHER INFORMATION: FROM PHAGE DISPLAY LIBRARY

<400> SEQUENCE: 26

Ser Phe Pro Asn Val
1               5
```

```
<210> SEQ ID NO 27
<211> LENGTH: 4
<212> TYPE: PRT
<213> ORGANISM: Artificial Sequence
<220> FEATURE:
<223> OTHER INFORMATION: FROM PHAGE DISPLAY LIBRARY

<400> SEQUENCE: 27

Pro Asn Val Thr
1

<210> SEQ ID NO 28
<211> LENGTH: 6
<212> TYPE: PRT
<213> ORGANISM: Artificial Sequence
<220> FEATURE:
<223> OTHER INFORMATION: FROM PHAGE DISPLAY LIBRARY

<400> SEQUENCE: 28

Trp Leu Trp Ser Phe Pro
1               5

<210> SEQ ID NO 29
<211> LENGTH: 4
<212> TYPE: PRT
<213> ORGANISM: Artificial Sequence
<220> FEATURE:
<223> OTHER INFORMATION: FROM PHAGE DISPLAY LIBRARY

<400> SEQUENCE: 29

Asn Leu Leu Asn
1

<210> SEQ ID NO 30
<211> LENGTH: 6
<212> TYPE: PRT
<213> ORGANISM: Artificial Sequence
<220> FEATURE:
<223> OTHER INFORMATION: FROM PHAGE DISPLAY LIBRARY

<400> SEQUENCE: 30

Tyr Phe Asn Leu Leu Asn
1               5

<210> SEQ ID NO 31
<211> LENGTH: 4
<212> TYPE: PRT
<213> ORGANISM: Artificial Sequence
<220> FEATURE:
<223> OTHER INFORMATION: FROM PHAGE DISPLAY LIBRARY

<400> SEQUENCE: 31

Leu Leu Arg Thr
1

<210> SEQ ID NO 32
<211> LENGTH: 4
<212> TYPE: PRT
<213> ORGANISM: Artificial Sequence
<220> FEATURE:
<223> OTHER INFORMATION: From phage display library

<400> SEQUENCE: 32

Asn Arg Thr Leu
1

<210> SEQ ID NO 33
```

```
<211> LENGTH: 7
<212> TYPE: PRT
<213> ORGANISM: Artificial Sequence
<220> FEATURE:
<223> OTHER INFORMATION: FROM PHAGE DISPLAY LIBRARY

<400> SEQUENCE: 33

Asn Leu Leu Asn Arg Thr Leu
1               5

<210> SEQ ID NO 34
<211> LENGTH: 9
<212> TYPE: PRT
<213> ORGANISM: Artificial Sequence
<220> FEATURE:
<223> OTHER INFORMATION: FROM PHAGE DISPLAY LIBRARY

<400> SEQUENCE: 34

Phe Asn Leu Leu Asn Arg Thr Leu Ala
1               5

<210> SEQ ID NO 35
<211> LENGTH: 9
<212> TYPE: PRT
<213> ORGANISM: Artificial Sequence
<220> FEATURE:
<223> OTHER INFORMATION: FROM PHAGE DISPLAY LIBRARY

<400> SEQUENCE: 35

Tyr Phe Asn Leu Leu Asn Arg Thr Leu
1               5

<210> SEQ ID NO 36
<211> LENGTH: 20
<212> TYPE: DNA
<213> ORGANISM: Artificial Sequence
<220> FEATURE:
<223> OTHER INFORMATION: FROM PHAGE DISPLAY LIBRARY

<400> SEQUENCE: 36
ttgtcattgt cggcgcaact                                          20

<210> SEQ ID NO 37
<211> LENGTH: 21
<212> TYPE: DNA
<213> ORGANISM: Artificial Sequence
<220> FEATURE:
<223> OTHER INFORMATION: FROM PHAGE DISPLAY LIBRARY

<400> SEQUENCE: 37
gcattccaca gacagccctc a                                        21

<210> SEQ ID NO 38
<211> LENGTH: 20
<212> TYPE: DNA
<213> ORGANISM: Artificial Sequence
<220> FEATURE:
<223> OTHER INFORMATION: FROM PHAGE DISPLAY LIBRARY

<400> SEQUENCE: 38
ccctcatagt tagcgtaacg                                          20

<210> SEQ ID NO 39
<211> LENGTH: 12
<212> TYPE: PRT
<213> ORGANISM: Artificial Sequence
<220> FEATURE:
```

<223> OTHER INFORMATION: FROM PHAGE DISPLAY LIBRARY

<400> SEQUENCE: 39

Ser Trp Thr Tyr Ser Tyr Pro Asn Gln Asn Met Asp
1               5                   10

<210> SEQ ID NO 40
<211> LENGTH: 12
<212> TYPE: PRT
<213> ORGANISM: Artificial Sequence
<220> FEATURE:
<223> OTHER INFORMATION: FROM PHAGE DISPLAY LIBRARY

<400> SEQUENCE: 40

Asp Trp Thr Tyr Ser Leu Pro Gly Leu Val Glu Glu
1               5                   10

<210> SEQ ID NO 41
<211> LENGTH: 12
<212> TYPE: PRT
<213> ORGANISM: Artificial Sequence
<220> FEATURE:
<223> OTHER INFORMATION: FROM PHAGE DISPLAY LIBRARY

<400> SEQUENCE: 41

Asn Trp Thr Trp Ser Met Pro Thr Gly Asn Pro Ala
1               5                   10

<210> SEQ ID NO 42
<211> LENGTH: 12
<212> TYPE: PRT
<213> ORGANISM: Artificial Sequence
<220> FEATURE:
<223> OTHER INFORMATION: FROM PHAGE DISPLAY LIBRARY

<400> SEQUENCE: 42

Gly Met Thr Leu Arg Val Leu Thr Asn Tyr Thr Glu
1               5                   10

<210> SEQ ID NO 43
<211> LENGTH: 12
<212> TYPE: PRT
<213> ORGANISM: Artificial Sequence
<220> FEATURE:
<223> OTHER INFORMATION: FROM PHAGE DISPLAY LIBRARY

<400> SEQUENCE: 43

Thr Leu His Val Ser Glu Asn Ser Trp Thr Tyr Asn
1               5                   10

<210> SEQ ID NO 44
<211> LENGTH: 12
<212> TYPE: PRT
<213> ORGANISM: Artificial Sequence
<220> FEATURE:
<223> OTHER INFORMATION: FROM PHAGE DISPLAY LIBRARY

<400> SEQUENCE: 44

Asp Trp Leu Trp Ser Phe Ala Pro Asn Val Asp Thr
1               5                   10

<210> SEQ ID NO 45
<211> LENGTH: 12
<212> TYPE: PRT
<213> ORGANISM: Artificial Sequence
<220> FEATURE:
<223> OTHER INFORMATION: FROM PHAGE DISPLAY LIBRARY

<400> SEQUENCE: 45

Thr Leu Ser Ser Gln Asn Pro Tyr Met His Lys Lys
1               5                   10

<210> SEQ ID NO 46
<211> LENGTH: 12
<212> TYPE: PRT
<213> ORGANISM: Artificial Sequence
<220> FEATURE:
<223> OTHER INFORMATION: From phage display library

<400> SEQUENCE: 46

Ile Asp Lys Gln Met Met Thr Ser His Lys Ala Ile
1               5                   10

<210> SEQ ID NO 47
<211> LENGTH: 12
<212> TYPE: PRT
<213> ORGANISM: Artificial Sequence
<220> FEATURE:
<223> OTHER INFORMATION: FROM PHAGE DISPLAY LIBRARY

<400> SEQUENCE: 47

Gln Gly Met Glu Thr Gln Lys Leu Arg Met Leu Lys
1               5                   10

<210> SEQ ID NO 48
<211> LENGTH: 12
<212> TYPE: PRT
<213> ORGANISM: Artificial Sequence
<220> FEATURE:
<223> OTHER INFORMATION: FROM PHAGE DISPLAY LIBRARY

<400> SEQUENCE: 48

Gly Trp Tyr Trp Glu Thr Pro Leu Asp Met Phe Asn
1               5                   10

<210> SEQ ID NO 49
<211> LENGTH: 12
<212> TYPE: PRT
<213> ORGANISM: Artificial Sequence
<220> FEATURE:
<223> OTHER INFORMATION: FROM PHAGE DISPLAY LIBRARY

<400> SEQUENCE: 49

Gly Trp Val Ile Asp Tyr Asp Tyr Tyr Pro Met Arg
1               5                   10

<210> SEQ ID NO 50
<211> LENGTH: 12
<212> TYPE: PRT
<213> ORGANISM: Artificial Sequence
<220> FEATURE:
<223> OTHER INFORMATION: FROM PHAGE DISPLAY LIBRARY

<400> SEQUENCE: 50

Val Thr Ala Glu Asn Tyr Gln Ser Phe Ser Val Ser
1               5                   10

<210> SEQ ID NO 51
<211> LENGTH: 12
<212> TYPE: PRT
<213> ORGANISM: Artificial Sequence
<220> FEATURE:
<223> OTHER INFORMATION: FROM PHAGE DISPLAY LIBRARY

```
<400> SEQUENCE: 51

Asn Asn Lys Met Ser Ser Glu Met Met Ser Ile Val
1               5                   10

<210> SEQ ID NO 52
<211> LENGTH: 12
<212> TYPE: PRT
<213> ORGANISM: Artificial Sequence
<220> FEATURE:
<223> OTHER INFORMATION: FROM PHAGE DISPLAY LIBRARY

<400> SEQUENCE: 52

Ser Thr Gly Thr Asp Leu His Ser Asn Ala Arg Ile
1               5                   10

<210> SEQ ID NO 53
<211> LENGTH: 12
<212> TYPE: PRT
<213> ORGANISM: Artificial Sequence
<220> FEATURE:
<223> OTHER INFORMATION: FROM PHAGE DISPLAY LIBRARY

<400> SEQUENCE: 53

Tyr Glu Phe Asp Asn Leu Leu Asn Arg Thr Leu Trp
1               5                   10

<210> SEQ ID NO 54
<211> LENGTH: 12
<212> TYPE: PRT
<213> ORGANISM: Artificial Sequence
<220> FEATURE:
<223> OTHER INFORMATION: FROM PHAGE DISPLAY LIBRARY

<400> SEQUENCE: 54

Glu Trp Thr Val Asn Glu Arg Thr Met Trp Asp Leu
1               5                   10

<210> SEQ ID NO 55
<211> LENGTH: 12
<212> TYPE: PRT
<213> ORGANISM: Artificial Sequence
<220> FEATURE:
<223> OTHER INFORMATION: FROM PHAGE DISPLAY LIBRARY

<400> SEQUENCE: 55

Asp Trp Leu Trp Ser Phe Ala Pro Asn Val Asp Thr
1               5                   10

<210> SEQ ID NO 56
<211> LENGTH: 12
<212> TYPE: PRT
<213> ORGANISM: Artificial Sequence
<220> FEATURE:
<223> OTHER INFORMATION: FROM PHAGE DISPLAY LIBRARY

<400> SEQUENCE: 56

Tyr Glu Phe Asp Asn Leu Leu Asn Arg Thr Leu Trp
1               5                   10

<210> SEQ ID NO 57
<211> LENGTH: 12
<212> TYPE: PRT
<213> ORGANISM: Artificial Sequence
<220> FEATURE:
<223> OTHER INFORMATION: FROM PHAGE DISPLAY LIBRARY

<400> SEQUENCE: 57
```

```
Gly Trp Tyr Trp Glu Thr Pro Leu Asp Met Phe Asn
1               5                   10
```

<210> SEQ ID NO 58
<211> LENGTH: 12
<212> TYPE: PRT
<213> ORGANISM: Artificial Sequence
<220> FEATURE:
<223> OTHER INFORMATION: FROM PHAGE DISPLAY LIBRARY

<400> SEQUENCE: 58

```
Gly Trp Val Ile Asp Tyr Asp Tyr Tyr Pro Met Arg
1               5                   10
```

<210> SEQ ID NO 59
<211> LENGTH: 7
<212> TYPE: PRT
<213> ORGANISM: Artificial Sequence
<220> FEATURE:
<223> OTHER INFORMATION: FROM PHAGE DISPLAY LIBRARY

<400> SEQUENCE: 59

```
Trp Leu Trp Asp Phe Gln Pro
1               5
```

<210> SEQ ID NO 60
<211> LENGTH: 10
<212> TYPE: PRT
<213> ORGANISM: Artificial Sequence
<220> FEATURE:
<223> OTHER INFORMATION: FROM PHAGE DISPLAY LIBRARY

<400> SEQUENCE: 60

```
Asp Phe Gln Asn Leu Leu Asn Arg Thr Leu
1               5                   10
```

<210> SEQ ID NO 61
<211> LENGTH: 6
<212> TYPE: PRT
<213> ORGANISM: Artificial Sequence
<220> FEATURE:
<223> OTHER INFORMATION: FROM PHAGE DISPLAY LIBRARY

<400> SEQUENCE: 61

```
Glu Thr Pro Leu Asp Met
1               5
```

<210> SEQ ID NO 62
<211> LENGTH: 11
<212> TYPE: PRT
<213> ORGANISM: Artificial Sequence
<220> FEATURE:
<223> OTHER INFORMATION: FROM PHAGE DISPLAY LIBRARY

<400> SEQUENCE: 62

```
Gly Trp Val Ile Tyr Lys Asp Tyr Gln Tyr Tyr
1               5                   10
```

<210> SEQ ID NO 63
<211> LENGTH: 12
<212> TYPE: PRT
<213> ORGANISM: Artificial Sequence
<220> FEATURE:
<223> OTHER INFORMATION: FROM PHAGE DISPLAY LIBRARY

<400> SEQUENCE: 63

```
Gly Trp Val Ile Asp Tyr Asp Tyr Tyr Pro Met Arg
1               5                   10
```

<210> SEQ ID NO 64
<211> LENGTH: 12
<212> TYPE: PRT
<213> ORGANISM: Artificial Sequence
<220> FEATURE:
<223> OTHER INFORMATION: FROM PHAGE DISPLAY LIBRARY

<400> SEQUENCE: 64

```
Gly Trp Tyr Trp Glu Thr Pro Leu Asp Met Phe Asn
1               5                   10
```

<210> SEQ ID NO 65
<211> LENGTH: 12
<212> TYPE: PRT
<213> ORGANISM: Artificial Sequence
<220> FEATURE:
<223> OTHER INFORMATION: From phage display library

<400> SEQUENCE: 65

```
Asp Trp Leu Trp Ser Phe Ala Pro Asn Val Asp Thr
1               5                   10
```

<210> SEQ ID NO 66
<211> LENGTH: 5
<212> TYPE: PRT
<213> ORGANISM: Artificial Sequence
<220> FEATURE:
<223> OTHER INFORMATION: From phage display library

<400> SEQUENCE: 66

```
Asp Trp Leu Trp Tyr
1               5
```

<210> SEQ ID NO 67
<211> LENGTH: 4
<212> TYPE: PRT
<213> ORGANISM: Artificial Sequence
<220> FEATURE:
<223> OTHER INFORMATION: From phage display library

<400> SEQUENCE: 67

```
Trp Leu Trp Ser
1
```

<210> SEQ ID NO 68
<211> LENGTH: 7
<212> TYPE: PRT
<213> ORGANISM: Artificial Sequence
<220> FEATURE:
<223> OTHER INFORMATION: From phage display library

<400> SEQUENCE: 68

```
Trp Leu Trp Ser Phe Gln Pro
1               5
```

<210> SEQ ID NO 69
<211> LENGTH: 8
<212> TYPE: PRT
<213> ORGANISM: Artificial Sequence
<220> FEATURE:
<223> OTHER INFORMATION: From phage display library

<400> SEQUENCE: 69

```
Ser Phe Asn Pro Asn Val Asn Thr
```

<210> SEQ ID NO 70
<211> LENGTH: 12
<212> TYPE: PRT
<213> ORGANISM: Artificial Sequence
<220> FEATURE:
<223> OTHER INFORMATION: From phage display library

<400> SEQUENCE: 70

Tyr Glu Phe Asp Asn Leu Leu Asn Arg Thr Leu Trp
1               5                   10

<210> SEQ ID NO 71
<211> LENGTH: 7
<212> TYPE: PRT
<213> ORGANISM: Artificial Sequence
<220> FEATURE:
<223> OTHER INFORMATION: From phage display library

<400> SEQUENCE: 71

Tyr Gln Phe Asn Leu Leu Asn
1               5

<210> SEQ ID NO 72
<211> LENGTH: 5
<212> TYPE: PRT
<213> ORGANISM: Artificial Sequence
<220> FEATURE:
<223> OTHER INFORMATION: From phage display library

<400> SEQUENCE: 72

Leu Leu Asp Arg Thr
1               5

<210> SEQ ID NO 73
<211> LENGTH: 4
<212> TYPE: PRT
<213> ORGANISM: Artificial Sequence
<220> FEATURE:
<223> OTHER INFORMATION: From phage display library

<400> SEQUENCE: 73

Asn Arg Thr Leu
1

<210> SEQ ID NO 74
<211> LENGTH: 4
<212> TYPE: PRT
<213> ORGANISM: Artificial Sequence
<220> FEATURE:
<223> OTHER INFORMATION: From phage display library

<400> SEQUENCE: 74

Gly Gly Gly Lys
1

<210> SEQ ID NO 75
<211> LENGTH: 16
<212> TYPE: PRT

```
<213> ORGANISM: Artificial Sequence
<220> FEATURE:
<223> OTHER INFORMATION: From phage display library

<400> SEQUENCE: 75

Asp Tyr Trp Asp Val Gly Pro Ile Tyr Arg Met Tyr Gly Gly Gly Gly
1               5                   10                  15
```